United States Patent
Green, Jr. et al.

(10) Patent No.: US 12,404,537 B2
(45) Date of Patent: *Sep. 2, 2025

(54) GENERATION OF PHASED READ-SETS FOR GENOME ASSEMBLY AND HAPLOTYPE PHASING

(71) Applicant: Dovetail Genomics, LLC, Scotts Valley, CA (US)

(72) Inventors: Richard E. Green, Jr., Santa Cruz, CA (US); Daniel S. Rokhsar, Kensington, CA (US); Paul Hartley, San Jose, CA (US); Marco Blanchette, Santa Cruz, CA (US)

(73) Assignee: DOVETAIL GENOMICS, LLC, Scotts Valley, CA (US)

( * ) Notice: Subject to any disclaimer, the term of this patent is extended or adjusted under 35 U.S.C. 154(b) by 987 days.

This patent is subject to a terminal disclaimer.

(21) Appl. No.: 17/197,551

(22) Filed: Mar. 10, 2021

(65) Prior Publication Data
US 2022/0064701 A1 Mar. 3, 2022

Related U.S. Application Data

(63) Continuation of application No. 16/078,741, filed as application No. PCT/US2017/019099 on Feb. 23, 2017, now Pat. No. 10,975,417.

(60) Provisional application No. 62/305,957, filed on Mar. 9, 2016, provisional application No. 62/298,966, filed on Feb. 23, 2016, provisional application No. 62/298,906, filed on Feb. 23, 2016.

(51) Int. Cl.
| | |
|---|---|
| C12Q 1/6806 | (2018.01) |
| C12Q 1/68 | (2018.01) |
| C12Q 1/6869 | (2018.01) |
| C40B 40/06 | (2006.01) |
| C40B 40/08 | (2006.01) |
| G01N 33/53 | (2006.01) |

(52) U.S. Cl.
CPC ............ *C12Q 1/6806* (2013.01); *C12Q 1/68* (2013.01); *C12Q 1/6869* (2013.01); *C40B 40/06* (2013.01); *C40B 40/08* (2013.01); *G01N 33/5308* (2013.01)

(58) Field of Classification Search
CPC ...... C12Q 1/68; C12Q 1/6806; C12Q 1/6869; G01N 33/5308; C40B 40/06; C40B 40/08
See application file for complete search history.

(56) References Cited

U.S. PATENT DOCUMENTS

| | | | |
|---|---|---|---|
| 1,045,793 A | 11/1912 | Houdard | |
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 4,988,617 A | 1/1991 | Landegren et al. | |
| 5,143,854 A | 9/1992 | Pirrung et al. | |
| 5,234,809 A | 8/1993 | Boom et al. | |
| 5,242,794 A | 9/1993 | Whiteley et al. | |
| 5,348,853 A | 9/1994 | Wang et al. | |
| 5,476,930 A | 12/1995 | Letsinger et al. | |
| 5,494,810 A | 2/1996 | Barany et al. | |
| 5,567,583 A | 10/1996 | Wang et al. | |
| 5,571,639 A | 11/1996 | Hubbell et al. | |
| 5,593,839 A | 1/1997 | Hubbell et al. | |
| 5,681,726 A | 10/1997 | Huse et al. | |
| 5,705,628 A | 1/1998 | Hawkins | |
| 5,780,613 A | 7/1998 | Letsinger et al. | |
| 5,786,146 A | 7/1998 | Herman et al. | |
| 5,837,832 A | 11/1998 | Chee et al. | |
| 5,989,823 A | 11/1999 | Jayasena et al. | |
| 5,994,056 A | 11/1999 | Higuchi | |
| 6,033,854 A | 3/2000 | Kurnit et al. | |
| 6,110,709 A | 8/2000 | Ausubel et al. | |
| 6,117,635 A | 9/2000 | Nazarenko et al. | |
| 6,171,785 B1 | 1/2001 | Higuchi | |
| 6,174,670 B1 | 1/2001 | Wittwer et al. | |
| 6,225,109 B1 | 5/2001 | Juncosa et al. | |
| 6,287,766 B1 | 9/2001 | Nolan et al. | |

(Continued)

FOREIGN PATENT DOCUMENTS

| | | |
|---|---|---|
| DE | 10149786 A1 | 7/2003 |
| DE | 10214395 A1 | 10/2003 |

(Continued)

OTHER PUBLICATIONS

Rhoads et al., PacBio Sequencing and Its Applications. Genomics Proteomics Bioinformatics 13:278-289 (Year: 2015).*

(Continued)

*Primary Examiner* — Ethan C Whisenant

(74) *Attorney, Agent, or Firm* — WILSON SONSINI GOODRICH & ROSATI

(57) ABSTRACT

Disclosed herein are methods, compositions and systems that facilitate accurate phasing of sequence data such as genomic sequence data through the segmentation and rearrangement of nucleic acid molecules in such a way as to preserve individual molecules' phase or physical linkage information. This is variously accomplished by binding molecules independent of their phosphodiester backbones, cleaving the molecules, ligating, and sequencing the molecules through long-read sequencing technology to recover segment sequence information spanning at least more than one segment.

19 Claims, 10 Drawing Sheets

(56) References Cited

U.S. PATENT DOCUMENTS

| | | |
|---|---|---|
| 6,326,145 B1 | 12/2001 | Whitcombe et al. |
| 6,416,950 B1 | 7/2002 | Lohse et al. |
| 6,449,562 B1 | 9/2002 | Chandler et al. |
| 6,582,938 B1 | 6/2003 | Su et al. |
| 6,787,308 B2 | 9/2004 | Balasubramanian et al. |
| 6,833,246 B2 | 12/2004 | Balasubramanian |
| 6,897,023 B2 | 5/2005 | Fu et al. |
| 6,969,488 B2 | 11/2005 | Bridgham et al. |
| 7,001,724 B1 | 2/2006 | Greenfield |
| 7,361,468 B2 | 4/2008 | Liu et al. |
| 7,414,117 B2 | 8/2008 | Saito et al. |
| 7,425,415 B2 | 9/2008 | Pfeifer et al. |
| 7,709,179 B2 | 5/2010 | Iwashita |
| 7,709,197 B2 | 5/2010 | Drmanac |
| 7,901,891 B2 | 3/2011 | Drmanac |
| 7,985,546 B2 | 7/2011 | Church et al. |
| 8,058,004 B2 | 11/2011 | Oleinikov |
| 8,071,296 B2 | 12/2011 | Ruan et al. |
| 8,076,070 B2 | 12/2011 | Chen et al. |
| 8,153,373 B2 | 4/2012 | De Laat et al. |
| 8,278,112 B2 | 10/2012 | Shokat et al. |
| 8,367,322 B2 | 2/2013 | Barany et al. |
| 8,642,295 B2 | 2/2014 | De Laat et al. |
| 8,673,562 B2 | 3/2014 | Drmanac |
| 8,741,577 B2 | 6/2014 | Graneli et al. |
| 8,841,075 B1 | 9/2014 | Borner et al. |
| 9,411,930 B2 | 8/2016 | Green, Jr. et al. |
| 9,434,985 B2 | 9/2016 | Dekker et al. |
| 9,715,573 B2 | 7/2017 | Putnam et al. |
| 9,910,955 B2 | 3/2018 | Green, Jr. et al. |
| 10,089,437 B2 | 10/2018 | Green et al. |
| 10,526,641 B2 * | 1/2020 | Fields ................. C12Q 1/6874 |
| 10,529,443 B2 | 1/2020 | Green, Jr. et al. |
| 10,825,553 B2 | 11/2020 | Green, Jr. et al. |
| 10,947,579 B2 | 3/2021 | Troll et al. |
| 10,975,417 B2 * | 4/2021 | Green, Jr. ............... C40B 40/06 |
| 11,081,209 B2 | 8/2021 | Green, Jr. et al. |
| 11,935,626 B2 | 3/2024 | Green, Jr. et al. |
| 12,006,538 B2 * | 6/2024 | de Laat ................ C12Q 1/6855 |
| 12,065,691 B2 * | 8/2024 | Troll .................... C12Q 1/6816 |
| 2001/0041340 A1 | 11/2001 | Kingsmore et al. |
| 2002/0012930 A1 | 1/2002 | Rothberg et al. |
| 2002/0127574 A1 | 9/2002 | Mirkin et al. |
| 2002/0190663 A1 | 12/2002 | Rasmussen |
| 2003/0022207 A1 | 1/2003 | Balasubramanian et al. |
| 2003/0044781 A1 | 3/2003 | Korlach et al. |
| 2003/0064398 A1 | 4/2003 | Barnes |
| 2003/0068629 A1 | 4/2003 | Rothberg et al. |
| 2003/0100102 A1 | 5/2003 | Rothberg et al. |
| 2003/0148344 A1 | 8/2003 | Rothberg et al. |
| 2003/0170689 A1 | 9/2003 | Stamatoyannapoulos et al. |
| 2003/0228627 A1 | 12/2003 | Emerson et al. |
| 2004/0106110 A1 | 6/2004 | Balasubramanian et al. |
| 2004/0197779 A1 | 10/2004 | Apffel |
| 2004/0248161 A1 | 12/2004 | Rothberg et al. |
| 2005/0079510 A1 | 4/2005 | Berka et al. |
| 2005/0100932 A1 | 5/2005 | Lapidus et al. |
| 2005/0124022 A1 | 6/2005 | Srinivasan et al. |
| 2005/0130161 A1 | 6/2005 | Fraser et al. |
| 2005/0227231 A1 | 10/2005 | Tcherkassov |
| 2005/0260625 A1 | 11/2005 | Wang |
| 2006/0012784 A1 | 1/2006 | Ulmer |
| 2006/0012793 A1 | 1/2006 | Harris |
| 2006/0024678 A1 | 2/2006 | Buzby |
| 2006/0024711 A1 | 2/2006 | Lapidus et al. |
| 2006/0078909 A1 | 4/2006 | Srinivasan et al. |
| 2006/0078937 A1 | 4/2006 | Korlach et al. |
| 2006/0252061 A1 | 11/2006 | Zabeau et al. |
| 2007/0172839 A1 | 7/2007 | Smith et al. |
| 2007/0231817 A1 | 10/2007 | De Laat et al. |
| 2007/0277251 A1 | 11/2007 | Wartiovaara et al. |
| 2009/0111115 A1 | 4/2009 | Drmanac et al. |
| 2009/0186352 A1 | 7/2009 | Akoulitchev et al. |
| 2009/0191598 A1 | 7/2009 | Ruan et al. |
| 2009/0233291 A1 | 9/2009 | Chen et al. |
| 2009/0269771 A1 | 10/2009 | Schroeder |
| 2009/0270482 A1 | 10/2009 | Schuebeler et al. |
| 2009/0298064 A1 | 12/2009 | Batzoglou et al. |
| 2010/0062947 A1 | 3/2010 | De Laat et al. |
| 2010/0081141 A1 | 4/2010 | Chen et al. |
| 2010/0093986 A1 | 4/2010 | Zwick et al. |
| 2010/0130373 A1 | 5/2010 | Dekker et al. |
| 2011/0033854 A1 | 2/2011 | Drmanac et al. |
| 2011/0256593 A1 | 10/2011 | Hsieh et al. |
| 2011/0287947 A1 | 11/2011 | Chen et al. |
| 2011/0300537 A1 | 12/2011 | Slepnev |
| 2011/0306504 A1 | 12/2011 | Xiao et al. |
| 2012/0197533 A1 | 8/2012 | Nazarenko et al. |
| 2012/0232225 A1 | 9/2012 | Baker, Jr. et al. |
| 2012/0302449 A1 | 11/2012 | Dong et al. |
| 2012/0330559 A1 | 12/2012 | Jiang et al. |
| 2013/0005585 A1 | 1/2013 | Anderson et al. |
| 2013/0045872 A1 | 2/2013 | Zhou et al. |
| 2013/0096009 A1 | 4/2013 | Dekker et al. |
| 2013/0183672 A1 | 7/2013 | De Laat et al. |
| 2013/0203605 A1 | 8/2013 | Shendure et al. |
| 2013/0310548 A1 | 11/2013 | Park |
| 2014/0031241 A1 | 1/2014 | Nicol et al. |
| 2014/0057799 A1 | 2/2014 | Johnson et al. |
| 2014/0141982 A1 | 5/2014 | Jacobson et al. |
| 2014/0220587 A1 | 8/2014 | Green, Jr. et al. |
| 2016/0194710 A1 | 7/2016 | Aiden et al. |
| 2016/0312213 A1 | 10/2016 | Rokhsar et al. |
| 2018/0119203 A1 | 5/2018 | Rice et al. |
| 2018/0203000 A1 | 7/2018 | Bertozzi et al. |
| 2018/0245079 A1 | 8/2018 | Lieberman et al. |
| 2018/0282795 A1 | 10/2018 | Marggraf-Rogalla et al. |
| 2020/0370096 A1 | 11/2020 | Blanchette et al. |
| 2020/0392574 A1 | 12/2020 | Drmanac et al. |
| 2022/0172799 A1 | 6/2022 | Green, Jr. et al. |

FOREIGN PATENT DOCUMENTS

| | | |
|---|---|---|
| DE | 10356837 A1 | 6/2005 |
| DE | 102004009704 A1 | 9/2005 |
| DE | 102004025744 A1 | 12/2005 |
| DE | 102004025745 A1 | 12/2005 |
| DE | 102004025746 A1 | 12/2005 |
| DE | 102004025694 A1 | 2/2006 |
| DE | 102004025695 A1 | 2/2006 |
| DE | 102004025696 A1 | 2/2006 |
| EP | 0476014 A1 | 3/1992 |
| EP | 0624059 A1 | 11/1994 |
| EP | 0717113 A2 | 6/1996 |
| EP | 0728520 A1 | 8/1996 |
| EP | 1967582 A1 | 9/2008 |
| EP | 2083090 A1 | 7/2009 |
| EP | 2624059 A1 | 8/2013 |
| EP | 2951319 B1 | 3/2021 |
| GB | 2519255 A | 4/2015 |
| KR | 20120044096 A | 5/2012 |
| WO | WO-9015070 A1 | 12/1990 |
| WO | WO-9210092 A1 | 6/1992 |
| WO | WO-9309668 A1 | 5/1993 |
| WO | WO-9551995 A1 | 5/1995 |
| WO | WO-9729212 A1 | 8/1997 |
| WO | WO-9841651 A1 | 9/1998 |
| WO | WO-0014281 A2 | 3/2000 |
| WO | WO-02088382 A2 | 11/2002 |
| WO | WO-02103046 A2 | 12/2002 |
| WO | WO-03020968 A2 | 3/2003 |
| WO | WO-03031947 A2 | 4/2003 |
| WO | WO-03042657 A2 | 5/2003 |
| WO | WO-2005001113 A2 | 1/2005 |
| WO | WO-2005005655 A1 | 1/2005 |
| WO | WO-2005005657 A1 | 1/2005 |
| WO | WO-2005044836 A2 | 5/2005 |
| WO | WO-2006040550 A1 | 4/2006 |
| WO | WO-2006097320 A2 | 9/2006 |
| WO | WO-2007093819 A2 | 8/2007 |
| WO | WO-2008024473 A2 | 2/2008 |
| WO | WO-2008127281 A2 | 10/2008 |
| WO | WO-2008143903 A2 | 11/2008 |
| WO | WO-2009053039 A1 | 4/2009 |

(56) References Cited

FOREIGN PATENT DOCUMENTS

| WO | WO-2009147386 A1 | 12/2009 |
|---|---|---|
| WO | WO-2010036323 A1 | 4/2010 |
| WO | WO-2011056872 A2 | 5/2011 |
| WO | 2012005595 A2 | 1/2012 |
| WO | WO-2012045012 A2 | 4/2012 |
| WO | WO-2012047726 A1 | 4/2012 |
| WO | WO-2012054873 A2 | 4/2012 |
| WO | WO-2012106546 A2 | 8/2012 |
| WO | WO-2012116331 A2 | 8/2012 |
| WO | WO-2012142531 A2 | 10/2012 |
| WO | WO-2012142611 A2 | 10/2012 |
| WO | WO-2012150317 A1 | 11/2012 |
| WO | WO-2013078470 A2 | 5/2013 |
| WO | WO-2014012010 A1 | 1/2014 |
| WO | WO-2014047561 A1 | 3/2014 |
| WO | WO-2014121091 A1 | 8/2014 |
| WO | WO-2015010051 A1 | 1/2015 |
| WO | WO-2015089243 A1 | 6/2015 |
| WO | WO-2015123588 A1 | 8/2015 |
| WO | WO-2016019360 A1 | 2/2016 |
| WO | WO-2016044313 A1 | 3/2016 |
| WO | WO-2016061517 A2 | 4/2016 |
| WO | WO-2016164313 A1 | 10/2016 |
| WO | WO-2016207647 A1 | 12/2016 |
| WO | WO-2016207653 A1 | 12/2016 |
| WO | WO-2016207661 A1 | 12/2016 |
| WO | WO-2021061841 A1 | 4/2021 |
| WO | WO-2021064463 A1 | 4/2021 |
| WO | WO-2023091592 A1 | 5/2023 |

OTHER PUBLICATIONS

Putnam et al., Chromosome-scale shotgun assembly using an in vitro method for long-range linkage. Genome Research 26:342-350 (Year: 2016).*
Kaplan, et al. High-throughput genome scaffolding from in-vivo DNA interaction frequency. Nat. Biotechnol. 31:1139-1143 (2013).
O'Neill LP, Turner BM. Immunoprecipitation of native chromatin: NChIP. Methods. 31(1):76-82 (2003).
PCT/US2022/050291 International Invitation to Pay Additional Fees dated Jan. 27, 2023.
PCT/US2022/050291 International Search Report and Written Opinion dated Apr. 25, 2023.
Adams, et al. The Genome Sequence of Drosophila melanogaster. Science Mar. 24, 2000, 287.5461: 2185-2195.
Adey, A. et al. In vitro, long-range sequence information for 19 de novo genome assembly via transposase contiguity. Genome Res., 24(12):2041-2049, Dec. 2014.
Alkan, C. et al. Limitations of next-generation genome sequence assembly. Nat. Methods, 8(1):61-65, Jan. 2011.
Allahyar et al. Enhancer hubs and loop collisions identified from single-allele topologies. Nature Genetics 50(8):1151-1160 (Aug. 2018).
Allison 2007 Fundamental Molecular Biology. Wiley-Blackwell, Chapter 8, pp. 1-15.
Amini, S et al. Haplotype-resolved whole-genome sequencing by contiguity-preserving transposition and combinatorial indexing. Nat. Genet., 46(12):1343-1349, Dec. 2014.
Ausubel, et al., eds. 1993. Current Protocols in Molecular Biology. Part 1: E. coli, plasmids, and bacteriophages,pp. 1-15.
Ay et al. Identifying multi-locus chromatin contacts in human cells using tethered multiple 3c. BMC Genomics 16(1):121 (Feb. 2015).
Bansal et al., Hapcut: an efficient and accurate algorithm for the haplotype assembly problem, Bioinformatics, 24(16): i153-i159 (Aug. 9, 2008).
Beagrie et al. Complex multi-enhancer contacts captured by genome architecture mapping. Nature 543(7646):519-524 (Mar. 2017).
Belton et al. Hi-C: a comprehensive technique to capture the conformation of genomes. Methods 58(3):268-276 (Nov. 1, 2012).

Blander, G. et al.SIRT1 Shows No Substrate Specificity in Vitro. Journal of biological Chemistry (2005) vol. 280, p. 9780-9785.
Blecher-Gonen, Ronnie et al. High-throughput chromatin immunoprecipitation for genome-wide mapping of in vivo protein-DNA interactions and epigenomic states. Nature Protocols, 8(3):539-554 (Feb. 21, 2013).
Bolger, A.M. et al. Trimmomatic: a flexible trimmer for Illumina sequence data. Bioinformatics, 30(15):2114-2120, Aug. 2014.
Bradnam, K.R. et al. Assemblathon 2: evaluating de novo methods of genome assembly in three vertebrate species. Gigascience, 2(1): 10, 2013.
Burton, et al. Chromosome-scale scaffolding of de novo genome assemblies based on chromatin interactions. Nat. Biotechnol. 2013, 31: 1119-1125.
Cai et al., "SATB1 packages densely looped transcriptionally active chromatin for coordinated expression of cytokine genes," Nature Genetics, 2006, vol. 38, No. 11, pp. 1278-1288.
Chapman, et al. Meraculous: de novo genome assembly with short paired-end reads. PloS one. 2011, 6.8: e23501.
Constans, A. All in the Family Scientist 13: 36 (2003).
Constans. Beyond Sanger: Toward the $1,000 Genome—The Scientist—Magazine of the Life Sciences. The Scientist. Jun. 30, 2003; 17(13):36.
Cortese, J. Array of options. Scientist. 2000, 14.11: 26.
Cortese, J. The array of today. Scientist. 2000, 14.17: 25.
Darrow et al. Deletion of DXZ4 on the human inactive X chromosome alters higher-order genome architecture. PNAS USA 113(31): E4504-E4512 (Aug. 2016).
De Koning, A.P. et al. Repetitive elements may comprise over two-thirds of the human genome. PLoS Genet., 7(12):e1002384, Dec. 2011.
Dekker et al., A closer look at long-range chromosomal interactions. TRENDS in Biochemical Science (Jun. 2003) 28(6):277-280.
Dekker et al., "Capturing chromosome conformation," Science, 2002, vol. 295, pp. 1306-1311.
Dixon, J. R. et al. Topological domains in mammalian genomes identified by analysis of chromatin interactions. Nature, 485(7398):376-380, May 2012.
Dostie et al., "Chromosome Conformation Capture Carbon Copy (5C): a massively parallel solution for mapping interaction between genomic elements," Genome research, 2006, vol. 16, No. 10, pp. 1299-1309.
Dower, et al. Recombinant and synthetic randomized peptide libraries. Ann. Rep. Med. Chem. 1991, 26:271-280.
Drmanac, et al. Human Genome Sequencing Using Unchained Base Reads on Self-Assembling DNA Nanoarrays. Science Jan. 1, 2010, 327.5961: 78-81.
Ekins, R. et al. Microarrays: Their Origins and applications. Trends in Biotechnology, 17(6); 217-218 (Jun. 1999).
Enoiu, Milica et al. Repair of cisplatin-induced DNA interstand crosslinks by a replication-independent pathway involving transcription-coupled repair and translesion synthesis. Nucleic Acids Research, 40(18):8953-8964 (2012).
Extended European Search Report, Application No. 14745949.9 European Patent Office, Nov. 21, 2016.
Fan et al. "A versatile assay for high-throughput gene expression profiling on universal array matrices." Genome Research, 2004, vol. 14 No. 5 pp. 878-885.
Fangman, et al. Activation of replication origins within yeast chromosomes, Annual Review of Cell Biology, 7(1); 375-402 (1991).
Ferraiuolo, M.A. et al. From cells to chromatin: capturing snapshots of genome organization with 5C technology. Methods. Nov. 2012;58(3):255-67. Epub Nov. 5, 2012.
Flot, JF et al. Contact genomics: scaffolding and phasing (meta) genomes using chromosome 3D physical signatures. FEBS Letters 589 (2015) 2966-2974.
Fodor, et al. Light-directed, spatially addressable parallel chemical synthesis. Science. Feb. 15, 1991, 251.4995: 767-773.
Fullwood, et al. "ChIP-Based Methods for the Identification of Long-Range Chromatin Interactions" Journal of Cellular Biochemistry, vol. 107, No. 1, pp. 30-39, May 2009.

(56) References Cited

OTHER PUBLICATIONS

Fullwood, et al. Next Generation DNA sequencin of paired-end tags (PET) for transcriptome and genome analyses. Genome Research. 19(4):521-532 (Apr. 2009).
Fullwood, MJ et al. Chromatin interaction analysis using paired-end tag sequencing. Jan. 2010. Curr. Prot. In Mol. Biol. Chapter 21; unit 21 .15.1-25.
Fyodorov, et al. Chromatin assembly in vitro with purified recombinant ACF and NAP-1. Methods in enzymology. 2002, 371: 499-515.
Garaj, et al. Graphene as a sub-nanometer trans-electrode membrane. Nature. Sep. 9, 2010, 467.7312: 190-193.
GE Healthcare: Instructions 71-7106-00AF Activated Thiol Sepharose 4B (pp. 1-12) (Jul. 2008).
Gilmour, David S., et al. Detecting protein-DNA interactions in vivo: distribution of RNA polymerase on specific bacterial genes. Proceedings of the National Academy of Sciences. (1984) 81(14): 4275-4279.
Gnerre, S. et al. High-quality draft assemblies of mammalian genomes from massively parallel sequence data. Proc. Natl. Acad. Sci. U.S.A., 108 (4):1513-1518, Jan. 2011.
Goodwin, S. et al. Oxford nanopore sequencing and de novo assembly of a eukaryotic genome. bioRxiv, pp. 1-28 (Jul. 15, 2015).
Green R.E. et al. Three crocodilian genomes reveal ancestral patterns of evolution among archosaurs. Science, 346(6215): 1254449 (1-11) (Dec. 12, 2014).
Grunenwald et al., "Rapid, high-throughput library preparation for next-generation sequencing" 2010 Nature Methods, vol. 7.
Gwynne, P. et al. Microarray analysis: the next revolution in molecular biology. Science. pp. 1-6 (Aug. 6, 1999).
Haussler, D., et al. Genome 10K: a proposal to obtain whole-genome sequence for 10,000 vertebrate species. J. Hered., 100(6):659-674, 2009.
Heid, C.A. et al. Real time quantitative PCR. Genome Research, 6(10): 986-994 (1996).
Herschleb, J. et al. Pulsed-field gel electrophoresis. Pulsed-field gel electrophoresis. Nature Protocols 2(3):677-84 (Mar. 29, 2007).
Hesselberth, Jay R. et al. Global mapping of protein-DNA interaction in vivo by digital genomic footprinting, Nature Methods 6(4): 283-289 (Apr. 2009).
International Application No. PCT/US16/57557 International Search Report and Written Opinion Mailed Mar. 10, 2017.
International Application No. PCT/US17/32466 International Search Report and Written Opinion Mailed Aug. 22, 2017.
International Application No. PCT/US2014/014184 International Search Report and Written Opinion Mailed Apr. 23, 2014.
International Application No. PCT/US2015/043327 International Preliminary Report on Patentability Mailed Feb. 7, 2017.
International Application No. PCT/US2016/018295 International Preliminary Report on Patentability Mailed Aug. 31, 2017.
International Application No. PCT/US2016/018295 International Search Report Issued Aug. 4, 2016.
International Application No. PCT/US2016/024225 International Preliminary Report on Patentability Mailed Sep. 26, 2017.
International Application No. PCT/US2016/024225 International Search Report Issued Jul. 10, 2016.
International Application No. PCT/US2017/019099 International Preliminary Report on Patentability and Written Opinion Mailed Sep. 7, 2018.
International Human Genome Sequencing Consortium. Finishing the euchromatic sequence of the human genome. Nature, 431(7011): 931-945, Oct. 2004.
International Preliminary Report on Patentability and Written Opinion, PCT/US2014/069642, Jun. 23, 2016.
Kalhor, R. et al. Genome architectures revealed by tethered chromosome conformation capture and population-based modeling, Nature Biotechnology, 30(1): 90-98 (Jan. 2012).
Kaplan, N. et al. High-throughput genome scaffolding from in vivo DNA interaction frequency. Nat. Biotechnol., 31(12):1143-1147 (Dec. 2013).
Kidd, J. M. et al. Mapping and sequencing of structural variation from eight human genomes. Nature, 453(7191):56-64, May 2008.
Kitzman, Jacob O. et al. Haplotype-resolved genome sequencing of a Gujarati Indian individual, Nature Biotechnology, 29(1): 59-63 (Jan. 2011).
Korbel et al., Genome assembly and haplotyping with Hi-C. Nat Biotechnol. 31(12):1099-1101 (2013).
Koren, S. et al. Hybrid error correction and de novo assembly of single-molecule sequencing reads. Nature biotechnology, 30(7):693-700, 2012.
Kotoulas, S. et al. The chipping forecast. Special supplement to Nature Genetics vol. 21; pp. 1-6 (1999).
Kundu et al. Activator-dependent transcription from chromatin in vitro involving targeted histone acetylation by p300. Molecular cell. 2000, 6.3: 551-561.
Lasken, Roger S. et al. Mechanism of chimera formation during the Multiple Displacement Amplification reaction. BMC biotechnology. 7(19):1-11 (Apr. 12, 2007).
Lee, T.I. et al. Chromatin immunoprecipitation and microarray-based analysis of protein location, Nature Protocols 1(2): 729-748 (2006).
Lemieux, B. et al. Overview of DNA chip technology. Molecular Breeding 4: 277-289 (1998).
Levene, M.J. et al., Zero-Mode Waveguides for Single-Molecule Analysis at High Concentrations, Science, 299(5607):682-686 (Jan. 31, 2003).
Lieberman-Aiden, E. et al. Comprehensive mapping of long-range interactions reveals folding principles of the human genome. Science, 326(5950):289-293, Oct. 2009.
Liu, B. et al. COPE: an accurate k-mer-based pair-end reads connection tool to facilitate genome assembly. Bioinformatics, 28(22): 2870-2874 (Oct. 8, 2012).
Lupski, James R. et al. Whole-genome sequencing in a patient with Charcot-Marie-Tooth neuropathy. New England Journal of Medicine, 362(13): 1181-1191 (Apr. 1, 2010).
Lusser, Alexandra et al. Strategies for the reconstitution of chromatin. Nature Methods, 1(1):19-26 (Oct. 2004).
Ma et al., Fine-scale chromatin interaction maps reveal the cis-regulatory landscape of human lincRNA genes. Nat Methods 12(1):71-78 (2015).
Ma, H. et al. Application of Real-time Polymerase Chain Reaction (RT-PCR), The Journal of American Science, 2 (3):1-15 (Aug. 10, 2006).
Maniatis, et al. Molecular Cloning: A Laboratory Manual, Cold Spring Harbor, N.Y., pp. 280-281 (1982).
Margulies, M. et al. Genome sequencing in open microfabricated high density picolitre reactors. Nature 437(7057):376-380 (Sep. 15, 2005).
Marie-Nelly, H. et al. High-quality genome (re)assembly using chromosomal contact data. Nature Communications 5:5695 (Dec. 17, 2014).
Marshall, A. et al. DNA chips: an array of possibilities. Nature Biotechnology, 16(1): 27-31 (Jan. 1998).
Mary, I. et al. Metaproteomic and metagenomic analyses of defined oceanic microbial populations using microwave cell fixation and flow cytometric sorting. FEMS Microbiol Ecol. 74(1):10-18 (Oct. 2010). E-Pub. Jul. 5, 2010.
Meyer, M. et al. Illumina sequencing library preparation for highly multiplexed target capture and sequencing. Cold Spring Harb Protoc, 2010(6):pdb.prot5448 (Jun. 2010).
Miele et al., Mapping Chromatin Interactions by Chromosome Conformation Capture. Current Protocols in Molecular Biology. Unit 21.11 pp. 1-21 (2006).
Miller et al. A Simple salting out procedure for extracting DNA from human nucleated cells. Nucleic Acids Research vol. 16, No. 3, 1215 (1988).
Morrison, AJ et al. Retinoblastoma Protein Transcriptional Repression through Histone Deacetylation of a Single Nucleosome. Molecular and Cellular biology 22(3);856-865 (Feb. 2002).
Myers, E.W. et al. A Whole-Genome Assembly of *Drosohila*. Science, 287(5461):2196-2204 (Mar. 24, 2000).

(56) References Cited

OTHER PUBLICATIONS

Nazarenko, I.A. et al. A closed tube format for amplification and detection of DNA based on energy transfer. Nucleic acids research, 25(12):2516-2521 (Jun. 15, 1997).
Olivares-Chauvet et al. Capturing pairwise and multi-way chromosomal conformations using chromosomal walks. Nature 540(7632):296-300 (Dec. 2016).
Oudelaar et al. Single-allele chromatin interactions identify regulatory hubs in dynamic compartmentalized domains. Nature Genetics 50(12):1744-1751 (2018).
PCT/US2014/014184 International Preliminary Report on Patentability dated Aug. 13, 2015.
PCT/US2014/014184 International Search Report dated Apr. 23, 2014.
Peng, Z. et al. Generation of long insert pairs using a Cre-LoxP Inverse PCR approach, PLoS One, 7(1): e29437 (2012) E-Pub Jan. 9, 2012.
Peters, B.A. et al. Accurate whole-genome sequencing and haplotyping from 10 to 20 human cells. Nature, 487(7406):190-195 (Jul. 11, 2012).
Poster—Pore-C: using nanopore reads to delineate long-range interactions between genomic loci in the human genome. (2018).
Putnam, N. H. et al. Supplemental Material—Chromosome-scale shotgun assembly using an in vitro method for long-range linkage. Genome Research 26:342-350 (2016). E-Pub Feb. 4, 2016.
Putnam, N.H. et al. Chromosome-scale shotgun assembly using an in vitro method for long-range linkage. arXiv:1502.05331[q-bio.GN] pp. 1-25. Feb. 18, 2015 (Retrieved from the Internet Oct. 8, 2015).
Putnam, Nicholas H. et al. Chromosome-scale shotgun assembly using an in vitro method for long-range linkage. Genome Research, 26(3):342-350 (Mar. 2016).
Quail, M.A. et al. A tale of three next generation sequencing platforms: comparison of Ion Torrent, Pacific Biosciences and Illumina MiSeq sequencers. BMC Genomics, 13:341 (Jul. 24, 2012).
Quinodoz et al. Higher-order inter-chromosomal hubs shape 3D genome organization in the nucleus. Cell, 174(3):744-757.e24 (Jul. 2018).
Rios, J. et al. Identification by whole-genome resequencing of gene defect responsible for severe hypercholesterolemia. Human Molecular Genetics, 19(22): 4313-4318 (Nov. 15, 2010). E-Pub Aug. 18, 2010).
Rozowsky, J. et al. AlleleSeq: analysis of allele-specific expression and binding in a network framework. Mol. Syst. Biol., 7:522; pp. 1-15 (Aug. 2, 2011).
Salzberg, S.L. et al. GAGE: A critical evaluation of genome assemblies and assembly algorithms. Genome Res., 22(3):557-567 (Mar. 2012). E-Pub Jan. 6, 2012.
Sambrook, et al. Mixed Oligonucleotide-primed Amplification of cDNA (MOPAC). Cold Spring Harbor Protocols, pp. 1-30 (2006).
Schena M. (ed.), Microarray Biochip Technology (2000). A bioTechniques Books Publication. Eaton Publishing, pp. 1-44. ISBN-10: 1881299376 ISBN-13: 978-1881299370.
Schena, M. et al. PCR applications: protocols for functional genomics. Chapter 28: Parallel analysis with biological chips. Eds. Michael A. Innis, David H. Gelfand, John J. Sninsky. Academic Press. ISBN: 0-12-372185-7. pp. 445-456 (1999).
Schena, Mark et al. Genes, genomes, and chips. DNA microarrays: A practical approach. Oxford University Press, pp. 1-18 (1999); ISBN-10: 1881299376 ISBN-13: 978-1881299370.
Schloss, P.D. et al. A statistical toolbox for metagenomics: assessing functional diversity in microbial communities, BMC Bioinformatics 9(34):1-15 (Jan. 23, 2008).
Schmidt, D. et al. ChIP-seq: using high-throughput sequencing to discover protein-DNA interactions. Methods 48(3): 240-248(Jul. 2009).

Schutze, T. et al. A calibrated diversity assay for nucleic acid libraries using DiStRO—a Diversity Standard of Random Oligonucleotides. Nucleic Acids Research, 38(4):e23 (pp. 1-5) Mar. 2010; epub Dec. 3, 2009.
Schwartz, D.C. et al. Separation of yeast chromosome-sized DNAs by pulsed field gradient gel electrophoresis. Cell 37(1): 67-75 (May 1984).
Selvaraj, S. et al. Whole-genome haplotype reconstruction using proximity-ligation and shotgun sequencing. Nature Biotechnology, 31(12):1111-1118 (Dec. 2013).
Selvaraj, S. et al. Complete haplotype phasing of the MHC and KIR loci with targeted HaploSeq. BMC Genomics 16:900, pp. 1-7 (Nov. 5, 2015).
Shalon, D. et al. A DNA microarray system for analyzing complex DNA samples using two-color fluorescent probe hybridization. Genome research, 6(7): 639-645 (Jul. 1996).
Shedlock, A.M. et al. Phylogenomics of nonavian reptiles and the structure of the ancestral amniote genome. Proc. Natl. Acad. Sci. U.S.A., 104(8):2767-2772 (Feb. 20, 2007). E-Pub Feb. 16, 2007.
Sheridan, C. Milestone approval lifts Illumina's NGS from research into clinic. Nature Biotechnology, 32(2): 111-112 (Feb. 2014).
Shiio Y., et al. Quantitative proteome analysis using isotope-coded affinity tags and mass spectrometry. Nature Protocols, 1(1): 139-145 (2006).
Sigma Protein A immobilized product sheet (Published Mar. 2001) accessed on Apr. 14, 2016.
Simpson, et al. Efficient de novo assembly of large genomes using compressed data structures. Genome Res. Mar. 2012; 22(3): 549-556.
Solomon, M.J. et al. Formaldehyde-mediated DNA-protein crosslinking: a probe for in vivo chromatin structures. Proceedings of the National Academy of Sciences, 82(19): 6470-6474 (Oct. 1985).
Solomon, M.J. et al. Mapping protein-DNA interactions in vivo with formaldehyde: evidence that histone H4 is retained on a highly transcribed gene. Cell, 53(6):937-947 (Jun. 17, 1988).
Soni, et al. Progress toward ultrafast DNA sequencing using solid-state nanopores. Clin Chem, 53(11):1996-2001 (Nov. 2007). Epub Sep. 21, 2007.
Splinter, E. 3C Technology: Analyzing the Spatial Organization of Genomic Loci In Vivo Methods in Enzymology, 375:493-507 (2004).
Splinter, E. et al. Determining long-range chromatin interactions for selected genomic sites using 4C-seq technology: from fixation to computation. Methods. Nov. 2012;58(3):221-30. (Epub May 17, 2012).
Stadhouders et al., Multiplexed chromosome conformation capture sequencing for rapid genome-scale high-resolution detection of long-range chromatin interactions. Nature Protocols. 8(3):509-524 (2013).
Storek, Michael J. et al. High-resolution footprinting of sequence-specific protein-DNA contacts, Nature Biotechnology, 20(2):183-186 (Feb. 1, 2002).
Syed, F. et al. Optimized library preparation method for next-generation sequencing. Application Note Abstract, Nature Methods 6:i-ii (Oct. 2009).
Tanizawa, H. et al., Mapping of long-range associations throughout the fission yeast genome reveals global genome organization linked to transcriptional regulation. Nucleic Acid Research, 38(22):8164-8177 (Dec. 2010). Epub Oct. 28, 2010.
Teague, B. et al. High-resolution human genome structure by single-molecule analysis. Proceedings of the National Academy of Sciences, 107(24): 10848-10853 (Jun. 15, 2010).
ThermoScientific Product Information sheets for DNaseI, RNase-free (2016).
Torjensen, I. Genomes of 100,000 people will be sequenced to create an open access research resource. BMJ, 347:f6690 (Nov. 6, 2013).
Tuzun, E. et al. Fine-scale structural variation of the human genome. Nat. Genet., 37(7):727-732 (Jul. 2005). Epub May 15, 2005.
Tyagi, S. et al. Molecular beacons: probes that fluoresce upon hybridization. Nature Biotechnology, 14(3):303-308 (Mar. 1996).
Ulahannan et al., Nanopore sequencing of DNA concatemers reveals higher-order features of chromatin structure. BioRxlv: 1-8 (2019).

(56) References Cited

OTHER PUBLICATIONS

Umbarger, M.A. Chromosome conformation capture assays in bacteria. Methods 58(3):212-220 (Nov. 2012).
U.S. Appl. No. 14/764,945 Non-Final Office Action Mailed Sep. 22, 2017.
U.S. Appl. No. 15/045,818 Non-Final Office Action Mailed Jan. 30, 2017.
U.S. Appl. No. 15/045,818 Non-final Office Action Mailed Sep. 1, 2016.
U.S. Appl. No. 15/045,818 Notice of Allowance Mailed May 19, 2017.
U.S. Appl. No. 15/137,988 Notice of Allowance Mailed Mar. 15, 2017.
U.S. Appl. No. 15/167,880 Non-Final Office Action Mailed Jul. 3, 2017.
U.S. Appl. No. 15/167,880 Notice of Allowance Mailed Oct. 26, 2017.
U.S. Appl. No. 15/329,414 Final Office Action Mailed Oct. 9, 2018.
U.S. Appl. No. 15/632,895 Final Office Action Mailed Sep. 10, 2018.
U.S. Appl. No. 15/649,268 Advisory Office Action Mailed Aug. 16, 2018.
U.S. Appl. No. 15/649,268 Non-Final Office Action Mailed Oct. 20, 2017.
U.S. Appl. No. 16/078,741 Non-Final Office Action dated Nov. 19, 2020.
U.S. Appl. No. 16/128,297 Non-Final Office Action dated Nov. 18, 2020.
U.S. Appl. No. 14/170,339 Non-Final Office Action Dated Oct. 20, 2014.
U.S. Appl. No. 14/170,339 Restriction Requirement Dated Mar. 14, 2014.
U.S. Appl. No. 16/078,741 Non-Final Office Action dated Jun. 4, 2020.
Venter, J.C. et al. The sequence of the human genome. Science, 291(5507):1304-1351 (Feb. 16, 2001).
Voskoboynik, A. et al. The genome sequence of the colonial chordate, Botryllus schlosseri. eLife, 2:e00569 (2013). doi: 10.7554/eLife.00569. Epub Jul. 2, 2013.
Weisenfeld N.I., et al. Comprehensive variation discovery in single human genomes. Nat. Genet. 46(12):1350-1355 (Dec. 2014).
Whitcombe, D. et al. Detection of PCR Products Using Self-probing Amplicons and Fluorescence. Nature Biotechnology, 17(8):804-807 (Aug. 1999).
Williams, L.J. Paired-end sequencing of Fosmid libraries by Illumina. Genome Res., 22(11):2241-2249 (Nov. 2012). Epub Jul. 16, 2012.
Wing, R.D., et al. An improved method of plant megabase DNA isolation in agarose microbeads suitable for physical mapping and YAC cloning. The Plant Journal, 4(5):893-898 (1993).
Wu, C.C. et al. Long-span, mate-pair scaffolding and other methods for faster next-generation sequencing library creation. Nat. Methods, 9(9; Advertising Feature):i-ii (Sep. 2012).
Wu, T.D. et al. GMAP: a genomic mapping and alignment program for mRNA and EST sequences. Bioinformatics, 21(9):1859-1875, May 1, 2005. Epub Feb. 22, 2005.
Zheng et al. Multiplex chromatin interactions with single-molecule precision. Nature 566(7745):558-562 (Feb. 2019).
Zhou, S. et al. A single molecule scaffold for the maize genome. PLoS Genetics, 5(11): e1000711; pp. 1-14 (Nov. 20, 2009).
Zinchenko, A. et al. Compaction of Single-Chain DNA by Histone-Inspired Nanoparticles. Physical Review Letters, 95(22); 228101 (2005).
De Vree, Paula JP, et al. Targeted sequencing by proximity De Vree et al., Targeted sequencing by proximity ligation for comprehensive variant detection and local haplotyping, pp. 1-9, Aug. 17, 2014, Nature Biotechnology. Supplemental Content attached. 33 pages.

* cited by examiner

Ligation connects free-ends through punctuation oligo

GENERATION OF PHASED READ-SETS FOR GENOME ASSEMBLY AND HAPLOTYPE PHASING

CROSS-REFERENCE

This application is a continuation of U.S. patent application Ser. No. 16/078,741, filed Aug. 22, 2018, which is national stage entry of International Application No. PCT/US17/19099, filed Feb. 23, 2017, which claims the benefit of U.S. Provisional Application No. 62/298,906, filed Feb. 23, 2016, which is hereby explicitly incorporated by reference in its entirety, and this application also claims the benefit of U.S. Provisional Application No. 62/298,966, filed Feb. 23, 2016, which is hereby explicitly incorporated by reference in its entirety, and this application also claims the benefit of U.S. Provisional Application No. 62/305,957, filed Mar. 9, 2016, which is hereby explicitly incorporated by reference in its entirety.

BACKGROUND

It remains difficult in theory and in practice to determine haplotype phase information of complex DNA samples, such as those having diploid or polyploid genomes, or those comprising substantial amounts of repetitive or identical sequence. Difficulties arise from loci of interest being separated by highly repetitive regions or by long stretches of identical sequence, such that standard assembly of read information is insufficient to assign phase information to alleles at a locus.

SUMMARY

Disclosed herein are methods, compositions and systems related to the accurate phasing of nucleic acid sequence data through the generation and sequencing, such as long-read sequencing, of segmentally rearranged nucleic acid molecules such as chromosomes.

Disclosed herein are methods of generating long-distance phase information from a first DNA molecule, comprising a) providing a first DNA molecule having a first segment and a second segment, wherein the first segment and the second segment are not adjacent on the first DNA molecule; b) contacting the first DNA molecule to a DNA binding moiety such that the first segment and the second segment are bound to the DNA binding moiety independent of a common phosphodiester backbone of the first DNA molecule; c) cleaving the first DNA molecule such that the first segment and the second segment are not joined by a common phosphodiester backbone; d) attaching the first segment to the second segment via a phosphodiester bond to form a reassembled first DNA molecule; and e) sequencing at least 4 kb of consecutive sequence of the reassembled first DNA molecule comprising a junction between the first segment and the second segment in a single sequencing read, wherein first segment sequence and second segment sequence represent long-distance phase information from a first DNA molecule. In some aspects the DNA binding moiety comprises a plurality of DNA-binding molecules, such as DNA-binding proteins. In some aspects the population of DNA-binding proteins comprises nuclear proteins broadly, nucleosomes, or in some cases, more specifically histones. In some aspects contacting the first DNA molecule to a plurality of DNA-binding moieties comprises contacting to a population of DNA-binding nanoparticles. Often, the first DNA molecule has a third segment not adjacent on the first DNA molecule to the first segment or the second segment, wherein the contacting in (b) is conducted such that the third segment is bound to the DNA binding moiety independent of the common phosphodiester backbone of the first DNA molecule, wherein the cleaving in (c) is conducted such that the third segment is not joined by a common phosphodiester backbone to the first segment and the second segment, wherein the attaching comprises attaching the third segment to the second segment via a phosphodiester bond to form the reassembled first DNA molecule, and wherein the consecutive sequence sequenced in (e) comprises a junction between the second segment and the third segment in a single sequencing read. The method often comprises contacting the first DNA molecule to a cross-linking agent, such as formaldehyde. In some aspects the DNA binding moiety is bound to a surface comprising a plurality of DNA binding moieties. In some aspects the DNA binding moiety is bound to a solid framework comprising a bead. In some aspects cleaving the first DNA molecule comprises contacting to a restriction endonuclease such as a nonspecific endonuclease, a tagmentation enzyme, or a transposase. In some aspects cleaving the first DNA molecule comprises shearing the first molecule. Optionally, the method comprises adding a tag to at least one exposed end. Exemplary tags comprise a labeled base, a methylated base, a biotinylated base, uridine, or any other noncanonical base. In some aspects the tag generates a blunt ended exposed end. In some aspects the method comprises adding at least one base to a recessed strand of a first segment sticky end. In some aspects the method comprises adding a linker oligo comprising an overhang that anneals to the first segment sticky end. In some aspects the linker oligo comprises an overhang that anneals to the first segment sticky end and an overhang that anneals to the second segment sticky end. In some aspects the linker oligo does not comprise two 5' phosphate moieties. In some aspects attaching comprises ligating. In some aspects attaching comprises DNA single strand nick repair. In some aspects the first segment and the second segment are separated by at least 10 kb on the first DNA molecule prior to cleaving the first DNA molecule. In some aspects the first segment and the second segment are separated by at least 15 kb on the first DNA molecule prior to cleaving the first DNA molecule. In some aspects the first segment and the second segment are separated by at least 30 kb on the first DNA molecule prior to cleaving the first DNA molecule. In some aspects the first segment and the second segment are separated by at least 50 kb on the first DNA molecule prior to cleaving the first DNA molecule. In some aspects the first segment and the second segment are separated by at least 100 kb on the first DNA molecule prior to cleaving the first DNA molecule. In some aspects the sequencing comprises single molecule long read sequencing. In some aspects the long read sequencing comprises a read of at least 5 kb. In some aspects the long read sequencing comprises a read of at least 10 kb. In some aspects the first reassembled DNA molecule comprises a hairpin moiety linking a 5' end to a 3' end at one end of the first DNA molecule. In some aspects the method comprises sequencing a second reassembled version of the first DNA molecule. In some aspects the first segment and the second segment are each at least 500 bp. In some aspects the first segment, the second segment, and the third segment are each at least 500 bp.

Disclosed herein are methods of genome assembly comprising: a) obtaining a first DNA molecule complexed to a structure; b) cleaving the first DNA molecule to form a first exposed end and a second exposed end, wherein the first exposed end and the second exposed end were not adjacent on the molecule prior to said cleaving; c) cleaving the first DNA molecule to form a third exposed end and a fourth exposed end, wherein the third exposed end and the fourth exposed end were not adjacent on the molecule prior to said cleaving; d) attaching said first exposed end and said second exposed end to form a first junction; e) attaching said third exposed end and said fourth exposed end to form a second junction; f) sequencing across said first junction and said second junction in a single sequencing read; g) mapping sequence on a first side of said first junction to a first contig of said plurality of contigs; h) mapping sequence on a second side of said first junction to a second contig of said plurality of contigs; i) mapping sequence on a first side of said second junction to a second contig of said plurality of contigs; j) mapping sequence on a second side of said second junction to a third contig of said plurality of contigs; and k) assigning said first contig, said second contig, and said third contig to a common phase of a genome assembly. In some aspects, said plurality of contigs are generated from shotgun sequence data. In some aspects said plurality of contigs are generated from single molecule long read data. In some aspects, said single molecule long read data comprises said plurality of contigs. In some aspects, said plurality of contigs is concurrently obtained through sequencing across said first junction and said second junction. In some aspects, sequencing across said marker oligo comprises sequencing at least 10 kb. In some aspects, said structure comprises a population of DNA binding moieties bound to the first DNA molecule to form reconstituted chromatin. In some aspects, said reconstituted chromatin is contacted to a crosslinking agent. In some aspects, said crosslinking agent comprises formaldehyde. In some aspects, said population of DNA binding moieties comprises histones. In some aspects, said population of DNA binding moieties comprises nanoparticles. In some aspects, said structure comprises native chromatin. In some aspects, the first exposed end and the second exposed end are separated by at least 10 kb on the first DNA molecule prior to cleaving the first DNA molecule. In some aspects, the first exposed end and the second exposed end are separated by at least 15 kb on the first DNA molecule prior to cleaving the first DNA molecule. In some aspects, the first exposed end and the second exposed end are separated by at least 30 kb on the first DNA molecule prior to cleaving the first DNA molecule. In some aspects, the first exposed end and the second exposed end are separated by at least 50 kb on the first DNA molecule prior to cleaving the first DNA molecule. In some aspects, the first exposed end and the second exposed end are separated by at least 100 kb on the first DNA molecule prior to cleaving the first DNA molecule. In some aspects, the method comprises sequencing a second copy of the first DNA molecule.

Disclosed herein are rearranged nucleic acid molecules of at least 5 kb comprising a) a first segment; b) a second segment; and c) a third segment; said first segment and said second segment being joined at a first junction; and said second segment and said third segment being joined at a second junction; wherein said first segment, said second segment and said third segment exist in phase separated by at least 10 kb in an unrearranged nucleic acid molecule, and wherein at least 70% of said rearranged nucleic acid molecule maps to said common unrearranged nucleic acid molecule. In some aspects, the first segment, the second segment and the third segment comprise separate genomic nucleic acid sequence from a common nucleic acid molecule of a genome. In some aspects, the first segment, the second segment and the third segment exist in a common molecule in the genome in an order that is rearranged in the rearranged nucleic acid. In some aspects, said nucleic acid molecule is at least 30 kb in length. In some aspects, said nucleic acid comprises a hairpin loop at a double-stranded terminal end, so that the molecule comprises a single strand comprising a 30 kb inverted repeat. In some aspects, said nucleic acid is a double-stranded circular molecule. In some aspects, at least 80% of said rearranged nucleic acid molecule maps to said common unrearranged nucleic acid molecule. In some aspects, at least 85% of said rearranged nucleic acid molecule maps to said common unrearranged nucleic acid molecule. In some aspects, at least 90% of said rearranged nucleic acid molecule maps to said common unrearranged nucleic acid molecule. In some aspects, at least 95% of said rearranged nucleic acid molecule maps to said common unrearranged nucleic acid molecule. In some aspects, at least 99% of said rearranged nucleic acid molecule maps to said common unrearranged nucleic acid molecule. In some aspects, at least 80% of segments of said rearranged nucleic acid molecule maps to said common unrearranged nucleic acid molecule. In some aspects, at least 85% of segments of said rearranged nucleic acid molecule maps to said common unrearranged nucleic acid molecule. In some aspects, at least 90% of segments of said rearranged nucleic acid molecule maps to said common unrearranged nucleic acid molecule. In some aspects, at least 95% of segments of said rearranged nucleic acid molecule maps to said common unrearranged nucleic acid molecule. In some aspects, at least 99% of segments of said rearranged nucleic acid molecule maps to said common unrearranged nucleic acid molecule. In some aspects, the rearranged nucleic acid is generated by steps of any of the methods disclosed herein.

Disclosed herein are methods of generating a phased sequence of a sample nucleic acid molecule comprising a) generating a first rearranged nucleic acid molecule as disclosed herein from the sample nucleic acid molecule; b) generating a second rearranged nucleic acid molecule as disclosed herein from the sample nucleic acid molecule; and c) sequencing the first rearranged nucleic acid molecule and the second rearranged nucleic acid molecule; wherein the first rearranged nucleic acid molecule and the second rearranged nucleic acid molecule are independently generated Disclosed herein are methods of generating a phased sequence of a sample nucleic acid molecule comprising a) sequencing a first rearranged nucleic acid molecule as disclosed herein from the sample nucleic acid molecule; b) sequencing a second rearranged nucleic acid molecule as disclosed herein from the sample nucleic acid molecule; wherein the first rearranged nucleic acid molecule and the second rearranged nucleic acid molecule are independently generated; and c) assembling sequence of the first rearranged nucleic acid molecule as disclosed herein and the second rearranged nucleic acid molecule as disclosed herein such that an assembled sequence is an unrearranged phased sequence of a sample nucleic acid molecule. In some aspects, sequencing a first rearranged nucleic acid molecule comprises generating a sequence read of at least 1 kb. In some aspects, sequencing a first rearranged nucleic acid molecule comprises generating a sequence read of at least 2 kb. In some aspects, sequencing a first rearranged nucleic acid molecule comprises generating a sequence read of at least 5 kb. In some aspects, the method comprises assigning at least 70% of said first rearranged molecule to a common phase of a single genomic molecule. In some aspects, the method comprises assigning at least 70% of said second rearranged molecule to a common phase of a single genomic molecule. In some aspects, the method comprises assigning at least 80% of said first rearranged molecule to a common phase of a single genomic molecule. In some aspects, the method comprises assigning at least 80% of said second rearranged molecule to a common phase of a single genomic molecule. In some aspects, the method comprises assigning at least 90% of said first rearranged molecule to a common phase of a single genomic molecule. In some aspects, the method comprises assigning at least 90% of said second rearranged molecule to a common phase of a single genomic molecule. In some aspects, the method comprises assigning at least 95% of said first rearranged molecule to a common phase of a single genomic molecule. In some aspects, the method comprises assigning at least 95% of said second rearranged molecule to a common phase of a single genomic molecule.

Disclosed herein are methods of phasing long-read sequence data comprising a) obtaining sequence data from any nucleic acid sample disclosed herein; b) obtaining long-read sequence data from any rearranged nucleic acid as disclosed herein; c) mapping the long-read sequence data from the rearranged nucleic acid to the sequence data from the nucleic acid sample; and d) assigning to a common phase the sequence data from the nucleic acid sample mapped to by the long-read sequence data from the rearranged nucleic acid.

Disclosed herein are methods of providing phase information to a nucleic acid dataset generated from a nucleic acid sample by a DNA sequencing technology, comprising a) obtaining a nucleic acid of said nucleic acid sample having a first segment and a second segment separated by a distance greater than a read length of the DNA sequencing technology; b) shuffling the nucleic acid such that the first segment and the second segment are separated by a distance less than a read length of the DNA sequencing technology; c) sequencing the shuffled nucleic acid using the DNA sequencing technology such that the first segment and the second segment appear in a single read of the DNA sequencing technology; and d) assigning sequence reads of the data set comprising first segment sequence and sequence reads of the data set comprising second segment sequence to a common phase. In some aspects, the DNA sequencing technology generates reads having a read length of at least 10 kb. In some aspects, shuffling comprises performing steps of any methods disclosed herein. In some aspects, the first segment and the second segment are separated by a linker oligo that marks a segment end.

Disclosed herein are nucleic acid sequence databases comprising sequence information obtained from a plurality of molecules as disclosed herein, wherein sequence information corresponding to molecules having less than 70% of their segments map to a common scaffold is excluded from at least one analysis.

Disclosed herein are nucleic acid sequence databases comprising sequence information obtained from a plurality of molecules as disclosed herein, wherein sequence information corresponding to molecules having less than 70% of their sequence information map to a common scaffold is excluded from at least one analysis.

Disclosed herein are methods of phasing long-read sequence data comprising a) obtaining sequence data from any nucleic acid sample disclosed herein; b) obtaining long-read sequence data from the rearranged nucleic acid of any rearranged nucleic acid disclosed herein; c) mapping the first segment, the second segment and the third segment of the rearranged nucleic acid from the sequence data from the nucleic acid sample to the nucleic acid sample sequence data; and d) when at least two segments map to a common scaffold, assigning sequence variation of said segments to a common phase. In some aspects, the first segment comprises a single nucleotide polymorphism relative to the sequence data from the nucleic acid sample. In some aspects, the first segment comprises an insertion relative to the sequence data from the nucleic acid sample. In some aspects, the first segment comprises a deletion relative to the sequence data from the nucleic acid sample. In some aspects, the method comprises assigning a first set of segments mapping to a first common scaffold to a common phase of the first common scaffold, and assigning a second set of segments mapping to a second common scaffold to a common phase of the second common scaffold.

Disclosed herein are nucleic acid sequence libraries of a nucleic acid sample, said nucleic acid sequence library comprising a population of nucleic acid sequence reads having an average read length, at least one of said reads comprising at least 500 bases of a first nucleic acid segment and at least 500 bases of a second nucleic acid segment, wherein said first nucleic acid segment and said second nucleic acid segment are found in phase separated by a distance greater than said average read length on a common molecule of said nucleic acid sample. In some aspects, said first nucleic acid segment and said second nucleic acid segment are found in phase separated by a distance greater than 10 kb. In some aspects, said first nucleic acid segment and said second nucleic acid segment are found in phase separated by a distance greater than 20 kb. In some aspects, said first nucleic acid segment and said second nucleic acid segment are found in phase separated by a distance greater than 50 kb. In some aspects, said first nucleic acid segment and said second nucleic acid segment are found in phase separated by a distance greater than 100 kb. In some aspects, at least one of said reads comprises at least 1 kb of a first nucleic acid segment. In some aspects, at least one of said reads comprises at least 5 kb of a first nucleic acid segment. In some aspects, at least one of said reads comprises at least 10 kb of a first nucleic acid segment. In some aspects, at least one of said reads comprises at least 20 kb of a first nucleic acid segment. In some aspects, at least one of said reads comprises at least 50 kb of a first nucleic acid segment. In some aspects, nucleic acid sequence library comprises at least 80% of said nucleic acid sample. In some aspects, nucleic acid sequence library comprises at least 85% of said nucleic acid sample. In some aspects, nucleic acid sequence library comprises at least 90% of said nucleic acid sample. In some aspects, nucleic acid sequence library comprises at least 95% of said nucleic acid sample. In some aspects, nucleic acid sequence library comprises at least 99% of said nucleic acid sample. In some aspects, nucleic acid sequence library comprises at least 99.9% of said nucleic acid sample.

Disclosed herein are nucleic acid sequence libraries of a nucleic acid sample, said nucleic acid sequence library comprising a population of nucleic acid sequence reads having a mean length of at least 1 kb, said reads independently comprising at least 300 bases of sequence from two separate in phase regions of the nucleic acid sample, said two separate in phase regions separated by a distance greater than 10 kb in the nucleic acid sample. In some aspects, said reads independently comprise at least 500 bases of sequence from two separate in phase regions of the nucleic acid sample. In some aspects, said reads independently comprise at least 1 kb of sequence from two separate in phase regions of the nucleic acid sample. In some aspects, said reads independently comprise at least 2 kb of sequence from two separate in phase regions of the nucleic acid sample. In some aspects, said reads independently comprise at least 5 kb of sequence from two separate in phase regions of the nucleic acid sample. In some aspects, said reads independently comprise at least 10 kb of sequence from two separate in phase regions of the nucleic acid sample. In some aspects, said two separate in phase regions are separated by a distance greater than 20 kb in the nucleic acid sample. In some aspects, said two separate in phase regions are separated by a distance greater than 30 kb in the nucleic acid sample In some aspects, said two separate in phase regions are separated by a distance greater than 50 kb in the nucleic acid sample in at least 1% of the reads. In some aspects, said two separate in phase regions are separated by a distance greater than 100 kb in the nucleic acid sample in at least 1% of the reads. In some aspects, nucleic acid sequence library comprises at least 80% of said nucleic acid sample. In some aspects, nucleic acid sequence library comprises at least 85% of said nucleic acid sample. In some aspects, nucleic acid sequence library comprises at least 90% of said nucleic acid sample. In some aspects, nucleic acid sequence library comprises at least 95% of said nucleic acid sample. In some aspects, nucleic acid sequence library comprises at least 99% of said nucleic acid sample. In some aspects, nucleic acid sequence library comprises at least 99.9% of said nucleic acid sample.

Disclosed herein are nucleic acid libraries generated from a nucleic acid sample, wherein at least 80% of nucleic acid sequence of the nucleic acid sample is represented in the nucleic acid library; and in phase sequence segments of the nucleic acid sample are rearranged such that at least one distantly positioned pair of in phase segments of the nucleic acid sample is read in a single sequence read; such that sequencing said library concurrently generates contig information spanning at least 80% of the nucleic acid sample, and phase information sufficient to order and orient said contig information to generate a phased sequence of said nucleic acid sample. In some aspects, at least 90% of nucleic acid sequence of the nucleic acid sample is represented in the nucleic acid library. In some aspects, at least 95% of nucleic acid sequence of the nucleic acid sample is represented in the nucleic acid library. In some aspects, at least 99% of nucleic acid sequence of the nucleic acid sample is represented in the nucleic acid library. In some aspects, said 80% of nucleic acid sequence of the nucleic acid sample is obtained from no more than 100,000 library constituents. In some aspects, said 80% of nucleic acid sequence of the nucleic acid sample is obtained from no more than 10,000 library constituents. In some aspects, said 80% of nucleic acid sequence of the nucleic acid sample is obtained from no more than 1,000 library constituents. In some aspects, said 80% of nucleic acid sequence of the nucleic acid sample is obtained from no more than 500 library constituents. In some aspects, the sample is a genomic sample. In some aspects, the sample is a eukaryotic genomic sample. In some aspects, the sample is a plant genomic sample. In some aspects, the sample is an animal genomic sample. In some aspects, the sample is a mammalian genomic sample. In some aspects, the sample is a unicellular eukaryotic genomic sample. In some aspects, the sample is a human genomic sample. In some aspects, the nucleic acid library is not barcoded to preserve phase information. In some aspects, a read of said library comprises at least 1 kb of sequence from a first region and at least 100 bases of sequence from a second region in phase the first region and separated by greater than 50 kb from the first region in the sample.

Disclosed herein are methods of configuring a nucleic acid molecule for sequencing on a sequencing device, wherein the nucleic acid molecule comprises at least 100 kb of sequence, and wherein said at least 100 kb of sequence comprises a first segment and a second segment separated by a length greater than a read length of the sequencing device, comprising changing a relative position of the first segment relative to the second segment of the nucleic acid molecule, such that the first segment and the segment are separated by less than the read length of the sequencing device; wherein phase information for the first segment and the second segment is maintained; and wherein no more than 10% of the nucleic acid molecule is deleted. In some aspects, the method comprises generating a read spanning at least part of the first segment and the second segment. In some aspects, the method comprises assigning the first segment and the second segment to a common phase of a sequence of the nucleic acid molecule. In some aspects, no more than 5% of the nucleic acid molecule is deleted. In some aspects, no more than 1% of the nucleic acid molecule is deleted. In some aspects, the first segment and the second segment are separated by at least 10 kb in the nucleic acid molecule prior to configuring. In some aspects, the first segment and the second segment are separated by at least 50 kb in the nucleic acid molecule prior to configuring. In some aspects, the first segment and the second segment are separated by a junction marker following said configuring. In some aspects, the method comprises attaching a stem loop at an end of the nucleic acid, thereby converting the molecule to a single strand. In some aspects, the method comprises circularizing the nucleic acid molecule. In some aspects, the method comprises attaching the nucleic acid molecule to a DNA polymerase. In some aspects, the method comprises binding the nucleic acid molecule such that the first segment and the second segment are held together independent of a phosphodiester backbone; cleaving a phosphodiester backbone between the first segment and the second segment at at least two positions; and reattaching the first segment to the second segment, such that the first segment and the second segment are separated by less than a read length of the sequencing device. In some aspects, said cleaving and said reattaching does not result in loss of sequence information form said nucleic acid molecule.

Disclosed herein are methods of generating long-distance phase information from a first nucleic acid molecule, comprising: a) providing a sample comprising a first nucleic acid molecule having a first segment, a second segment, and a third segment, wherein none of the first segment, the second segment, and the third segment are adjacent on the first nucleic acid molecule, wherein the first nucleic acid molecule is contacted to a framework such that the first segment, the second segment, and the third segment are bound to the framework independent of a common phosphodiester backbone of the first nucleic acid molecule; b) cleaving the first nucleic acid molecule such that the first segment, the second segment, and the third segment are not joined by a common phosphodiester backbone; c) connecting the first segment to the second segment and connecting the second segment to the third segment; and d) sequencing a first portion of the first nucleic acid molecule comprising the first segment, the second segment, and the third segment, thereby generating first segment sequence information, second segment sequence information, and third segment sequence information, wherein the first segment sequence information, the second segment sequence information, and the third segment sequence information provide long-distance phase information about the first nucleic acid molecule. In some aspects, the framework comprises reconstituted chromatin. In some aspects, the framework comprises native chromatin. In some aspects, the cleaving is conducted with a restriction enzyme. In some aspects, the cleaving is conducted with fragmentase. In some aspects, the method comprises, prior to the sequencing, removing from the sample a second portion of the first nucleic acid molecule comprising at most two segments. In some aspects, the method comprises assembling a sequence of the first nucleic acid molecule using the first segment sequence information, the second segment sequence information, and the third segment sequence information.

Disclosed herein are methods of sequencing a nucleic acid molecule, comprising: a) obtaining a first nucleic acid molecule comprising a first segment, a second segment and a third segment sharing a common phosphodiester backbone, wherein none of said first segment, second segment and third segment are adjacent on said first nucleic acid molecule; b) partitioning said nucleic acid molecule such that said first segment, second segment and third segment are associated independent of their common phosphodiester backbone; c) cleaving said nucleic acid molecule to generate fragments such that there is no continuous phosphodiester backbone linking the first segment, second segment and third segment; d) ligating said fragments such that said first segment, second segment and third segment are consecutive on a rearranged nucleic acid molecule sharing a common phosphodiester backbone; and e) sequencing at least a portion of said rearranged nucleic acid molecule such that at least 5,000 bases of said rearranged nucleic acid molecule are sequenced in a single read. In some aspects, partitioning comprises contacting said nucleic acid molecule to a binding moiety such that said first segment, second segment and third segment are bound in a common complex independent of their common phosphodiester backbone. In some aspects, contacting the nucleic acid molecule to a plurality of DNA-binding molecules comprises contacting to a population of DNA-binding proteins. In some aspects, the population of DNA-binding proteins comprises nuclear proteins. In some aspects, the population of DNA-binding proteins comprises nucleosomes. In some aspects, the population of DNA-binding proteins comprises histones. In some aspects, contacting the nucleic acid molecule to a plurality of DNA-binding moieties comprises contacting to a population of DNA-binding nanoparticles. In some aspects, cleaving the nucleic acid molecule comprises contacting to a restriction endonuclease. In some aspects, cleaving the nucleic acid molecule comprises contacting to a nonspecific endonuclease. In some aspects, cleaving the nucleic acid molecule comprises contacting to a tagmentation enzyme. In some aspects, cleaving the nucleic acid molecule comprises contacting to a transposase. In some aspects, cleaving the nucleic acid molecule comprises shearing the first molecule. In some aspects, partitioning comprises separating said nucleic acid molecule from other nucleic acid molecules of a sample. In some aspects, partitioning comprises diluting said nucleic acid sample. In some aspects, partitioning comprises distributing said nucleic acid molecule into a microdroplet of an emulsion.

Disclosed herein are nucleic acid molecules representative of genomic phase information of an organisms's genome, said nucleic acid molecule comprising at least 20 kb of nucleic acid sequence information that maps to a single genomic molecule, wherein said sequence information comprises segments rearranged relative to their position in the genomic molecule, and wherein at least 70% of sequence information that uniquely maps to said organism's genome maps to a single genomic molecule. In some aspects, the nucleic acid molecule comprises at least 20 segments. In some aspects, said segments are not adjacent in said organism's genome.

Disclosed herein are nucleic acid libraries comprising at least 100 nucleic acid molecule constituents of at least 20 kb, wherein constituents comprise rearranged segments of an organism's genome; wherein at least 70% of uniquely mapping segments from a library constituent map to a common genomic molecule; and wherein constituents are not bound to nucleic acid binding moieties.

Disclosed herein are nucleic acid datasets comprising sequences corresponding to at least 100 nucleic acid molecule constituents of at least 20 kb, wherein constituents comprise at least 5 rearranged segments of an organism's genome, and wherein constituents for which less than 70% of said rearranged segments map to a common scaffold are excluded from a downstream analysis.

Disclosed herein are nucleic acid datasets comprising sequences corresponding to at least 100 nucleic acid molecule constituents of at least 20 kb, wherein constituents comprise at least 5 rearranged segments of an organism's genome, and wherein constituents for which less than 70% of said sequence uniquely maps to a common scaffold are excluded from a downstream analysis.

BRIEF DESCRIPTION OF THE DRAWINGS

Novel features of the disclosure are set forth with particularity in the appended claims and in summary and detailed descriptions herein. A better understanding of the features and advantages of the disclosure will be obtained by reference to the following detailed description that sets forth illustrative embodiments, in which the principles of the disclosure are utilized, and the accompanying drawings of which:

DETAILED DESCRIPTION

Figure 1:
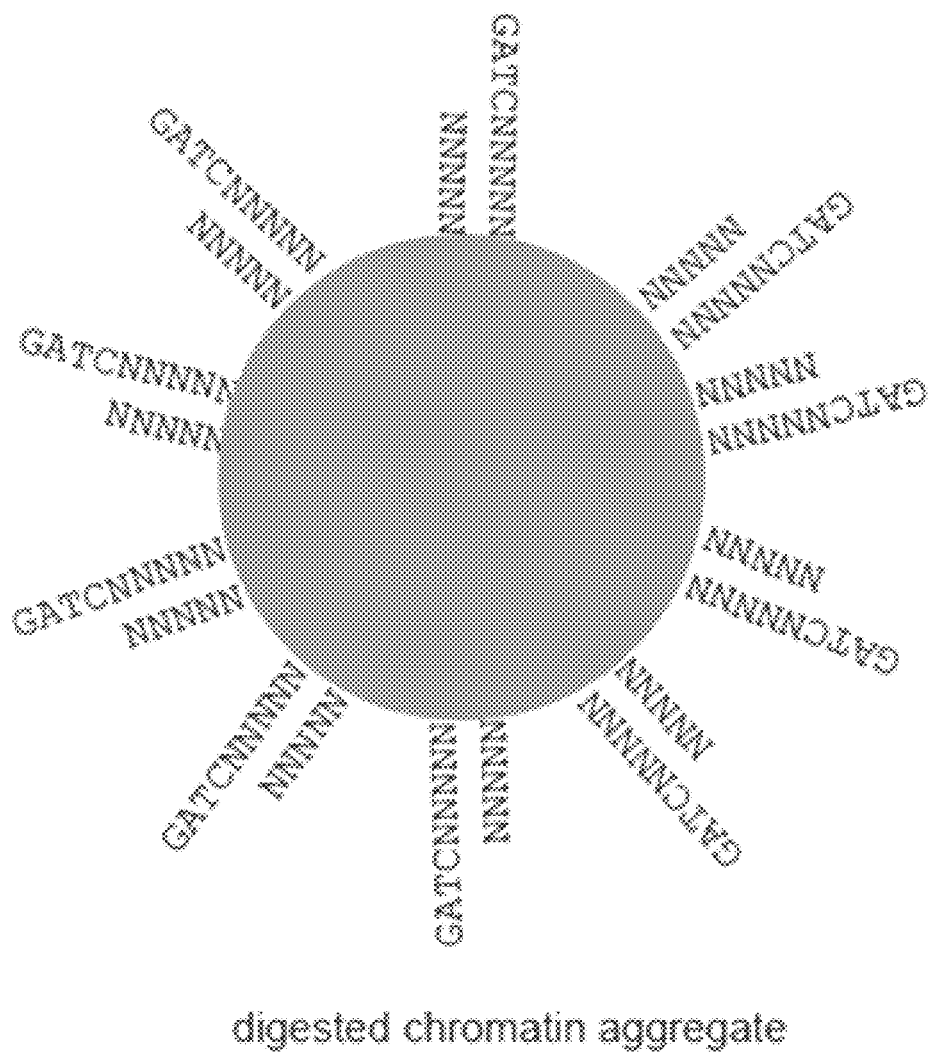
FIG. 1 depicts a digested reconstituted chromatin aggregate with many free ends with single-stranded overhangs that are hybridization compatible with all other free ends.

Disclosed herein are methods for generating read sets, including phased read-sets, for applications including genome assembly and haplotype phasing, using long-read or short-read sequencing technologies. Nucleic acid molecules can be bound (e.g., in a chromatin structure), cleaved to expose internal ends, re-attached at junctions to other exposed ends, freed from binding, and sequenced. This technique can produce nucleic acid molecules comprising multiple sequence segments. The multiple sequence segments within a nucleic acid molecule can have phase information preserved while being rearranged relative to their natural or starting position and orientation. Sequence segments on either side of a junction can be confidently considered to come from the same phase of a sample nucleic acid molecule.

Nucleic acid molecules, including high molecular weight DNA, can be bound or immobilized on at least one nucleic acid binding moiety. For example, DNA assembled into in vitro chromatin aggregates and fixed with formaldehyde treatment are consistent with methods herein. Nucleic acid binding or immobilizing approaches include, but are not limited to, in vitro or reconstituted chromatin assembly, native chromatin, DNA-binding protein aggregates, nanoparticles, DNA-binding beads or beads coated using a DNA-binding substance, polymers, synthetic DNA-binding molecules or other solid or substantially solid affinity molecules. In some cases, the beads are solid phase reversible immobilization (SPRI) beads (e.g., beads with negatively charged carboxyl groups such as Beckman-Coulter Agencourt AMPure XP beads).

Nucleic acids bound to a nucleic acid binding moiety such as those described herein can be held such that a nucleic acid molecule having a first segment and a second segment separated on the nucleic acid molecule by a distance greater than a read distance on a sequencing device (10 kb, 50 kb, 100 kb or greater, for example) are bound together independent of their common phosphodiester bonds. Upon cleavage of such a bound nucleic acid molecule, exposed ends of the first segment and the second segment may ligate to one another. In some cases, the nucleic acid molecules are bound at a concentration such that there is little or no overlap between bound nucleic acid molecules on a solid surface, such that exposed internal ends of cleaved molecules are likely to re-ligate or become reattached only to exposed ends from other segments that were in phase on a common nucleic acid source prior to cleavage. Consequently, a DNA molecule can be cleaved and cleaved exposed internal ends can be re-ligated, for example at random, without loss of phase information.

A bound nucleic acid molecule can be cleaved to expose internal ends through one of any number of enzymatic and non-enzymatic approaches. For example, a nucleic acid molecule can be digested using a restriction enzyme, such as a restriction endonuclease that leaves a single stranded overhang. MboI digest, for example, is suitable for this purpose, although other restriction endonucleases are contemplated. Lists of restriction endonucleases are available, for example, in most molecular biology product catalogues. Other non-limiting techniques for nucleic acid cleavage include using a transposase, tagmentation enzyme complex, topoisomerase, nonspecific endonuclease, DNA repair enzyme, RNA-guided nuclease, fragmentase, or alternate enzyme. Transposase, for example, can be used in combination with unlinked left and right borders to create a sequence-independent break in a nucleic acid that is marked by attachment of transposase-delivered oligonucleotide sequence. Physical means can also be used to generate cleavage, including mechanical means (e.g., sonication, shear), thermal means (e.g., temperature change), or electromagnetic means (e.g., irradiation, such as UV irradiation).

Immobilization of nucleic acids at this stage can keep the cleaved nucleic acid molecule fragments in close physical proximity, such that phase information for the initial molecule is preserved. Exemplary resulting chromatin aggregates from one nucleic acid binding moiety are shown schematically in FIG. 1. A benefit of the fixation, e.g. to chromatin aggregates, is that separate regions of a common nucleic acid molecule can be held together independent of their phosphodiester backbone, such that their phase information is not lost upon cleavage of the phosphodiester backbone. This benefit is also conveyed through alternate scaffolds to which a nucleic acid molecule is attached prior to cleavage.

Figure 2:
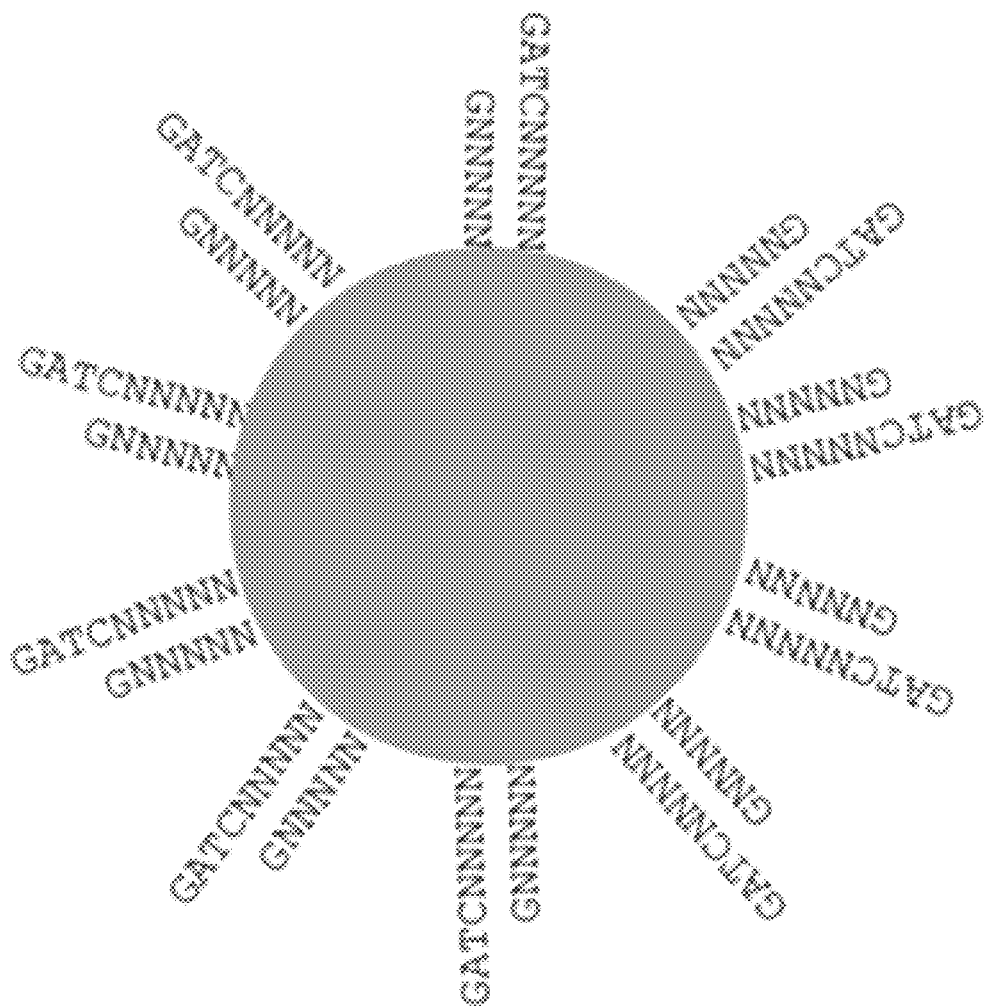
FIG. 2 depicts the digested reconstituted chromatin aggregate of FIG. 1 with a single base filled-in, making each single-stranded overhang incompatible for re-annealing and re-ligation.

Optionally, single stranded "sticky" end overhangs are modified to prevent reannealing and re-ligation. For example, sticky ends are partially filled-in, such as by adding one nucleotide and a polymerase (FIG. 2). In this way, the entire single-stranded end cannot be filled in, but the end is modified to prevent re-ligation with a formerly complementary end. In the example of MboI digestion, which leaves a 5' GATC 5-prime overhang, only the Guanosine nucleotide triphosphate is added. This results in only a "G" fill-in of the first complementary base ("C") and result in a 5' GAT overhang. This step is renders the free sticky ends incompatible for re-ligation to one another, but preserves sticky ends for downstream applications. Alternately, blunt ends are generated through completely filling in the overhangs, restriction digest with blunt-end generating enzymes, treatment with a single-strand DNA exonuclease, or nonspecific cleavage. In some cases, a transposase is used to attach adapter ends having blunt or sticky ends to the exposed internal ends of the DNA molecule.

Figure 3:
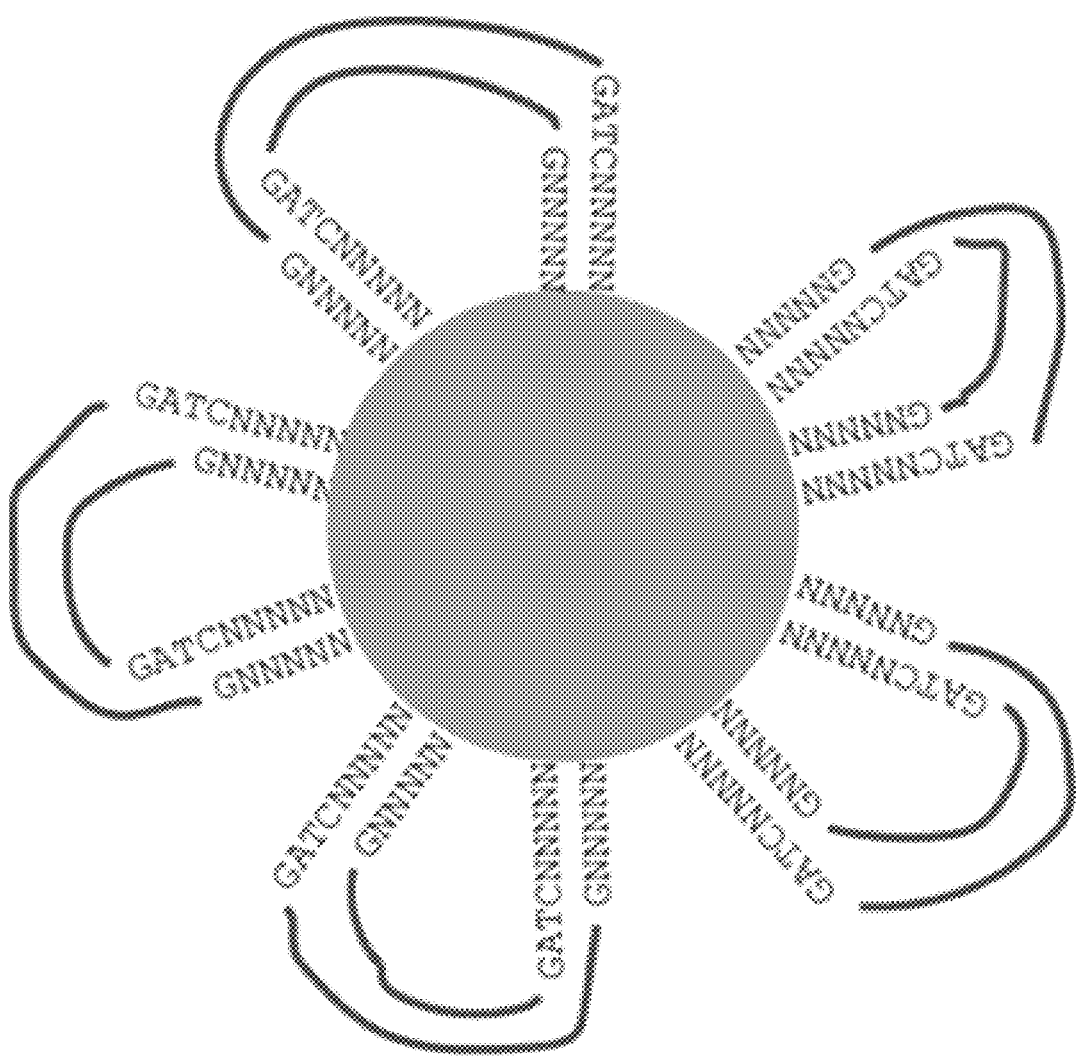
FIG. 3 depicts the partially filled-in digested reconstituted chromatin aggregate of FIG. 2 ligated with punctuation oligonucleotides compatible with the modified free ends of the reconstituted aggregate.

Optionally, a "punctuation oligonucleotide" is introduced (FIG. 3). This punctuation oligonucleotide marks cleavage/re-ligation sites. Some punctuation oligonucleotides have single-stranded overhangs on both ends that are compatible with the partially filled-in overhangs generated on the exposed nucleic acid sample internal ends. An example of a punctuation oligonucleotide is shown below. In some cases, the double-stranded oligonucleotide having single-stranded overhangs is modified, such as by 5' phosphate removal at its 5' ends, so that it cannot form concatemers during ligation.

Alternately, blunt punctuation oligonucleotides are used, or cleavage sites are not marked using a distinct punctuation oligonucleotide. In some systems, such as when a transposase is used, punctuation is accomplished through addition of transpososome border sequences, followed by ligation of border sequences to one another or to a punctuation oligo. An exemplary punctuation oligo is presented below. However, alternate punctuation oligos are consistent with the disclosure herein, varying in sequence, length, overhang presence or sequence, or modification such as 5' de-phosphorylation.

5'ATCACGCGC 3'
3' TGCGCGCTA 5'

In some cases, the double-stranded region of the punctuation oligonucleotide will vary. A relevant feature of the punctuation oligonucleotide is the sequence of its overhang, allowing ligation to the nucleic acid sample but optionally modified precluding auto-ligation or concatemer formation. It is often preferred that the punctuation oligonucleotide comprise sequence that does not occur or is less likely to occur in a target nucleic acid molecule, such that it is easily identified in a downstream sequence reaction. Punctuation oligos are optionally barcoded, for example with a known barcode sequence or with a randomly generated unique identifier sequence. Unique identifier sequences can be designed to make it highly unlikely for multiple junctions in a nucleic acid molecule or in a sample to be barcoded with the same unique identifier.

Cleaved ends can be attached to one another directly or through an oligo (e.g., a punctuation oligo), for example using a ligase or similar enzyme. Ligation can proceed such that the free single-stranded ends of an immobilized high-molecular weight nucleic acid molecule are ligated directly or to the punctuation oligonucleotide (FIG. 3). Because the punctuation oligonucleotide, if utilized, can have two ligatable ends, this ligation can effectively chain regions of the high molecular weight nucleic acid molecule together. Alternative approaches resulting in affixing a punctuating sequence or molecule between two exposed ends can also be employed, as can approaches for directly connecting two exposed ends without punctuation.

Nucleic acids can then be liberated from the nucleic acid binding moiety. In the case of in vitro chromatin aggregates, this can be accomplished by reversing the cross-links, or digesting the protein components, or both reversing the crosslinking and digesting protein components. A suitable approach is treatment of complexes with proteinase K, though many alternatives are also contemplated. For other binding techniques, suitable methods can be employed, such as the severing of linker molecules or the degradation of a substrate.

Nucleic acid molecules resulting from such techniques can have a variety of relevant features. Sequence segments within a nucleic acid molecule can be rearranged relative to their natural or starting positions and orientations, but with phase information preserved. Consequently, sequence segments on either side of a junction can be confidently assigned to a common phase of a common sample molecule. Thus, segments far removed from one another on a molecule can be, by such techniques, brought together or in proximity such that portions or the entirety of each segment is sequenced in a single run of a single molecule sequencing device, allowing definitive phase assignment. Alternately, in some cases originally adjacent segments can become separated from one in the resultant nucleic acid. In some cases, the nucleic acid molecules can be re-ligated such that at least about 50%, 55%, 60%, 65%, 70%, 75%, 80%, 85%, 90%, 91%, 92%, 93%, 94%, 95%, 96%, 97%, 98%, 99%, 99.9%, 99.99%, 99.999%, or 100% of re-ligations are between segments that were in phase on a common nucleic acid source prior to cleavage.

Another relevant feature of the resultant molecules is that, in some cases, most or all the original molecular sequence is preserved, though perhaps rearranged, in the final punctuated or rearranged molecule. For example, in some cases no more than 1%, 2%, 3%, 4%, 5%, 10%, 15%, or 20% of the original molecule is lost in producing the resultant molecule or molecules. Consequently, in addition to being useful as a phase determinant, the resultant molecule retains a substantial proportion of the original molecule sequence, such that the resultant molecule is optionally used to concurrently generate sequence information such as contig information useful in de novo sequencing or as independent verification of previously generated contig information.

Another feature of libraries of some resultant molecules is that cleavage junctions are not common to multiple members of a population of resultant molecules. That is, that different copies of the same starting nucleic acid molecule can end up with different patterns of junction and rearrangement. Random cleavage junctions can be generated with a non-specific cleavage molecule, or through variation in restriction endonuclease selection or digestion parameters.

A consequence of having molecule-specific cleavage sites is that in some cases punctuation oligonucleotides are optionally excluded from the process that results in the 'punctuation molecule' re-shuffling and re-ligation to no ill effect. By aligning segments of three or more reshuffled molecules, one observes that cleavage sites are readily identified by their absence in the majority of other members of a library. That is, when three or more reshuffled molecules are locally aligned, a segment can be found to be common to all of the molecules, but the edges of the segment can vary among the molecules. By noting where segment local sequence similarity ends, one can map cleavage junctions in an 'unpunctuated' rearranged nucleic acid molecule.

The resulting nucleic acid molecules (see, e.g., FIG. 4) can be sequenced, for example on a long-read sequencer. The resulting sequence reads contain segments that alternate between nucleic acid sequence from the original input molecule and, if they are used, sequences of the punctuation oligo. These reads can be processed by a computer to split sequence data from each read using the punctuation oligonucleotide sequence, or are otherwise processed to identify junctions. The sequence segments within each read can be segments from a single input high molecular weight DNA molecule. The original nucleic acid molecule can comprise a genome sequence or fraction thereof, such as a chromosome. The sets of segment reads can be discontinuous in the original nucleic acid molecule but reveal long-range, haplotype-phased data. These data can be used for de novo genome assembly and phasing heterozygous positions in the input genome. Sequence between junctions indicates contiguous nucleic acid sequence in the source nucleic acid sample, while sequence across a junction is indicative of a nucleic acid segment that is in phase in the nucleic acid sample but that may be far removed in the arranged scaffold from the adjacent segment.

Junctions can be identified by a variety of approaches. If punctuation oligos are used, junctions can be identified at reads containing the punctuation oligo sequence. Alternately, junctions can be identified by comparison to a second sequence source (and, preferably, a third sequence source) for a nucleic acid molecule, such as a previously generated contig sequence dataset or a second, independently generated DNA chain molecule having independently derived junctions. As the sequence is aligned, for example, the quality or confidence of alignment to a particular location can indicate where one segment ends and another begins. If restriction enzymes are used to generate cleavages, sequences containing the restriction enzyme recognition site can be evaluated for potentially containing a junction. Note that not every restriction enzyme recognition site may contain a junction, as some restriction enzyme recognition sites may not have been physically accessible by the enzyme while the nucleic acid was bound to the support, for example. Statistical information can also be employed in identifying junctions; for example, the length segments between junctions may be predicted to be of a certain average value or to follow a certain distribution.

A benefit of the manipulations herein is that they can preserve molecular phase information while bringing nonadjacent regions of the molecule in proximity such that they are included in a single nucleic acid molecule at a distance suitable for sequencing in a single read, such as a long read. Thus, regions that are separated in the starting sample by greater than the distance of a single long read operation (for example 10 kb, 15 kb, 20 kb, 30 kb, 50 kb, 100 kb or greater) are brought into local proximity such that they are within the distance covered by a single read of a long-range sequencing reaction. Thus, regions that are separated by more than the range of the sequencing technology for a single read in the original sample are read in a single reaction in the phase-preserved, rearranged molecule.

Resultant rearranged molecules can be sequenced and their sequence information mapped to independently or concurrently generated sequence reads or contig information, or to a known reference genome sequence (for example, the known sequence of the human genome). Segments adjacent on the resultant rearranged molecule reads are presumed to be in phase. Accordingly, when these segments are mapped to disparate contigs or long range sequence reads, the reads are assigned to a common phase of a common molecule in the sequence assembly.

Alternately, if multiple independently generated resultant rearranged molecules are sequenced concurrently, phased sample data is optionally generated from these molecules alone, such that segment sequences separated by junctions are inferred to be in phase, while sequences not separated by junctions are inferred to represent stretches of nucleic acids contiguous in the sample itself and useful for, for example, de novo sequence determination as well as being useful for phase determination. However, additionally or as an alternative, multiple independently generated resultant rearranged molecules sequenced concurrently can still be compared to independently generated scaffold or contig information Methods and compositions presented herein can preserve long-range phase information, particularly for molecule segments separated by greater than the length of a read in a sequencing technology (10 kb, 20 kb, 50 kb, 100 kb, 500 kb or greater, for example), while providing such nonadjacent segments in a rearranged or often 'punctuated' molecule where the segments are adjacent or close enough to be covered by a single read.

In some instances, resultant rearranged molecules are combined with native molecules for sequencing. The native molecules can be recognized and utilized informatically by the lack of punctuation sequences, if employed. Native molecules are sequenced using short or long read technology, and their assembly is guided by the phase information and segment sequence information generated through sequencing of the rearranged molecule or library.

Nucleic Acid Extraction

Methods for the extraction and purification of nucleic acids suitable for use with the disclosure herein are well known in the art. For example, nucleic acids are purified by organic extraction with phenol, phenol/chloroform/isoamyl alcohol, or similar formulations, including TRIzol and Tri-Reagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles to which nucleic acids specifically or non-specifically bind, followed by isolation of the beads using a magnet, and washing and eluting the nucleic acids from the beads (see e.g. U.S. Pat. No. 5,705,628). In some embodiments, the above isolation methods may be preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic acid isolation step, purification of nucleic acids can be performed after any step in the methods of the disclosure, such as to remove excess or unwanted reagents, reactants, or products.

Nucleic acid template molecules can be obtained as described, for example, in U.S. Patent Application Publication Number US2002/0190663 A1, published Oct. 9, 2003. Generally, nucleic acids are extracted from a biological sample by a variety of techniques such as those described by Maniatis, et al., Molecular Cloning: A Laboratory Manual, Cold Spring Harbor, N.Y., pp. 280-281 (1982, which is herein incorporated by reference in its entirety). In some cases, the nucleic acids can be first extract from the biological samples and then cross-linked in vitro. In some cases, native association proteins (e.g. histones) can be further removed from the nucleic acids. In some embodiments, the disclosure is easily applied to any high molecular weight double stranded DNA including, for example, DNA isolated from tissues, cell culture, bodily fluids, animal tissue, plant, bacteria, fungi, or viruses.

In some embodiments, nucleic acid template molecules (e.g., DNA or RNA) are isolated from a biological sample containing a variety of other components, such as proteins, lipids, and non-template nucleic acids. Nucleic acid template molecules can be obtained from any cellular material, obtained from an animal, plant, bacterium, fungus, or any other cellular organism or virus, or may be artificially synthesized. Biological samples for use in the present disclosure include viral particles or preparations. Nucleic acid template molecules can be obtained directly from an organism or from a biological sample obtained from an organism, e.g., from blood, urine, cerebrospinal fluid, seminal fluid, saliva, sputum, stool and tissue. Any tissue or body fluid specimen may be a source for nucleic acids of the present disclosure. Nucleic acid template molecules can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA. A sample may also comprise isolated DNA from a non-cellular origin, e.g. amplified/isolated DNA from the freezer.

Nucleic acid molecules, including high molecular weight DNA, can be bound or immobilized on a nucleic acid binding moiety. For example, DNA assembled into in vitro chromatin aggregates and fixed with formaldehyde treatment are consistent with methods herein. Nucleic acid binding or immobilizing approaches include, but are not limited to, in vitro or reconstituted chromatin assembly, native chromatin, DNA-binding protein aggregates, nanoparticles, DNA-binding beads or beads coated using a DNA-binding substance, polymers, synthetic DNA-binding molecules or other solid or substantially solid affinity molecules. In some cases, the beads are solid phase reversible immobilization (SPRI) beads (e.g., beads with negatively charged carboxyl groups such as Beckman-Coulter Agencourt AMPure XP beads).

Nucleic acids, such as those bound to a nucleic acid binding moiety such as those described herein, can be held such that a nucleic acid molecule having a first segment and a second segment separated on the nucleic acid molecule by a distance greater than a read distance on a sequencing device (10 kb, 50 kb, 100 kb or greater, for example) are bound together independent of their common phosphodiester bonds. Upon cleavage of such a bound nucleic acid molecule, exposed ends of the first segment and the second segment may ligate to one another. In some cases, the nucleic acid molecules are bound at a concentration such that there is little or no overlap between bound nucleic acid molecules on a solid surface, such that exposed internal ends of cleaved molecules are likely to re-ligate or become reattached only to exposed ends from other segments that were in phase on a common nucleic acid source prior to cleavage. Consequently, a DNA molecule can be cleaved and cleaved exposed internal ends can be re-ligated, for example at random, without loss of phase information. In some cases, the nucleic acid molecules can be re-ligated such that at least about 50%, 55%, 60%, 65%, 70%, 75%, 80%, 85%, 90%, 91%, 92%, 93%, 94%, 95%, 96%, 97%, 98%, 99%, 99.9%, 99.99%, 99.999%, or 100% of re-ligations are between segments that were in phase on a common nucleic acid source prior to cleavage.

In some cases, the surface density of bound nucleic acids on a surface is controlled through the amount of surface area made available for binding. For example, selecting the size of a bead used for binding nucleic acids can affect or control the distance between nucleic acids, or the average surface density of bound nucleic acids. A larger bead surface can result in a greater distance between bound nucleic acids. This can result in a reduced rate of intermolecular ligation events between nucleic acids or nucleic acid complexes. The beads used can be about 100 nanometers (nm), 200 nm, 300 nm, 400 nm, 500 nm, 600 nm, 700 nm, 800 nm, 900 nm, 1 micrometer (μm), 1.1 μm, 1.2 μm, 1.3 μm, 1.4 μm, 1.5 μm, 1.6 μm, 1.7 μm, 1.8 μm, 1.9 μm, 2 m, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 21 μm, 22 μm, 23 μm, 24 μm, 25 μm, 26 μm, 27 μm, 28 m, 29 μm, 30 μm, 31 μm, 32 μm, 33 μm, 34 μm, 35 μm, 36 μm, 37 μm, 38 μm, 39 μm, 40 μm, 41 μm, 42 μm, 43 μm, 44 μm, 45 μm, 46 μm, 47 μm, 48 μm, 49 μm, 50 μm, 55 μm, 60 μm, 65 m, 70 μm, 75 μm, 80 μm, 85 μm, 90 μm, 95 μm, 100 μm, 200 μm, 300 μm, 400 μm, 500 μm, 600 μm, 700 μm, 800 μm, 900 μm, or 1 millimeter (mm) in diameter. The beads used can be at least about 100 nanometers (nm), 200 nm, 300 nm, 400 nm, 500 nm, 600 nm, 700 nm, 800 nm, 900 nm, 1 micrometer (m), 1.1 μm, 1.2 μm, 1.3 μm, 1.4 μm, 1.5 μm, 1.6 μm, 1.7 μm, 1.8 μm, 1.9 μm, 2 μm, 3 μm, 4 μm, 5 μm, 6 μm, 7 μm, 8 μm, 9 μm, 10 μm, 11 μm, 12 μm, 13 μm, 14 m, 15 μm, 16 μm, 17 μm, 18 μm, 19 μm, 20 μm, 21 μm, 22 μm, 23 μm, 24 μm, 25 μm, 26 μm, 27 μm, 28 μm, 29 μm, 30 μm, 31 μm, 32 μm, 33 μm, 34 μm, 35 μm, 36 μm, 37 μm, 38 μm, 39 m, 40 μm, 41 μm, 42 μm, 43 μm, 44 μm, 45 μm, 46 μm, 47 μm, 48 μm, 49 μm, 50 μm, 55 μm, 60 μm, 65 μm, 70 μm, 75 μm, 80 μm, 85 μm, 90 μm, 95 μm, 100 μm, 200 μm, 300 μm, 400 μm, 500 μm, 600 μm, 700 μm, 800 μm, 900 μm, or 1 millimeter (mm) in diameter. The beads used can be at most about 100 nanometers (nm), 200 nm, 300 nm, 400 nm, 500 nm, 600 nm, 700 nm, 800 nm, 900 nm, 1 micrometer (m), 1.1 μm, 1.2 μm, 1.3 μm, 1.4 μm, 1.5 μm, 1.6 μm, 1.7 μm, 1.8 μm, 1.9 μm, 2 μm, 3 μm, 4 μm, 5 μm, 6 μm, 7 μm, 8 μm, 9 μm, 10 μm, 11 μm, 12 μm, 13 m, 14 μm, 15 μm, 16 μm, 17 μm, 18 μm, 19 μm, 20 μm, 21 μm, 22 μm, 23 μm, 24 μm, 25 μm, 26 μm, 27 μm, 28 μm, 29 μm, 30 μm, 31 μm, 32 μm, 33 μm, 34 μm, 35 μm, 36 μm, 37 μm, 38 m, 39 μm, 40 μm, 41 μm, 42 μm, 43 μm, 44 μm, 45 μm, 46 μm, 47 μm, 48 μm, 49 μm, 50 μm, 55 μm, 60 μm, 65 μm, 70 μm, 75 μm, 80 μm, 85 μm, 90 μm, 95 μm, 100 μm, 200 μm, 300 μm, 400 μm, 500 μm, 600 μm, 700 μm, 800 μm, 900 μm, or 1 millimeter (mm) in diameter.

Nucleic Acid Binding Moiety Complex Formation

A nucleic acid can be bound to a nucleic acid binding moiety to preserve phase information after cleavage of the nucleic acid molecule. Many nucleic acid binding moieties form scaffolds consistent with the disclosure herein. Some suitable with the disclosure herein bind a nucleic acid at multiple points such that phase information is not lost upon cleavage and re-ligation of the nucleic acid molecule.

In some cases, the nucleic acid binding moiety is or comprises a category of protein, such as histones that form chromatin. The chromatin can be reconstituted chromatin or native chromatin. In some cases, the nucleic acid binding moiety is distributed on solid support such as a microarray, a slide, a chip, a microwell, a column, a tube, a particle or a bead. In some examples, the solid support is coated with streptavidin and/or avidin. In other examples, the solid support is coated with an antibody. Further, the solid support can additionally or alternatively comprise a glass, metal, ceramic or polymeric material. In some embodiments, the solid support is a nucleic acid microarray (e.g. a DNA microarray). In other embodiments, the solid support can be a paramagnetic bead.

In some cases, the DNA sample is cross-linked to a plurality of association molecules. In various cases, the association molecules comprise amino acids. In many cases, the association molecules comprise peptides or proteins. In further cases, the association molecules comprise histones. In other cases, the association molecules comprise nanoparticles. In some cases, the nanoparticle is a platinum-based nanoparticle. In other cases, the nanoparticle is a DNA intercalator, or any derivatives thereof. In further cases, the nanoparticle is a bisintercalator, or any derivatives thereof. In certain cases, the association molecules are from a different source than the first DNA molecule. The cross-linking can be conducted as part of a protocol as disclosed herein, or can have been conducted previously. For example, previously fixed samples (e.g., formalin-fixed paraffin-embedded (FFPE)) samples can be processed and analyzed with techniques of the present disclosure.

An example of a nucleic acid binding moiety that forms a structure is reconstituted chromatin. Reconstituted chromatin is differentiated from chromatin formed within a cell/organism over various features. First, reconstituted chromatin is generated in some cases from isolated naked DNA. For many samples, the collection of naked DNA samples is achieved by using any one of a variety of noninvasive to invasive methods, such as by collecting bodily fluids, swabbing buccal or rectal areas, taking epithelial samples, etc. These approaches are generally easier, faster, and less expensive than isolation of native chromatin.

Second, reconstituting chromatin substantially reduces the formation of inter-chromosomal and other long-range interactions that generate artifacts for genome assembly and haplotype phasing. In some cases, a sample has less than about 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0.5, 0.4, 0.3, 0.2, 0.1, 0.01, 0.001% or less inter-chromosomal or intermolecular crosslinking according to the methods and compositions of the disclosure. In some examples, the sample has less than about 30% inter-chromosomal or intermolecular crosslinking. In some examples, the sample has less than about 25% inter-chromosomal or intermolecular crosslinking. In some examples, the sample has less than about 20% inter-chromosomal or intermolecular crosslinking. In some examples, the sample has less than about 15% inter-chromosomal or intermolecular crosslinking. In some examples, the sample has less than about 10% inter-chromosomal or intermolecular crosslinking. In some examples, the sample has less than about 5% inter-chromosomal or intermolecular crosslinking. In some examples, the sample may have less than about 3% inter-chromosomal or intermolecular crosslinking. In further examples, may have less than about 1% inter-chromosomal or intermolecular crosslinking. As inter-chromosomal interactions represent interactions between molecular sections that are not in phase, their reduction or elimination is beneficial to some goals of the present disclosure, that is, the efficient, rapid assembly of phased nucleic acid information.

Third, the frequency of sites that are capable of crosslinking and thus the frequency of intramolecular crosslinks within the polynucleotide is adjustable. For example, the ratio of DNA to histones can be varied, such that the nucleosome density can be adjusted to a desired value. In some cases, the nucleosome density is reduced below the physiological level. Accordingly, the distribution of crosslinks can be altered to favor longer-range interactions. In some embodiments, sub-samples with varying cross-linking density may be prepared to cover both short- and long-range associations.

For example, the crosslinking conditions can be adjusted such that at least about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 40%, about 45%, about 50%, about 60%, about 70%, about 80%, about 90%, about 95%, or about 100% of the crosslinks so as to join DNA segments that are at least about 50 kb, about 60 kb, about 70 kb, about 80 kb, about 90 kb, about 100 kb, about 110 kb, about 120 kb, about 130 kb, about 140 kb, about 150 kb, about 160 kb, about 180 kb, about 200 kb, about 250 kb, about 300 kb, about 350 kb, about 400 kb, about 450 kb, or about 500 kb apart on a sample DNA molecule.

An important benefit of a nucleic acid binding moiety scaffold such as reconstituted chromatin is that it preserves physical linkage information of its constituent nucleic acids independent of their phosphodiester bonds. Accordingly, nucleic acids held together by reconstituted chromatin, optionally crosslinked to maintain stability, will maintain their proximity even if their phosphodiester bonds are broken, as may occur in internal labeling. Because of the reconstituted chromatin, the fragments will remain in proximity even though cleaved, thereby preserving phase or physical linkage information during an internal labeling process. Thus, when the exposed ends are re-ligated, they will ligate to segments derived from a common phase of a common molecule.

Reconstituted Chromatin Assembly

The assembly of nucleic acids onto a nucleic acid binding moiety for the preservation of phase information during cleavage and rearrangement of the nucleic acid molecule is accomplished in some cases through the assembly of reconstituted chromatin onto a nucleic acid sample. Reconstituted chromatin as used herein is used broadly, ranging from reassembly of native chromatin constituents onto a nucleic acid, to binding of a nucleic acid to non-biological particles.

Referring to reconstituted chromatin in a traditional sense, assembly of core histones and DNA into nucleosomes is mediated by chaperone proteins and associated assembly factors. Nearly all these factors are core histone-binding proteins. Some of the histone chaperones, such as nucleosome assembly protein-1 (NAP-1), exhibit a preference for binding to histones H3 and H4. It has also been observed that newly synthesized histones are acetylated and then subsequently deacetylated after assembly into chromatin. The factors that mediate histone acetylation or deacetylation therefore play an important role in the chromatin assembly process.

In general, two in vitro methods have been developed for reconstituting or assembling chromatin, although variations on these methods are contemplated. One set of methods involves ATP-independent assembly, while a second set of methods is ATP-dependent.

The ATP-independent methods for reconstituting chromatin involve the DNA and core histones plus either a protein like NAP-1 or salt to act as a histone chaperone. This method results in a random arrangement of histones on the DNA that does not accurately mimic the native core nucleosome particle in the cell. These particles are often referred to as mononucleosomes because they are not regularly ordered, extended nucleosome arrays and the DNA sequence used is usually not longer than 250 bp (Kundu, T. K. et al., Mol. Cell 6: 551-561, 2000). To generate an extended array of ordered nucleosomes on a greater length of DNA sequence, the chromatin must be assembled through an ATP-dependent process.

The ATP-dependent assembly of periodic nucleosome arrays, which are similar to those seen in native chromatin, requires the DNA sequence, core histone particles, a chaperone protein, and ATP-utilizing chromatin assembly factors. ACF (ATP-utilizing chromatin assembly and remodeling factor) or RSF (remodeling and spacing factor) are two widely researched assembly factors that are used to generate extended ordered arrays of nucleosomes into chromatin in vitro (Fyodorov, D. V., and Kadonaga, J. T. Method Enzymol. 371: 499-515, 2003; Kundu, T. K. et al. Mol. Cell 6: 551-561, 2000).

Alternate assembly approaches, for example approaches that do not rely upon histones to constitute reconstituted chromatin, are also contemplated. Any DNA binding moiety can be added to a nucleic acid to form some types of reconstituted chromatin broadly defined.

In some embodiments, non-natural chromatin analogs are contemplated. Nanoparticles, such as nanoparticles having a positively coated outer surface to facilitate nucleic acid binding, or a surface activatable for cross-linking to nucleic acids, or both a positively coated outer surface to facilitate nucleic acid binding and a surface activatable for cross-linking to nucleic acids, are contemplated herein. In some embodiments, nanoparticles comprise silicon.

In some cases, the methods disclosed herein are used with DNA associated with nanoparticles. In some instances, the nanoparticles are positively charged. For example, the nanoparticles are coated with amine groups, and/or amine-containing molecules. The DNA and the nanoparticles aggregate and condense, similar to native or reconstituted chromatin. Further, the nanoparticle-bound DNA is induced to aggregate in a fashion that mimics the ordered arrays of biological nucleosomes (i.e. chromatin). The nanoparticle-based method can be less expensive, faster to assemble, provides a better recovery rate than using reconstituted chromatin, and/or allows for reduced DNA input requirements.

A number of factors can be varied to influence the extent and form of condensation including the concentration of nanoparticles in solution, the ratio of nanoparticles to DNA, and the size of nanoparticles used. In some cases, the nanoparticles are added to the DNA at a concentration greater than about 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 15 ng/mL, 20 ng/mL, 25 ng/mL, 30 ng/mL, 40 ng/mL, 50 ng/mL, 60 ng/mL, 70 ng/mL, 80 ng/mL, 90 ng/mL, 100 ng/mL, 120 ng/mL, 140 ng/mL, 160 ng/mL, 180 ng/mL, 200 ng/mL, 250 ng/mL, 300 ng/mL, 400 ng/mL, 500 ng/mL, 600 ng/mL, 700 ng/mL, 800 ng/mL, 900 ng/mL, 1 ng/mL, 2 ng/mL, 3 ng/mL, 4 ng/mL, 5 ng/mL, 6 ng/mL, 7 µg/mL, 8 µg/mL, 9 µg/mL, 10 µg/mL, 15 µg/mL, 20 µg/mL, 25 µg/mL, 30 µg/mL, 40 µg/mL, 50 µg/mL, 60 µg/mL, 70 µg/mL, 80 µg/mL, 90 µg/mL, 100 µg/mL, 120 µg/mL, 140 µg/mL, 160 µg/mL, 180 µg/mL, 200 µg/mL, 250 µg/mL, 300 µg/mL, 400 µg/mL, 500 µg/mL, 600 µg/mL, 700 µg/mL, 800 µg/mL, 900 µg/mL, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 15 mg/mL, 20 mg/mL, 25 mg/mL, 30 mg/mL, 40 mg/mL, 50 mg/mL, 60 mg/mL, 70 mg/mL, 80 mg/mL, 90 mg/mL, or 100 mg/mL. In some cases, the nanoparticles are added to the DNA at a concentration less than about 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 15 ng/mL, 20 ng/mL, 25 ng/mL, 30 ng/mL, 40 ng/mL, 50 ng/mL, 60 ng/mL, 70 ng/mL, 80 ng/mL, 90 ng/mL, 100 ng/mL, 120 ng/mL, 140 ng/mL, 160 ng/mL, 180 ng/mL, 200 ng/mL, 250 ng/mL, 300 ng/mL, 400 ng/mL, 500 ng/mL, 600 ng/mL, 700 ng/mL, 800 ng/mL, 900 ng/mL, 1 µg/mL, 2 µg/mL, 3 µg/mL, 4 µg/mL, 5 µg/mL, 6 µg/mL, 7 µg/mL, 8 µg/mL, 9 µg/mL, 10 µg/mL, 15 µg/mL, 20 µg/mL, 25 µg/mL, 30 µg/mL, 40 µg/mL, 50 µg/mL, 60 µg/mL, 70 µg/mL, 80 µg/mL, 90 µg/mL, 100 µg/mL, 120 µg/mL, 140 µg/mL, 160 µg/mL, 180 µg/mL, 200 µg/mL, 250 µg/mL, 300 µg/mL, 400 µg/mL, 500 µg/mL, 600 µg/mL, 700 µg/mL, 800 µg/mL, 900 µg/mL, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 15 mg/mL, 20 mg/mL, 25 mg/mL, 30 mg/mL, 40 mg/mL, 50 mg/mL, 60 mg/mL, 70 mg/mL, 80 mg/mL, 90 mg/mL, or 100 mg/mL. In some cases, the nanoparticles are added to the DNA at a weight-to-weight (w/w) ratio greater than about 1:10000, 1:5000, 1:2000, 1:1000, 1:500, 1:200, 1:100, 1:50, 1:20, 1:10, 1:5, 1:2, 1:1, 2:1, 5:1, 10:1, 20:1, 50:1, 100:1, 200:1, 500:1, 1000:1, 2000:1, 5000:1, or 10000:1. In some cases, the nanoparticles are added to the DNA at a weight-to-weight (w/w) ratio less than about 1:10000, 1:5000, 1:2000, 1:1000, 1:500, 1:200, 1:100, 1:50, 1:20, 1:10, 1:5, 1:2, 1:1, 2:1, 5:1, 10:1, 20:1, 50:1, 100:1, 200:1, 500:1, 1000:1, 2000:1, 5000:1, or 10000:1. In some cases, the nanoparticles have a diameter greater than about 1 nm 1 nm, 2 nm, 3 nm, 4 nm, 5 nm, 6 nm, 7 nm, 8 nm, 9 nm, 10 nm, 15 nm, 20 nm, 25 nm, 30 nm, 40 nm, 50 nm, 60 nm, 70 nm, 80 nm, 90 nm, 100 nm, 120 nm, 140 nm, 160 nm, 180 nm, 200 nm, 250 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, 10 µm, 15 µm, 20 µm, 25 µm, 30 µm, 40 µm, 50 µm, 60 µm, 70 µm, 80 µm, 90 µm, or 100 µm. In some cases, the nanoparticles have a diameter less than about 1 nm 1 nm, 2 nm, 3 nm, 4 nm, 5 nm, 6 nm, 7 nm, 8 nm, 9 nm, 10 nm, 15 nm, 20 nm, 25 nm, 30 nm, 40 nm, 50 nm, 60 nm, 70 nm, 80 nm, 90 nm, 100 nm, 120 nm, 140 nm, 160 nm, 180 nm, 200 nm, 250 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, 10 µm, 15 µm, 20 µm, 25 µm, 30 µm, 40 µm, 50 µm, 60 µm, 70 µm, 80 µm, 90 µm, or 100 µm.

Furthermore, the nanoparticles may be immobilized on solid substrates (e.g. beads, slides, or tube walls) by applying magnetic fields (in the case of paramagnetic nanoparticles) or by covalent attachment (e.g. by cross-linking to poly-lysine coated substrate). Immobilization of the nanoparticles may improve the ligation efficiency thereby increasing the number of desired products (signal) relative to undesired (noise).

Reconstituted chromatin is optionally contacted to a crosslinking agent such as formaldehyde to further stabilize the DNA-chromatin complex.

Nucleic Acid Cleavage

Bound nucleic acids can be treated to expose internal double-strand ends. Cleavage can be conducted with restriction enzymes, such as restriction endonucleases. Alternative cleavage approaches are also consistent with the disclosure herein. For example, a transposase is optionally used in combination with unlinked left and right border oligonucleic acid molecules so as to create a sequence-independent break in a nucleic acid that is marked by the attachment of the transposase-delivered oligonucleic acid molecules. The oligonucleic acid molecules are synthesized in some cases to comprise punctuation-compatible overhangs, or to be compatible with one another, such that the oligonucleic acid molecules are ligated to one another and serve as the punctuation molecules. A benefit of this type of alternative approach is that cleavage is sequence independent, and thus more likely to vary from one copy of a nucleic acid to another, even if the sequence of two nucleic acid molecules is locally identical.

In some cases, the exposed nucleic acid ends are desirably sticky ends, for example as results from contacting to a restriction endonuclease. In some cases, a restriction endonuclease is used to cleave a predictable overhang, followed by ligation with a nucleic acid end (such as a punctuation oligonucleotide) comprising an overhang complementary to the predictable overhang on a DNA fragment. In some embodiments, the 5' and/or 3' end of a restriction endonuclease-generated overhang is partially filled in. In some cases, the overhang is filled in with a single nucleotide.

In some instances, DNA fragments having an overhang can be joined to one or more nucleic acids, such as punctuation oligonucleotides, oligonucleotides, adapter oligonucleotides, or polynucleotides, having a complementary overhang, such as in a ligation reaction. For example, a single adenine is added to the 3' ends of end repaired DNA fragments using a template independent polymerase, followed by ligation to one or more punctuation oligonucleotides each having a thymine at a 3' end. In some embodiments, nucleic acids, such as oligonucleotides or polynucleotides are joined to blunt end double-stranded DNA molecules which have been modified by extension of the 3' end with one or more nucleotides followed by 5' phosphorylation. In some cases, extension of the 3' end is performed with a polymerase such as, Klenow polymerase or any of the suitable polymerases provided herein, or by use of a terminal deoxynucleotide transferase, in the presence of one or more dNTPs in a suitable buffer that contains magnesium. In some embodiments, target polynucleotides having blunt ends are joined to one or more adapters comprising a blunt end. Phosphorylation of 5' ends of DNA fragment molecules may be performed for example with T4 polynucleotide kinase in a suitable buffer containing ATP and magnesium. The fragmented DNA molecules may optionally be treated to dephosphorylate 5' ends or 3' ends, for example, by using enzymes known in the art, such as phosphatases.

Punctuation Oligonucleotides

In some cases, punctuation oligonucleotides can be utilized in connecting exposed cleaved ends. A punctuation oligonucleotide includes any oligonucleotide that can be joined to a target polynucleotide, so as to bridge two cleaved internal ends of a sample molecule undergoing phase-preserving rearrangement. Punctuation oligonucleotides can comprise DNA, RNA, nucleotide analogues, non-canonical nucleotides, labeled nucleotides, modified nucleotides, or combinations thereof. In many examples, double-stranded punctuation oligonucleotides comprise two separate oligonucleotides hybridized to one another (also referred to as an "oligonucleotide duplex"), and hybridization may leave one or more blunt ends, one or more 3' overhangs, one or more 5' overhangs, one or more bulges resulting from mismatched and/or unpaired nucleotides, or any combination of these. In some instances, different punctuation oligonucleotides are joined to target polynucleotides in sequential reactions or simultaneously. For example, the first and second punctuation oligonucleotides can be added to the same reaction. Alternately, punctuation oligo populations are uniform in some cases.

Punctuation oligonucleotides can be manipulated prior to combining with target polynucleotides. For example, terminal phosphates can be removed. Such a modification precludes location of punctuation oligos to one another rather than to cleaved internal ends of a sample molecule.

Punctuation oligonucleotides contain one or more of a variety of sequence elements, including but not limited to, one or more amplification primer annealing sequences or complements thereof, one or more sequencing primer annealing sequences or complements thereof, one or more barcode sequences, one or more common sequences shared among multiple different punctuation oligonucleotides or subsets of different punctuation oligonucleotides, one or more restriction enzyme recognition sites, one or more overhangs complementary to one or more target polynucleotide overhangs, one or more probe binding sites, one or more random or near-random sequences, and combinations thereof. In some examples, two or more sequence elements are non-adjacent to one another (e.g. separated by one or more nucleotides), adjacent to one another, partially overlapping, or completely overlapping. For example, an amplification primer annealing sequence also serves as a sequencing primer annealing sequence. In certain instances, sequence elements are located at or near the 3' end, at or near the 5' end, or in the interior of the punctuation oligonucleotide.

In alternate embodiments, the punctuation oligo comprises a minimal complement of bases to maintain integrity of the double-stranded molecule, so as to minimize the amount of sequence information it occupies in a sequencing reaction, or the punctuation oligo comprises an optimal number of bases for ligation, or the punctuation oligo length is arbitrarily determined.

In some embodiments, a punctuation oligonucleotide comprises a 5' overhang, a 3' overhang, or both that is complementary to one or more target polynucleotides. In certain instances, complementary overhangs are one or more nucleotides in length, including but not limited to 1, 2, 3, 4, 5, 6, 7, 8, 9, 10, 11, 12, 13, 14, 15, or more nucleotides in length. For example, the complementary overhang is about 1, 2, 3, 4, 5 or 6 nucleotides in length. In some embodiments, a punctuation oligonucleotide overhang is complementary to a target polynucleotide overhang produced by restriction endonuclease digestion or other DNA cleavage method.

Punctuation oligonucleotides can have any suitable length, at least sufficient to accommodate the one or more sequence elements of which they are comprised. In some embodiments, punctuation oligonucleotides are about, less than about, or more than about 4, 5, 6, 7, 8, 9, 10, 15, 20, 25, 30, 35, 40, 45, 50, 55, 60, 65, 70, 75, 80, 90, 100, 200, or more nucleotides in length. In some examples, the punctuation oligonucleotide is 5 to 15 nucleotides in length. In further examples, the punctuation oligonucleotide is about 20 to about 40 nucleotides in length.

Preferably, punctuation oligonucleotides are modified, for example by 5' phosphate excision (via calf alkaline phosphatase treatment, or de novo by synthesis in the absence of such moieties), so that they do not ligate with one another to form multimers. 3' OH (hydroxyl) moieties are able to ligate to 5' phosphates on the cleaved nucleic acids, thereby supporting ligation to a first or a second nucleic acid segment.

Adapter Oligonucleotides

An adapter includes any oligonucleotide having a sequence that can be joined to a target polynucleotide. In various examples, adapter oligonucleotides comprise DNA, RNA, nucleotide analogues, non-canonical nucleotides, labeled nucleotides, modified nucleotides, or combinations thereof. In some instances, adapter oligonucleotides are single-stranded, double-stranded, or partial duplex. In general, a partial-duplex adapter oligonucleotide comprises one or more single-stranded regions and one or more double-stranded regions. Double-stranded adapter oligonucleotides can comprise two separate oligonucleotides hybridized to one another (also referred to as an "oligonucleotide duplex"), and hybridization may leave one or more blunt ends, one or more 3' overhangs, one or more 5' overhangs, one or more bulges resulting from mismatched and/or unpaired nucleotides, or any combination of these. In some embodiments, a single-stranded adapter oligonucleotide comprises two or more sequences that can hybridize with one another. When two such hybridizable sequences are contained in a single-stranded adapter, hybridization yields a hairpin structure (hairpin adapter). When two hybridized regions of an adapter oligonucleotides are separated from one another by a non-hybridized region, a "bubble" structure results. Adapter oligonucleotides comprising a bubble structure consist of a single adapter oligonucleotide comprising internal hybridizations, or comprise two or more adapter oligonucleotides hybridized to one another. Internal sequence hybridization, such as between two hybridizable sequences in adapter oligonucleotides, produce, in some instances, a double-stranded structure in a single-stranded adapter oligonucleotide. In some examples, adapter oligonucleotides of different kinds are used in combination, such as a hairpin adapter and a double-stranded adapter, or adapters of different sequences. In certain cases, hybridizable sequences in a hairpin adapter include one or both ends of the oligonucleotide. When neither of the ends are included in the hybridizable sequences, both ends are "free" or "overhanging." When only one end is hybridizable to another sequence in the adapter, the other end forms an overhang, such as a 3' overhang or a 5' overhang. When both the 5'-terminal nucleotide and the 3'-terminal nucleotide are included in the hybridizable sequences, such that the 5'-terminal nucleotide and the 3'-terminal nucleotide are complementary and hybridize with one another, the end is referred to as "blunt." In some cases, different adapter oligonucleotides are joined to target polynucleotides in sequential reactions or simultaneously. For example, the first and second adapter oligonucleotides is added to the same reaction. In some examples, adapter oligonucleotides are manipulated prior to combining with target polynucleotides. For example, terminal phosphates can be added or removed.

Adapter oligonucleotides contain one or more of a variety of sequence elements, including but not limited to, one or more amplification primer annealing sequences or complements thereof, one or more sequencing primer annealing sequences or complements thereof, one or more barcode sequences, one or more common sequences shared among multiple different adapters or subsets of different adapters, one or more restriction enzyme recognition sites, one or more overhangs complementary to one or more target polynucleotide overhangs, one or more probe binding sites (e.g. for attachment to a sequencing platform, such as a flow cell for massive parallel sequencing, such as developed by Illumina, Inc.), one or more random or near-random sequences (e.g. one or more nucleotides selected at random from a set of two or more different nucleotides at one or more positions, with each of the different nucleotides selected at one or more positions represented in a pool of adapters comprising the random sequence), and combinations thereof. In many examples, two or more sequence elements can be non-adjacent to one another (e.g. separated by one or more nucleotides), adjacent to one another, partially overlapping, or completely overlapping. For example, an amplification primer annealing sequence also serves as a sequencing primer annealing sequence. Sequence elements are located at or near the 3' end, at or near the 5' end, or in the interior of the adapter oligonucleotide. When an adapter oligonucleotides can form secondary structure, such as a hairpin, sequence elements can be located partially or completely outside the secondary structure, partially or completely inside the secondary structure, or in between sequences participating in the secondary structure. For example, when an adapter oligonucleotides comprises a hairpin structure, sequence elements can be located partially or completely inside or outside the hybridizable sequences (the "stem"), including in the sequence between the hybridizable sequences (the "loop"). In some embodiments, the first adapter oligonucleotides in a plurality of first adapter oligonucleotides having different barcode sequences comprise a sequence element common among all first adapter oligonucleotides in the plurality. In some embodiments, all second adapter oligonucleotides comprise a sequence element common to all second adapter oligonucleotides that is different from the common sequence element shared by the first adapter oligonucleotides. A difference in sequence elements can be any such that at least a portion of different adapters do not completely align, for example, due to changes in sequence length, deletion or insertion of one or more nucleotides, or a change in the nucleotide composition at one or more nucleotide positions (such as a base change or base modification). In some embodiments, an adapter oligonucleotides comprises a 5' overhang, a 3' overhang, or both that is complementary to one or more target polynucleotides. Complementary overhangs can be one or more nucleotides in length, including but not limited to 1, 2, 3, 4, 5, 6, 7, 8, 9, 10, 11, 12, 13, 14, 15, or more nucleotides in length. For example, the complementary overhang can be about 1, 2, 3, 4, 5 or 6 nucleotides in length. Complementary overhangs may comprise a fixed sequence. Complementary overhangs may additionally or alternatively comprise a random sequence of one or more nucleotides, such that one or more nucleotides are selected at random from a set of two or more different nucleotides at one or more positions, with each of the different nucleotides selected at one or more positions represented in a pool of adapter oligonucleotides with complementary overhangs comprising the random sequence. In some embodiments, an adapter oligonucleotides overhang is complementary to a target polynucleotide overhang produced by restriction endonuclease digestion. In some embodiments, an adapter oligonucleotide overhang consists of an adenine or a thymine.

Adapter oligonucleotides can have any suitable length, at least sufficient to accommodate the one or more sequence elements of which they are comprised. In some embodiments, adapter oligonucleotides are about, less than about, or more than about 4, 5, 6, 7, 8, 9, 10, 15, 20, 25, 30, 35, 40, 45, 50, 55, 60, 65, 70, 75, 80, 90, 100, 200, or more nucleotides in length. In some examples, the adapter oligonucleotides are 5 to 15 nucleotides in length. In further examples, the adapter oligonucleotides are about 20 to about 40 nucleotides in length.

Preferably, adapter oligonucleotides are modified, for example by 5' phosphate excision (via calf alkaline phosphatase treatment, or de novo by synthesis in the absence of such moieties), so that they do not ligate with one another to form multimers. 3' OH (hydroxyl) moieties are able to ligate to 5' phosphates on the cleaved nucleic acids, thereby supporting ligation to a first or a second nucleic acid segment.

Determining Phase Information of a Nucleic Acid Sample

To determine phase information of a nucleic acid sample, a nucleic acid is first acquired, for example by extraction methods discussed herein. In many cases, the nucleic acid is then attached to a solid surface so as to preserve phase information subsequent to cleavage of the nucleic acid molecule. Preferably, the nucleic acid molecule is assembled in vitro with nucleic acid-binding proteins to generate reconstituted chromatin, though other suitable solid surfaces include nucleic acid-binding protein aggregates, nanoparticles, nucleic acid-binding beads, or beads coated using a nucleic acid-binding substance, polymers, synthetic nucleic acid-binding molecules, or other solid or substantially solid affinity molecules. A nucleic acid sample can also be obtained already attached to a solid surface, such as in the case of native chromatin. Native chromatin can be obtained having already been fixed, such as in the form of a formalin-fixed paraffin-embedded (FFPE) or similarly preserved sample.

Following attachment to a nucleic acid binding moiety, the bound nucleic acid molecule can be cleaved. Cleavage is performed with any suitable nucleic acid cleavage entity, including any number of enzymatic and non-enzymatic approaches. Preferably, DNA cleavage is performed with a restriction endonuclease, fragmentase, or transposase. Alternatively or additionally, nucleic acid cleavage is achieved with other restriction enzymes, topoisomerase, non-specific endonuclease, nucleic acid repair enzyme, RNA-guided nuclease, or alternate enzyme. Physical means can also be used to generate cleavage, including mechanical means (e.g., sonication, shear), thermal means (e.g., temperature change), or electromagnetic means (e.g., irradiation, such as UV irradiation). Nucleic acid cleavage produces free nucleic acid ends, either having 'sticky' overhangs or blunt ends, depending on the cleavage method used. When sticky overhang ends are generated, the sticky ends are optionally partially filled in to prevent re-ligation. Alternatively, the overhangs are completely filled in to produce blunt ends.

In many cases, overhang ends are partially or completely filled in with dNTPs, which are optionally labeled. In such cases, dNTPs can be biotinylated, sulphated, attached to a fluorophore, dephosphorylated, or any other number of nucleotide modifications. Nucleotide modifications can also include epigenetic modifications, such as methylation (e.g., 5-mC, 5-hmC, 5-fC, 5-caC, 4-mC, 6-mA, 8-oxoG, 8-oxoA). Labels or modifications can be selected from those detectable during sequencing, such as epigenetic modifications detectable by nanopore sequencing; in this way, the locations of ligation junctions can be detected during sequencing. These labels or modifications can also be targeted for binding or enrichment; for example, antibodies targeting methyl-cytosine can be used to capture, target, bind, or label blunt ends filled in with methyl-cytosine. Non-natural nucleotides, non-canonical or modified nucleotides, and nucleic acid analogs can also be used to label the locations of blunt-end fill-in. Non-canonical or modified nucleotides can include pseudouridine ($\Psi$), dihydrouridine (D), inosine (I), 7-methylguanosine (m7G), xanthine, hypoxanthine, purine, 2,6-diaminopurine, and 6,8-diaminopurine. Nucleic acid analogs can include peptide nucleic acid (PNA), Morpholino and locked nucleic acid (LNA), glycol nucleic acid (GNA), and threose nucleic acid (TNA). In some cases, overhangs are filled in with un-labeled dNTPs, such as dNTPs without biotin. In some cases, such as cleavage with a transposon, blunt ends are generated that do not require filling in. These free blunt ends are generated when the transposase inserts two unlinked punctuation oligonucleotides. The punctuation oligonucleotides, however, are synthesized to have sticky or blunt ends as desired. Proteins associated with sample nucleic acids, such as histones, can also be modified. For example, histones can be acetylated (e.g., at lysine residues) and/or methylated (e.g., at lysine and arginine residues).

Next, while the cleaved nucleic acid molecule is still bound to the solid surface, the free nucleic acid ends are linked together. Linking occurs, in some cases, through ligation, either between free ends, or with a separate entity, such as an oligonucleotide. In some cases, the oligonucleotide is a punctuation oligonucleotide. In such cases, the punctuation molecule ends are compatible with the free ends of the cleaved nucleic acid molecule. In many cases, the punctuation molecule is dephosphorylated to prevent concatemerization of the oligonucleotides. In most cases, the punctuation molecule is ligated on each end to a free nucleic acid end of the cleaved nucleic acid molecule. In many cases, this ligation step results in rearrangements of the cleaved nucleic acid molecule such that two free ends that were not originally adjacent to one another in the starting nucleic acid molecule are now linked in a paired end.

Following linking of the free ends of the cleaved nucleic acid molecule, the rearranged nucleic acid sample is released from the nucleic acid binding moiety using any number of standard enzymatic and non-enzymatic approaches. For example, in the case of in vitro reconstituted chromatin, the rearranged nucleic acid molecule is released by denaturing or degradation of the nucleic acid-binding proteins. In other examples, cross-linking is reversed. In yet other examples, affinity interactions are reversed or blocked. The released nucleic acid molecule is rearranged compared to the input nucleic acid molecule. In cases where punctuation molecules are used, the resulting rearranged molecule is referred to as a punctuated molecule due to the punctuation oligonucleotides that are interspersed throughout the rearranged nucleic acid molecule. In these cases, the nucleic acid segments flanking the punctuations make up a paired end.

During the cleavage and linking steps of the methods disclosed herein, phase information is maintained since the nucleic acid molecule is bound to a solid surface throughout these processes. This can enable the analysis of phase information without relying on information from other markers, such as single nucleotide polymorphisms (SNPs). Using the methods and compositions disclosed herein, in some cases, two nucleic acid segments within the nucleic acid molecule are rearranged such that they are closer in proximity than they were on the original nucleic acid molecule. In many examples, the original separation distance of the two nucleic acid segments in the starting nucleic acid sample is greater than the average read length of standard sequencing technologies. For example, the starting separation distance between the two nucleic acid segments within the input nucleic acid sample is about 10 kb, 12.5 kb, 15 kb, 17.5 kb, 20 kb, 25 kb, 30 kb, 35 kb, 40 kb, 45 kb, 50 kb, 60 kb, 70 kb, 80 kb, 90 kb, 100 kb, 125 kb, 150 kb, 200 kb, 300 kb, 400 kb, 500 kb, 600 kb, 700 kb, 800 kb, 900 kb, 1 Mb, or greater. In preferred examples, the separation distance between the two rearranged DNA segments is less than the average read length of standard sequencing technologies. For example, the distance separating the two rearranged DNA segments within the rearranged DNA molecule is less than about 50 kb, 40 kb, 30 kb, 25 kb, 20 kb, 17 kb, 15 kb, 14 kb, 13 kb, 12 kb, 11 kb, 10 kb, 9 kb, 8 kb, 7 kb, 6 kb, 5 kb, or less. In preferred cases, the separation distance is less than that of the average read length of a long-read sequencing machine. In these cases, when the rearranged DNA sample is released from the nucleic acid binding moiety and sequenced, phase information is determined and sequence information is generated sufficient to generate a de novo sequence scaffold.

Barcoding a Rearranged Nucleic Acid Molecule

In some examples, the released rearranged nucleic acid molecule described herein is further processed prior to sequencing. For example, the nucleic acid segments comprised within the rearranged nucleic acid molecule can be barcoded. Barcoding can allow for easier grouping of sequence reads. For example, barcodes can be used to identify sequences originating from the same rearranged nucleic acid molecule. Barcodes can also be used to uniquely identify individual junctions. For example, each junction can be marked with a unique (e.g., randomly generated) barcode which can uniquely identify the junction.

Multiple barcodes can be used together, such as a first barcode to identify sequences originating from the same rearranged nucleic acid molecule and a second barcode that uniquely identifies individual junctions.

Barcoding can be achieved through a number of techniques. In some cases, barcodes can be included as a sequence within a punctuation oligo. In other cases, the released rearranged nucleic acid molecule can be contacted to oligonucleotides comprising at least two segments: one segment contains a barcode and a second segment contains a sequence complementary to a punctuation sequence. After annealing to the punctuation sequences, the barcoded oligonucleotides are extended with polymerase to yield barcoded molecules from the same punctuated nucleic acid molecule. Since the punctuated nucleic acid molecule is a rearranged version of the input nucleic acid molecule, in which phase information is preserved, the generated barcoded molecules are also from the same input nucleic acid molecule. These barcoded molecules comprise a barcode sequence, the punctuation complementary sequence, and genomic sequence.

For rearranged nucleic acid molecules with or without punctuation, molecules can be barcoded by other means. For example, rearranged nucleic acid molecules can be contacted with barcoded oligonucleotides which can be extended to incorporate sequence from the rearranged nucleic acid molecule. Barcodes can hybridize to punctuation sequences, to restriction enzyme recognition sites, to sites of interest (e.g., genomic regions of interest), or to random sites (e.g., through a random n-mer sequence on the barcode oligonucleotide). Rearranged nucleic acid molecules can be contacted to the barcodes using appropriate concentrations and/or separations (e.g., spatial or temporal separation) from other rearranged nucleic acid molecules in the sample such that multiple rearranged nucleic acid molecules are not given then same barcode sequence. For example, a solution comprising rearranged nucleic acid molecules can be diluted to such a concentration that only one rearranged nucleic acid molecule will be contacted to a barcode or group of barcodes with a given barcode sequence. Barcodes can be contacted to rearranged nucleic acid molecules in free solution, in fluidic partitions (e.g., droplets or wells), or on an array (e.g., at particular array spots).

Barcoded nucleic acid molecules (e.g., extension products) can be sequenced, for example, on a short-read sequencing machine and phase information is determined by grouping sequence reads having the same barcode into a common phase. Alternatively, prior to sequencing, the barcoded products can be linked together, for example though bulk ligation, to generate long molecules which are sequenced, for example, using long-read sequencing technology. In these cases, the embedded read pairs are identifiable via the amplification adapters and punctuation sequences. Further phase information is obtained from the barcode sequence of the read pair.

Determining Phase Information with Paired Ends

Further provided herein are methods and compositions for determining phase information from paired ends. Paired ends can be generated by any of the methods disclosed or those further illustrated in the provided Examples. For example, in the case of a nucleic acid molecule bound to a solid surface which was subsequently cleaved, following re-ligation of free ends, re-ligated nucleic acid segments are released from the solid-phase attached nucleic acid molecule, for example, by restriction digestion. This release results in a plurality of paired ends. In some cases, the paired ends are ligated to amplification adapters, amplified, and sequenced with short reach technology. In these cases, paired ends from multiple different nucleic acid binding moiety-bound nucleic acid molecules are within the sequenced sample. However, it is confidently concluded that for either side of a paired end junction, the junction adjacent sequence is derived from a common phase of a common molecule. In cases where paired ends are linked with a punctuation oligonucleotide, the paired end junction in the sequencing read is identified by the punctuation oligonucleotide sequence. In other cases, the pair ends were linked by modified nucleotides, which can be identified based on the sequence of the modified nucleotides used.

Alternatively, following release of paired ends, the free paired ends can be ligated to amplification adapters and amplified. In these cases, the plurality of paired ends is then bulk ligated together to generate long molecules which are read using long-read sequencing technology. In other examples, released paired ends are bulk ligated to each other without the intervening amplification step. In either case, the embedded read pairs are identifiable via the native DNA sequence adjacent to the linking sequence, such as a punctuation sequence or modified nucleotides. The concatenated paired ends are read on a long-sequence device, and sequence information for multiple junctions is obtained. Since the paired ends derived from multiple different nucleic acid binding moiety-bound DNA molecules, sequences spanning two individual paired ends, such as those flanking amplification adapter sequences, are found to map to multiple different DNA molecules. However, it is confidently concluded that for either side of a paired end junction, the junction-adjacent sequence is derived from a common phase of a common molecule. For example, in the case of paired ends derived from a punctuated molecule, sequences flanking the punctuation sequence are confidently assigned to a common DNA molecule. In preferred cases, because the individual paired ends are concatenated using the methods and compositions disclosed herein, one can sequence multiple paired ends in a single read.

Sequencing Approaches

The methods and compositions disclosed herein can be used to generate long DNA molecules comprising rearranged segments compared to the input DNA sample. These molecules are sequences using any number of sequencing technologies. Preferably, the long molecules are sequenced using standard long-read sequencing technologies. Additionally or alternatively, the generated long molecules can be modified as disclosed herein to make them compatible with short-read sequencing technologies.

Exemplary long-read sequencing technologies include but are not limited to nanopore sequencing technologies and other long-read sequencing technologies such as Pacific Biosciences Single Molecule Real Time (SMRT) sequencing. Nanopore sequencing technologies include but are not limited to Oxford Nanopore sequencing technologies (e.g., GridION, MinION) and Genia sequencing technologies.

Sequence read lengths can be at least about 100 bp, 200 bp, 300 bp, 400 bp, 500 bp, 600 bp, 700 bp, 800 bp, 900 bp, 1 kb, 2 kb, 3 kb, 4 kb, 5 kb, 6 kb, 7 kb, 8 kb, 9 kb, 10 kb, 20 kb, 30 kb, 40 kb, 50 kb, 60 kb, 70 kb, 80 kb, 90 kb, 100 kb, 200 kb, 300 kb, 400 kb, 500 kb, 600 kb, 700 kb, 800 kb, 900 kb, 1 Mb, 2 Mb, 3 Mb, 4 Mb, 5 Mb, 6 Mb, 7 Mb, 8 Mb, 9 Mb, or 10 Mb. Sequence read lengths can be about 100 bp, 200 bp, 300 bp, 400 bp, 500 bp, 600 bp, 700 bp, 800 bp, 900 bp, 1 kb, 2 kb, 3 kb, 4 kb, 5 kb, 6 kb, 7 kb, 8 kb, 9 kb, 10 kb, 20 kb, 30 kb, 40 kb, 50 kb, 60 kb, 70 kb, 80 kb, 90 kb, 100 kb, 200 kb, 300 kb, 400 kb, 500 kb, 600 kb, 700 kb, 800 kb, 900 kb, 1 Mb, 2 Mb, 3 Mb, 4 Mb, 5 Mb, 6 Mb, 7 Mb, 8 Mb, 9 Mb, or 10 Mb. In some cases, sequence read lengths are at least about 5 kb. In some cases, sequence read lengths are about 5 kb.

In some examples, a long rearranged DNA molecule generated using the methods and compositions disclosed herein, is ligated on one end to a sequencing adapter. In preferred examples, the sequencing adapter is a hairpin adapter, resulting in a self-annealing single-stranded molecule harboring an inverted repeat. In these cases, the molecule is fed through a sequencing enzyme and full length sequence of each side of the inverted repeat is obtained. In most cases, the resulting sequence read corresponds to 2x coverage of the DNA molecule, such as a punctuated DNA molecule harboring multiple rearranged segments, each conveying phase information. In favored instances, sufficient sequence is generated to independently generate a de novo scaffold of the nucleic acid sample.

Alternatively, a long rearranged DNA molecule generated using the methods and compositions disclosed herein, is cleaved to form a population of double stranded molecules of a desired length. In these cases, these molecules are ligated on each end to single stranded adapters. The result is a double stranded DNA template capped by hairpin loops at both ends. The circular molecules are sequenced by continuous sequencing technology. Continuous long read sequencing of molecules containing a long double stranded segment results in a single contiguous read of each molecule. Continuous sequencing of molecules containing a short double stranded segment results in multiple reads of the molecule, which are used either alone or along with continuous long read sequence information to confirm a consensus sequence of the molecule. In most cases, genomic segment borders marked by punctuation oligonucleotides are identified, and it is concluded that sequence adjacent to a punctuation border is in phase. In preferred cases, sufficient sequence is generated to independently generate a de novo scaffold of the nucleic acid sample.

In some cases, rearranged nucleic acid molecules are selected for sequencing based on length. Length-based selection can be used to select for rearranged nucleic acid molecules that contain more rearranged segments, so that shorter rearranged nucleic acid molecules containing only a few rearranged segments are not sequenced or are sequenced in fewer numbers.

Rearranged nucleic acid molecules containing more rearranged segments can provide more phasing information than those molecules containing fewer rearranged segments. Rearranged nucleic acid molecules can be selected for those that contain at least 1, 2, 3, 4, 5, 6, 7, 8, 9, 10, or more rearranged segments. For example, rearranged nucleic acid molecules can be selected for a length of at least 100 bp, 200 bp, 300 bp, 400 bp, 500 bp, 600 bp, 700 bp, 800 bp, 900 bp, 1 kb, 2 kb, 3 kb, 4 kb, 5 kb, 6 kb, 7 kb, 8 kb, 9 kb, 10 kb, 20 kb, 30 kb, 40 kb, 50 kb, 60 kb, 70 kb, 80 kb, 90 kb, 100 kb, 200 kb, 300 kb, 400 kb, 500 kb, 600 kb, 700 kb, 800 kb, 900 kb, 1 Mb, 2 Mb, 3 Mb, 4 Mb, 5 Mb, 6 Mb, 7 Mb, 8 Mb, 9 Mb, 10 Mb, or more. Length-based selection can be a firm exclusion, excluding 100% of rearranged nucleic acid molecules below the chosen length. Alternatively, length-based selection can be an enrichment for longer molecules, removing at least 99.999%, 99.99%, 99.9%, 99%, 98%, 97%, 96%, 95%, 94%, 93%, 92%, 91%, 90%, 85%, 80%, 75%, 70%, 65%, 60%, 55%, 50%, 45%, 40%, 35%, 30%, 25%, 20%, 15%, 10%, 5%, 4%, 3%, 2%, or 1% of rearranged nucleic acid molecules below the chosen length. Length selection of nucleic acids can be performed by a variety of techniques, including but not limited to electrophoresis (e.g., gel or capillary), filtration, bead binding (e.g., SPRI bead size selection), and flow-based methods.

Phased Sequence Assembly

Sequencing data generated using the methods and compositions described herein are used, in preferred embodiments, to generate phased de novo sequence assemblies.

In some examples, a plurality of rearranged (and optionally punctuated) DNA molecules are generated as disclosed herein, and subsequently sequenced using long-read sequencing technology. Sequences from the plurality of rearranged (and optionally punctuated) DNA molecules are compared and, in many cases, a first rearranged (and optionally punctuated) molecule is used to determine phase information for its constituent segments, while comparison to un-rearranged (and optionally punctuated) regions of a second (and additional) rearranged (and optionally punctuated) DNA molecules is used to order the segments of the first punctuated molecule. Repeating this process reciprocally, phase and order information is determined for the majority of the segments in each of the plurality of rearranged molecules. In preferred cases, the resulting assembled sequence is a phased sequence of the input DNA molecule prior to rearrangement occurring, and represents a de novo, phased assembly of the nucleic acid sample.

Alternatively, a rearranged DNA molecule as generated using the methods and compositions disclosed herein is sequenced using long-read sequencing technology and, in parallel, the input DNA is sequenced using standard short-read shotgun sequencing technology. In these cases, the shotgun sequence from the sample is mapped to the long read data generated from the rearranged DNA molecule and/or the phased genomic sequence reads from the rearranged molecule are mapped to sequencing data obtained from the concurrently generated short-read sequencing. In some cases, some of the short-reads map to the long-read generated sequence. In such cases, this overlap allows short sequence reads to be assigned to the same phase as the genomic sequence generated from the rearranged DNA molecule long sequence read.

Information irrelevant to generating a phased sequence assembly can be discarded. In an example, a rearranged DNA molecule as discussed herein is generated and sequenced. The rearranged DNA molecule is found to comprise segments that map to chromosome A and segments that map to chromosome B. In some cases, sequence read information for segments that map to chromosome B can be discarded or unused, and only segments that map to chromosome A are used to generate phased sequence information. In other cases, sequence read information for segments that map to chromosome A can be used to generate phased sequence information about chromosome A, while sequence read information for segments that map to chromosome B can be used to generate phased sequence information about chromosome B, but information about the junction(s) between chromosome A segments and chromosome B segments remains unused or is discarded.

Samples can be manipulated to reduce or remove inter-chromosomal proximity or junction information. For example, a cell sample can be frozen in mitosis prior to rearrangement and sequencing as described herein, thereby disrupting the usual three-dimensional structure of chromosomes in the cells. This can reduce or eliminate inter-chromosomal ligations. In another example, histone post-translational modifications can be removed prior to analysis.

Nucleic Acid Sequence Libraries

Also disclosed herein are methods and compositions for generating nucleic acid sequence libraries. Rearranged molecules are sequenced, and the sequence reads are analyzed.

For a given read, sequence segments can be observed and parsed into multiple rearranged segments. If punctuation oligos are employed, sequence segments can be observed that are locally uninterrupted by punctuation elements. Sequence information in sequence segments is presumed to be in phase, and locally correctly ordered and oriented. Segments on either side of a junction are inferred to be in phase with one another on a common sample nucleic acid molecule but not necessarily to be correctly ordered and oriented relative to one another on the rearranged nucleic acid molecule. A benefit of the rearrangement is that segments positioned far removed from one another are sometimes brought into proximity, such that they are read in a common read and confidently assigned to a common phase even if in the sample molecule they are separated by large distances of identical, difficult to phase sequence. Another benefit is that the segment sequences themselves comprise most, substantially all or all of the original sample sequence, such that in addition to phase information, in some cases contig information is determined sufficient to perform de novo sequence assembly in some cases. This de novo sequence is optionally used to generate a novel scaffold or contig set, or to augment a previously or independently generated contig or scaffold sequence set.

Rearranged molecules, such as in a sequencing library, can comprise at least 2, 3, 4, 5, 6, 7, 8, 9, 10, or more segments, where the segments are not adjacent to other segments on the original input nucleic acid molecule (e.g., input genomic DNA). In some cases, at least about 50%, 55%, 60%, 65%, 70%, 75%, 80%, 85%, 90%, 95%, 96%, 97%, 98%, 99%, 99.9%, 99.99%, 99.999%, or 100% of the segments on a given rearranged molecule map to a common scaffold.

In some cases, on average over a population of rearranged molecules such as a sequencing library, at least about 50%, 55%, 60%, 65%, 70%, 75%, 80%, 85%, 90%, 95%, 96%, 97%, 98%, 99%, 99.9%, 99.99%, 99.999%, or 100% of the segments on a given rearranged molecule map to a common scaffold.

Segments can be about 100 bp, 200 bp, 300 bp, 400 bp, 500 bp, 600 bp, 700 bp, 800 bp, 900 bp, 1 kb, 1.1 kb, 1.2 kb, 1.3 kb, 1.4 kb, 1.5 kb, 2.0 kb, 2.5 kb, 3.0 kb, 3.5 kb, 4.0 kb, 4.5 kb, 5.0 kb, 5.5 kb, 6.0 kb, 6.5 kb, 7.0 kb, 7.5 kb, 8.0 kb, 8.5 kb, 9.0 kb, 9.5 kb, 10.0 kb, or greater in length. Segments can be at least about 100 bp, 200 bp, 300 bp, 400 bp, 500 bp, 600 bp, 700 bp, 800 bp, 900 bp, 1 kb, 1.1 kb, 1.2 kb, 1.3 kb, 1.4 kb, 1.5 kb, 2.0 kb, 2.5 kb, 3.0 kb, 3.5 kb, 4.0 kb, 4.5 kb, 5.0 kb, 5.5 kb, 6.0 kb, 6.5 kb, 7.0 kb, 7.5 kb, 8.0 kb, 8.5 kb, 9.0 kb, 9.5 kb, 10.0 kb, or greater in length. Segments can be at most about 100 bp, 200 bp, 300 bp, 400 bp, 500 bp, 600 bp, 700 bp, 800 bp, 900 bp, 1 kb, 1.1 kb, 1.2 kb, 1.3 kb, 1.4 kb, 1.5 kb, 2.0 kb, 2.5 kb, 3.0 kb, 3.5 kb, 4.0 kb, 4.5 kb, 5.0 kb, 5.5 kb, 6.0 kb, 6.5 kb, 7.0 kb, 7.5 kb, 8.0 kb, 8.5 kb, 9.0 kb, 9.5 kb, 10.0 kb, or greater in length.

Rearranged molecules can have at least 2, 3, 4, 5, 6, 7, 8, 9, 10, or more segments that are at least about 100 bp, 200 bp, 300 bp, 400 bp, 500 bp, 600 bp, 700 bp, 800 bp, 900 bp, 1 kb, 1.1 kb, 1.2 kb, 1.3 kb, 1.4 kb, 1.5 kb, 2.0 kb, 2.5 kb, 3.0 kb, 3.5 kb, 4.0 kb, 4.5 kb, 5.0 kb, 5.5 kb, 6.0 kb, 6.5 kb, 7.0 kb, 7.5 kb, 8.0 kb, 8.5 kb, 9.0 kb, 9.5 kb, 10.0 kb, or greater in length. In some cases, rearranged molecules have at least 3 segments that are at least 500 bp in length. In some cases, rearranged molecules have at least 4 segments that are at least 500 bp in length. In some cases, rearranged molecules have at least 5 segments that are at least 500 bp in length. In some cases, rearranged molecules have at least 6 segments that are at least 500 bp in length.

Rearranged molecules can comprise, when added up across all segments in the rearranged molecule, at least 100 bp, 200 bp, 300 bp, 400 bp, 500 bp, 600 bp, 700 bp, 800 bp, 900 bp, 1 kb, 1.1 kb, 1.2 kb, 1.3 kb, 1.4 kb, 1.5 kb, 2.0 kb, 2.5 kb, 3.0 kb, 3.5 kb, 4.0 kb, 4.5 kb, 5.0 kb, 5.5 kb, 6.0 kb, 6.5 kb, 7.0 kb, 7.5 kb, 8.0 kb, 8.5 kb, 9.0 kb, 9.5 kb, 10.0 kb from one original nucleic acid molecule (e.g, from one chromosome). In some cases, rearranged molecules comprise, when added up across all segments in the rearranged molecule, at least 1000 bp from one original nucleic acid molecule (e.g., from one chromosome). In some cases, rearranged molecules comprise, when added up across all segments in the rearranged molecule, at least 2000 bp from one original nucleic acid molecule (e.g., from one chromosome). In some cases, rearranged molecules comprise, when added up across all segments in the rearranged molecule, at least 3000 bp from one original nucleic acid molecule (e.g., from one chromosome). In some cases, rearranged molecules comprise, when added up across all segments in the rearranged molecule, at least 4000 bp from one original nucleic acid molecule (e.g., from one chromosome).

In some cases, rearranged molecules comprise, when added up across all segments in the rearranged molecule, at least 5000 bp from one original nucleic acid molecule (e.g., from one chromosome).

In some cases, mapping can be conducted with enforced unique mapping. In some cases, less than about 50%, 45%, 40%, 35%, 30%, 25%, 20%, 15%, 10%, 5%, 4%, 3%, 2%, 1%, 0.1%, 0.01%, or 0.001% of segments map ambiguously (e.g., map to multiple locations).

A sequencing library can comprise at least about 10, 100, 1000, 10,000, 100,000, 1 million, 1.1 million, 1.2 million, 1.3 million, 1.4 million, 1.5 million, 1.6 million, 1.7 million, 1.8 million, 1.9 million, 2.0 million, 3 million, 4 million, 5 million, 6 million, 7 million, 8 million, 9 million, 10 million, 20 million, 30 million, 40 million, 50 million, 60 million, 70 million, 80 million, 90 million, 100 million, 200 million, 300 million, 400 million, 500 million, 600 million, 700 million, 800 million, 900 million, 1 billion, 2 billion, 3 billion, 4 billion, 5 billion, 6 billion, 7 billion, 8 billion, 9 billion, 10 billion, 100 billion, 200 billion, 300 billion, 400 billion, 500 billion, 600 billion, 700 billion, 800 billion, 900 billion, or 1 trillion rearranged molecules.

Rearranged molecules in a sequencing library can comprise the necessary adapters, labels, or other components for sequencing, such as particular recognition sequences, hybridization sequences, hairpins (e.g., for SMRTbell), tags (e.g., NanoTags), labels, dyes, or barcodes.

In some cases, a plurality of rearranged DNA molecules is generated as disclosed herein and subsequently sequenced using long-read sequencing technology. Each rearranged molecule is sequenced, and the sequence reads are analyzed. In preferred examples, sequence reads average at least about 5 kb or at least about 10 kb for the sequence reaction. In other examples, sequence reads average at least about 5 kb, 6 kb, 7 kb, 8 kb, 9 kb, 10 kb, 11 kb, 12 kb, 13 kb, 14 kb, 15 kb, 16 kb, 17 kb, 18 kb, 19 kb, 20 kb, 21 kb, 22 kb, 25 kb, 30 kb, 35 kb, 40 kb, or greater. In favored examples, sequence reads are identified that comprise at least 500 bases of a first segment and 500 bases of a second segment, where the first and second segments are not adjacent on the original sample input nucleic acid. The segments can be joined by a punctuation oligo sequence. In other examples, the sequence reads comprise at least about 100 bases, 200 bases, 300 bases, 400 bases, 500 bases, 600 bases, 700 bases, 800 bases, 900 bases, 1000 bases, or greater of a first DNA segment and at least about 100 bases, 200 bases, 300 bases, 400 bases, 500 bases, 600 bases, 700 bases, 800 bases, 900 bases, 1000 bases, or greater of a second DNA segment. In some examples, the first and second segment sequences are mapped to a scaffold genome and are found to map to contigs that are separated by at least 100 kb. In other examples, the separation distance is at least about 8 kb, 9 kb, 10 kb, 12.5 kb, 15 kb, 17.5 kb, 20 kb, 25 kb, 30 kb, 35 kb, 40 kb, 45 kb, 50 kb, 60 kb, 70 kb, 80 kb, 90 kb, 100 kb, 125 kb, 150 kb, 200 kb, 300 kb, 400 kb, 500 kb, 600 kb, 700 kb, 800 kb, 900 kb, 1 Mb, or greater. In most cases, the first contig and the second contig each comprise a single heterozygous position, the phase of which is not determined in a scaffold. In preferred examples, the heterozygous position of the first contig is spanned by the first segment of the long read, and the heterozygous position of the second contig is spanned by the second segment of the long read. In such cases, the reads each span their contigs' respective heterozygous regions and sequence of the read segments indicates that a first allele of the first contig and a first allele of the second contig are in phase. If sequences from the first and second nucleic acid segments are detected in a single long sequence read, it is determined that the first and second nucleic acid segments are comprised on the same DNA molecule in the input DNA sample. In these preferred embodiments, nucleic acid sequence libraries generated by the methods and compositions disclosed herein provide phase information for contigs that are positioned far apart from one another on a genome scaffold.

Alternatively, a plurality of paired end molecules is generated as described herein, and subsequently sequenced using long read sequencing technology. In some cases, the average read length for the library is determined to be about 1 kb. In other cases, the average read length for the library is about 100 bp, 200 bp, 300 bp, 400 bp, 500 bp, 600 bp, 700 bp, 800 bp, 900 bp, 1 kb, 1.1 kb, 1.2 kb, 1.3 kb, 1.4 kb, 1.5 kb, 2.0 kb, 2.5 kb, 3.0 kb, 3.5 kb, 4.0 kb, 4.5 kb, 5.0 kb, 5.5 kb, 6.0 kb, 6.5 kb, 7.0 kb, 7.5 kb, 8.0 kb, 8.5 kb, 9.0 kb, 9.5 kb, 10.0 kb, or greater. In many examples, paired end molecules comprise a first DNA segment and a second DNA segment that, within the input DNA sample, are in phase and separated by a distance greater than 10 kb. In some examples, the separation distance between two such DNA segments is greater than about 5 kb, 6 kb, 7 kb, 8 kb, 9 kb, 10 kb, 11 kb, 12 kb, 13 kb, 14 kb, 15 kb, 20 kb, 23 kb, 25 kb, 30 kb, 32 kb, 35 kb, 40 kb, 50 kb, 60 kb, 75 kb, 100 kb, 200 kb, 300 kb, 400 kb, 500 kb, 750 kb, 1 Mb, or greater. In most cases, sequence reads are generated from paired end molecules, some of which comprise at least 300 bases of sequence from a first nucleic acid segment and at least 300 bases of sequence from a second nucleic acid segment. In other examples, the sequence reads comprise at least about 50 bases, 100 bases, 150 bases, 200 bases, 250 bases, 300 bases, 350 bases, 400 bases, 450 bases, 500 bases, 550 bases, 600 bases, 650 bases, 700 bases, 750 bases, 800 bases, or greater of a first DNA segment and at least about 50 bases, 100 bases, 150 bases, 200 bases, 250 bases, 300 bases, 350 bases, 400 bases, 450 bases, 500 bases, 550 bases, 600 bases, 650 bases, 700 bases, 750 bases, 800 bases, or greater of a second DNA segment. If sequences from the first and second nucleic acid segments are detected in a single sequence read, it can be determined that the first and second nucleic acid segments are in phase on the same DNA molecule in the input DNA sample. In such cases, the generated sequence libraries yield phase information for DNA segments that are separated in the nucleic acid sample by greater than the read length of the sequencing technology used to sequence them.

Alternatively, a plurality of sequence reads is generated from a rearranged DNA nucleic acid sequence library as discloses herein. In some cases, the library conveys phase information, as disclosed herein and as described in the provided Examples, such that segments on either side of a segment junction are determined to be in phase on a single molecule. In some examples, the generated sequence reads represent at least 80% of the nucleic acid sequence of the input DNA sample. In other examples, the generated sequence reads represent at least about 45%, 50%, 55%, 60%, 65%, 70%, 75%, 80%, 85%, 90%, 95%, or 100% of the nucleic acid sequence of the input DNA sample. In preferred examples, the sequence reads are used to generate de novo contig information that spans at least 80% of the input DNA sample. In other examples, the sequence reads are used to generate de novo contig information that spans at least about 45%, 50%, 55%, 60%, 65%, 70%, 75%, 80%, 85%, 90%, 95%, or 100% of the input DNA sample. In most cases, the sequence reads are used to determine phase information, which is optionally subsequently used to order and orient the contigs relative to each other in order to generate a phased sequence assembly of the input DNA sample. In preferred embodiments, the nucleic acid sequence libraries generated from the rearranged DNA molecules convey phase information and, preferably, also encompass sequence information comprising a substantial portion of the total nucleic acid sequence, such that a de novo sequence assembly is concurrently generated.

Sequencing of a library of rearranged molecules can be performed to achieve a sequencing coverage of at least about 1×, 2×, 3×, 4×, 5×, 6×, 7×, 8×, 9×, 10, 11×, 12×, 13×, 14×, 15×, 16×, 17×, 18×, 19×, 20×, 21×, 22×, 23×, 24×, 25×, 26×, 27×, 28×, 29×, 30×, 31×, 32×, 33×, 34×, 35×, 336×, 37×, 38×, 39×, 40×, 41×, 42×, 43×, 44×, 45×, 46×, 47×, 48×, 49×, 50×, 55×, 60×, 65×, 70×, 75×, 80×, 85×, 90×, 95×, 100×, or more.

Preserved DNA Molecule Phasing

Furthermore, disclosed herein are methods and compositions for phasing and de novo assembling a nucleic acid sequence that, in preferred embodiments, comprises nearly the entire input nucleic acid molecule.

The techniques of the present disclosure can be used to phase a variety of markers, including but not limited to single nucleotide polymorphisms (SNPs), insertions or deletions (INDELs), and structural variants (SVs). For example, the presence of two or more segments together on a rearranged DNA molecule can be used to infer that the sequences of the segments are in phase. This can permit phasing without reliance on previously known phasing of markers.

In some cases, SNPs are phased. In some cases, INDELs are phased. In some cases, SVs are phased. Phasing can be confirmed with reference to one or more markers. In some cases, phasing is confirmed with reference to SNPs. In some cases, phasing is confirmed without reference to SNPs. In some cases, phasing is confirmed with reference to INDELs. In some cases, phasing is confirmed without reference to INDELs. In some cases, phasing is confirmed with reference to SVs. In some cases, phasing is confirmed without reference to SVs. In some examples, a high molecular weight (HMW) nucleic acid sample is extracted using standard methods known in the art. In most cases, these HMW nucleic acid samples comprise at least some nucleic acid molecules which are at least 100 kb in length. One or more of the 100 kb nucleic acid molecules comprises a first nucleic acid segment and a second nucleic acid segment that are separated by distance that is greater than the average read length of standard sequencing technologies. In other examples, the nucleic acid sample comprises at least some nucleic acid molecules which are at least about 30 kb, 40 kb, 50 kb, 60 kb, 70 kb, 80 kb, 90 kb, 100 kb, 110 kb, 120 kb, 130 kb, 140 kb, 150 kb, or greater in length, one or more of which comprises at least a first nucleic acid segment and a second nucleic acid segment that are separated by a distance that is greater than the average read length of standard sequencing technologies, such as those described herein.

To determine the phase information is such examples, the first and second nucleic acid segments need to be detected within a single sequencing read. Therefore, the relative position of the first and second nucleic acid segments must be changed such that the first and second DNA segments are separated by a distance that is less than the average read length of standard sequencing technologies. In order to generate the desired phase information, this rearrangement should not result in loss of phase information. In preferred examples, this rearrangement is achieved by the methods and compositions disclosed herein and as described within the provided Examples. In favored examples, during phase-maintaining rearrangement, no more than 10% of the starting nucleic acid molecule is deleted. That is, the first segment and the second segment are not brought into proximity simply by deleting the intervening sequence. Rather, the segments are rearranged relative to one another without deletion of the majority of the intervening sequence. In other examples, no more than about 2%, 5%, 7%, 1, 12%, 13%, 14%, 15%, 20%, 23%, 25%, 30%, 35%, 40%, 50%, 55%, 60%, 70%, 80%, 90%, or 95% of the starting nucleic acid molecule is deleted. Since, in favored examples, nearly the entire input nucleic acid molecule is preserved, following sequencing, the generated sequence reads are used to assemble, order, and orient de novo generated contigs such that nearly the entire input nucleic acid molecule is sequenced, assembled, and phased.

Applications

The techniques of the present disclosure can be used for a variety of genetics and genomics applications, including but not limited to generation of de novo sequence assemblies (including phased sequence assemblies), mapping reads to a scaffold (including with phasing information), determining phasing information, and identifying structural variants.

The techniques disclosed herein are useful in many fields including, by way of non-limiting example, forensics, agriculture, environmental studies, renewable energy, epidemiology or disease outbreak response, and species preservation.

Techniques of the present disclosure can be used for diagnosing disease states, such as cancer. Techniques of the present disclosure can be used for phasing of clinically important regions, analysis of structural variants, resolution of pseudogenes (e.g., STRC), targeted panels for drugable structural variants in cancer, and other applications. For example, an excess of proximity ligation evens between regions of the genome that are far apart linearly or on separate chromosomes can be indicative of diseases like cancer.

Native chromatin from tissue that is diseased or suspected of being diseased can be analyzed using the techniques of the present disclosure. The three-dimensional architecture of the genome within such a tissue sample can be analyzed, for example by analyzing several samples from different locations within a tissue volume.

In some cases, such as for de novo genome assembly, the biological or pathological signal can be removed from these data. For example, cells can be treated with reagents that cause mitotic arrest, or that disrupt heterochromatin or other regional features of genome architecture, prior to adding a fixing agent that locks in the three-dimensional architecture prior to proximity ligation. In such cases, the resulting data can lack diagnostic utility, but can be maximally useful for genome assembly.

Molecules and libraries generated as disclosed herein are used in a number of applications, such as applications related to genome assembly and contig or other sequence information phasing, such as is done to assign sequence information to a specific molecule of origin or sister chromatid of origin in a diploid organism's genome assembly.

Molecules are sequenced, and contiguous segments are identified as mapping to consecutive bases of a common contig or scaffold. Junctions between segments are identified as regions where bases cease to map to consecutive bases of a common contig or scaffold. In some cases, nucleic acid sequence that maps to multiple regions of a genome (such as repetitive sequence) is discarded. Alternately, particularly if one or both ends of a repetitive sequence maps to a common scaffold and the difference between sequence positions for the uniquely mapping sequence at the ends of the repetitive sequence is consistent with the repetitive region being included in the scaffold, then a repetitive region is assigned to a common segment with its adjacent unique sequence.

In preferred embodiments, adjacent segments of a molecule or library constituent as disclosed herein are assigned to a common phase of a common molecule of the genome. That is, the contigs to which the segments map are assigned to a common phase, and single nucleotide polymorphisms, insertions, deletions, transversions, translocations or other nucleic acid features indicated by one or both segments are assigned to a common molecule.

Often, all or a majority of segments map to a common scaffold or contig, such that their coexistence on a single molecule of the library is indicative that single nucleotide polymorphisms, insertions, deletions, transversions, translocations or other nucleic acid features indicated by one or both segments are assigned to a common molecule. In some cases at least 50%, 55%, 60%, 65%, 70%, 75%, 80%, 85%, 90%, 91%, 92%, 93%, 94%, 95%, 96%, 97%, 98%, 99%, or more than 99% of the segments, or at least 50%, 55%, 60%, 65%, 70%, 75%, 80%, 85%, 90%, 91%, 92%, 93%, 94, 95%, 96%, 97%, 98%, 99%, or more than 99% of the segments sequence, maps to a common scaffold.

In some cases it is beneficial to enrich for molecule generation so as to ensure or increase the likelihood of segments ligating so as to reflect physical linkage or phase information, or so that ligated segments arise from a common physical molecule of origin. A number of approaches effect this goal.

As discussed herein, in some cases libraries are generated through the cleavage and re-ligation of isolated nucleic acid molecules onto which chromatin or other nucleic acid binding moieties have been assembled. By isolating the molecules, for example by separating them from nucleic acid binding proteins or other native chromatin constituents, one allows individual molecules to separate from one another. By binding the isolated nucleic acid molecules such that separate segments are held together independent of their common phosphodiester backbones, the phase information common to segments of a molecule of origin is preserved during the process of cleavage and relegation such that a cleaved segment is likely to rejoin to a second segment derived from a molecule of origin common to the two segments. This frequency is increased through any number of approaches, such as, for example, by diluting molecules prior to chromatin assembly, or by attaching nucleic acid molecules to distinct locations on a common surface at a density below that at which segments form separate molecules are likely to ligate.

When beads such as SPRI beads are used to anchor molecules for digestion and assembly, selecting beads that have larger surface areas, or adding more beads so as to increase the total overall surface area available for binding, in some cases decreases the chance of intermolecular ligation events.

Alternately, in some cases steps are taken to reduce intermolecular interactions among nucleic acid molecules that are bound by native chromatin, such as occurs when cells are treated using a fixative. Examples of such steps include actively targeting cells at a point in their cell cycles such that intermolecular interactions are likely to be minimized. This is accomplished in some cases by freezing or fixing cells in mitosis so as to selectively access their nucleic acids when chromosomes are less likely to be assembled into sub-nuclear structures that may lead to intermolecular ligation events. Alternately or in combination, cells, nuclei, or isolated chromatin from cells are treated so as to remove histone post-translational modifications, so as to remove three-dimensional mapping information and concurrently improve the chance that segments from a single molecule ligate to one another in library generation for sequencing/ phasing information.

Aside from biochemical or 'wet-lab' approaches to reducing intermolecular ligation events in rearranged library formation, computational approaches are also available to reduce the impact of intermolecular ligation events on phase determination. For example, in some cases individual molecules are screened by assessing the mapping distributions of uniquely mapping segments in ligated rearranged molecules. Molecules comprising segments that map to likely distinct molecules above a threshold level are excluded. That is, in some cases, sequence information for molecules that comprise segments that uniquely map to a common scaffold at less than 50%, 55%, 60%, 65%, 70%, 75%, 80%, 85%, 90%, 95%, or up to 99% or greater are excluded from further analysis. In exemplary cases, this threshold is at or about 70%, or at or about 80%, or at or about 90%. In these cases, sequence of molecules that comprise a percentage of segments that map elsewhere than a first common scaffold is excluded from analysis.

Similarly, in some cases, sequence information for molecules that comprise aggregate uniquely mapping sequence that map to a common scaffold at less than 50%, 55%, 60%, 65%, 70%, 75%, 80%, 85%, 90%, 95%, or up to 99% or greater are excluded from further analysis. In exemplary cases, this threshold is at or about 70%, or at or about 80%, or at or about 90%. In these cases, sequence of molecules that comprise a percentage of uniquely mapping sequence that map elsewhere than a first common scaffold is excluded from analysis.

Alternately or in combination, sequences of molecules comprising segments that uniquely map to more than one scaffold are further processed, such as to minimize the impact on phase conclusions without losing sequence information such as SNP data, insertion data, deletion data, inversion data or other genomic rearrangement information that may be captured in sequenced segments. For example, for molecule sequences that comprise segments that uniquely map to two scaffolds (predominantly or exclusively), the segments that map to the first scaffold are assigned to a common phase of that scaffold, while the segments that map to the second scaffold are assigned to a common phase of the second scaffold. That is, segments that map to a first common scaffold are assigned to a common phase on that scaffold, while segments that map to a second common scaffold are determined to be informative of common phase information for the second scaffold, but the segments that map (such as uniquely map) to the first scaffold are not determined to be informative as to phase information with respect to the segments that map to the second scaffold.

Alternately, in some cases a plurality of independent molecule sequences are obtained comprising first population of segments that uniquely map to a first scaffold, and a second population of segments that uniquely map to a second scaffold. In these cases, it is optionally inferred that the first scaffold and the second scaffold are in fact in phase in the nucleic acid sample, for example due to a translocation in the sample genome under analysis.

These approaches allow for the selective enrichment for molecular sequence that is likely to be informative as to phase of the underlying molecules from which the rearranged library, and the rearranged library's sequence data, are derived.

In some cases library generation and sequence analysis are used in combination to obtain sequence information and phase information. In some such cases, ligation junctions are labeled, for example using a modified nucleotide base that is compatible with long read sequencing technology and that is readily identified in reads of such technology. Examples are provided herein.

Using such junction markers, one is able to identify segment junctions with a high degree of confidence independent of the segment sequence. Consequently, sequence rearrangements in library construction are readily distinguished from 'rearrangement events' that occur in the sample and are reflective of sample nucleic acid sequence or architecture. Such events include, for example, insertions, deletions, inversions, transversions or translocations. Observing such events in a segment, when such events are not tagged by a junction marker such as a modified nucleic acid, is indicative that the events are reflective of underlying sample sequence.

Alternately or in combination, one may rely upon depth of library coverage to provide some degree of confidence as to molecular structure. That is, in sequencing multiple independently generated library constituents, one may find multiple, independently generated segments sharing a common rearrangement profile. If such profile comprises a common 'rearrangement event' in multiple independently derived library constituents, one may infer that the 'rearrangement event' which they indicate is reflective of the underlying sample sequence rather than being a product of the library generation process.

A wide diversity of library constituents are consistent with the disclosure herein.

Library constituents are preferably longer on average than a single read of prevailing long read sequencing technology, such that the sequencing technology is used most efficiently in sequencing the library. However, this is not an absolute requirement, and libraries comprising, predominantly comprising, or consisting of constituents smaller than the length of a long range sequencing run are consistent with the disclosure herein.

Libraries disclosed herein may vary in their fraction of the overall sample represented in the library, mean or median rearranged molecule size, segment size, and number of segments per molecule. In many embodiments, libraries are configured so that a single long read spans at least part of three segments of a molecular constituent of the library. In many embodiments, libraries are configured so that segments in phase but dispersed throughout a genomic sample are reconfigured so that they are adjacent or otherwise included in a single long range sequence read, so as to facilitate their assignment to a common phase of a common molecule.

Computer Systems and Improvement in Operation Thereof

Methods as described herein are in some cases implemented by way of machine (or computer processor) executable code (or software) stored on an electronic storage location of the server 1001, such as, for example, on the memory 1010, or electronic storage unit 1015. During use, the code can be executed by the processor 1005. In some cases, the code can be retrieved from the storage unit 1015 and stored on the memory 1010 for ready access by the processor 1005. In some situations, the electronic storage unit 115 can be precluded, and machine-executable instructions are stored on memory 1010. Alternatively, the code can be executed on a second computer system 1040.

Aspects of the systems and methods provided herein, such as the server 1001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (for example, read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" can refer to any medium that participates in providing instructions to a processor for execution.

Hence, a machine readable medium, such as computer-executable code, may take many forms, including but not limited to, tangible storage medium, a carrier wave medium, or physical transmission medium. Non-volatile storage media can include, for example, optical or magnetic disks, such as any of the storage devices in any computer(s) or the like, such may be used to implement the system. Tangible transmission media can include: coaxial cables, copper wires, and fiber optics (including the wires that comprise a bus within a computer system). Carrier-wave transmission media may take the form of electric or electromagnetic signals, or acoustic or light waves such as those generated during radio frequency (RF) and infrared (IR) data communications. Common forms of computer-readable media therefore include, for example: a floppy disk, a flexible disk, hard disk, magnetic tape, any other magnetic medium, a CD-ROM, DVD, DVD-ROM, any other optical medium, punch cards, paper tame, any other physical storage medium with patterns of holes, a RAM, a ROM, a PROM and EPROM, a FLASH-EPROM, any other memory chip or cartridge, a carrier wave transporting data or instructions, cables, or links transporting such carrier wave, or any other medium from which a computer may read programming code and/or data. Many of these forms of computer readable media may be involved in carrying one or more sequences of one or more instructions to a processor for execution.

A computer system may be used to implement one or more steps of a method described herein, including, for example, sample collection, sample processing, sequence generation and sequence analysis.

A client-server and/or relational database architecture can be used in any of the methods described herein. In general, a client-server architecture is a network architecture in which each computer or process on the network is either a client or a server. Server computers can be powerful computers dedicated to managing disk drives (file servers), printers (print servers), or network traffic (network servers). Client computers can include PCs (personal computers) or workstations on which users run applications, as well as example output devices as disclosed herein. Client computers can rely on server computers for resources, such as files, devices, and even processing power. The server computer handles all of the database functionality. The client computer can have software that handles front-end data management and receive data input from users.

After performing a calculation, a processor can provide the output, such as from a calculation, back to, for example, the input device or storage unit, to another storage unit of the same or different computer system, or to an output device. Output from the processor can be displayed by a data display, for example, a display screen (for example, a monitor or a screen on a digital device), a print-out, a data signal (for example, a packet), a graphical user interface (for example, a webpage), an alarm (for example, a flashing light or a sound), or a combination of any of the above. In an embodiment, an output is transmitted over a network (for example, a wireless network) to an output device. The output device can be used by a user to receive the output from the data-processing computer system. After an output has been received by a user, the user can determine a course of action, or can carry out a course of action, such as a medical treatment when the user is medical personnel. In some embodiments, an output device is the same device as the input device. Example output devices include, but are not limited to, a telephone, a wireless telephone, a mobile phone, a PDA, a flash memory drive, a light source, a sound generator, a fax machine, a computer, a computer monitor, a printer, an iPod, and a webpage. The user station may be in communication with a printer or a display monitor to output the information processed by the server. Such displays, output devices, and user stations can be used to provide an alert to the subject or to a caregiver thereof.

Data relating to the present disclosure can be transmitted over a network or connections for reception and/or review by a receiver. The receiver can be but is not limited to the subject to whom the report pertains; or to a caregiver thereof, for example, a health care provider, manager, other healthcare professional, or other caretaker; a person or entity that performed and/or ordered the genotyping analysis; a genetic counselor. The receiver can also be a local or remote system for storing such reports (for example servers or other systems of a "cloud computing" architecture). In one embodiment, a computer-readable medium includes a medium suitable for transmission of a result of an analysis of a biological sample.

Datasets and sequence libraries as disclosed herein are consistent with computer-based phase assignment of nucleic acid sequence information, such as that which is obtained through the sequencing of a heterozygous diploid eukaryotic genome. Computers that analyze such data may assign reads into scaffolds, in some cases generating maps that comprise entire 'end-to-end' chromosome maps for a sample genome. However, most approaches are unable to assign heterozygous sequence to a common phase when said heterozygous sequence is separated by greater than a read length of the sequencing technology. Thus, heterozygous loci are not accurately mapped to a common phase using most computer-based genome assembly approaches.

Methods, databases and systems disclosed herein allow for the assignment of heterozygous sequence information to a common phase, even when the heterozygous loci are separated by more than the sequence distance generated by a single long read. As such, the methods, databases and systems disclosed herein provide for the improvement in performance of computer systems related to genome sequencing and genome sequence assembly. For example, techniques of the present disclosure can allow for improving the calculation speed, thereby reducing computational time or computational burden. These techniques can also allow for reduced memory requirements, including transient memory and non-transient data storage requirements. In some cases, techniques of the present disclosure can enable the computation of previously non-computable calculations.

The detailed description is further supplemented with reference to the following numbered embodiments. 1. A method of generating long-distance phase information from a first DNA molecule, comprising: a) providing a first DNA molecule having a first segment and a second segment, wherein the first segment and the second segment are not adjacent on the first DNA molecule; b) contacting the first DNA molecule to a DNA binding moiety such that the first segment and the second segment are bound to the DNA binding moiety independent of a common phosphodiester backbone of the first DNA molecule; c) cleaving the first DNA molecule such that the first segment and the second segment are not joined by a common phosphodiester backbone; d) attaching the first segment to the second segment via a phosphodiester bond to form a reassembled first DNA molecule; and e) sequencing at least 4 kb of consecutive sequence of the reassembled first DNA molecule comprising a junction between the first segment and the second segment in a single sequencing read, wherein first segment sequence and second segment sequence represent long-distance phase information from a first DNA molecule. 2. The method of numbered embodiment 1, wherein the DNA binding moiety comprises a plurality of DNA-binding molecules. 3. The method of any one of numbered embodiments 1-2, wherein contacting the first DNA molecule to a plurality of DNA-binding molecules comprises contacting to a population of DNA-binding proteins. 4. The method of any one of numbered embodiments 1-3, wherein the population of DNA-binding proteins comprises nuclear proteins. 5. The method of any one of numbered embodiments 1-4, wherein the population of DNA-binding proteins comprises nucleosomes. 6. The method of any one of numbered embodiments 1-5, wherein the population of DNA-binding proteins comprises histones. 7. The method of any one of numbered embodiments 1-6, wherein contacting the first DNA molecule to a plurality of DNA-binding moieties comprises contacting to a population of DNA-binding nanoparticles. 8. The method of any one of numbered embodiments 1-7, wherein the first DNA molecule has a third segment not adjacent on the first DNA molecule to the first segment or the second segment, wherein the contacting in (b) is conducted such that the third segment is bound to the DNA binding moiety independent of the common phosphodiester backbone of the first DNA molecule, wherein the cleaving in (c) is conducted such that the third segment is not joined by a common phosphodiester backbone to the first segment and the second segment, wherein the attaching comprises attaching the third segment to the second segment via a phosphodiester bond to form the reassembled first DNA molecule, and wherein the consecutive sequence sequenced in (e) comprises a junction between the second segment and the third segment in a single sequencing read. 9. The method of any one of numbered embodiments 1-9, comprising contacting the first DNA molecule to a cross-linking agent. 10. The method of any one of any one of numbered embodiments 1-9, comprising contacting the first DNA molecule to a cross-linking agent. 11. The method of any one of numbered embodiments 1-10, wherein the cross-linking agent is formaldehyde. 12. The method of any one of numbered embodiments 1-11, wherein the cross-linking agent is formaldehyde. 13. The method of any one of numbered embodiments 1-12, wherein the DNA binding moiety is bound to a surface comprising a plurality of DNA binding moieties. 14. The method of any one of numbered embodiments 1-13, wherein the DNA binding moiety is bound to a solid framework comprising a bead. 15. The method of any one of numbered embodiments 1-14, wherein cleaving the first DNA molecule comprises contacting to a restriction endonuclease. 16. The method of any one of numbered embodiments 1-15, wherein cleaving the first DNA molecule comprises contacting to a nonspecific endonuclease. 17. The method of any one of numbered embodiments 1-16, wherein cleaving the first DNA molecule comprises contacting to a tagmentation enzyme. 18. The method of any one of numbered embodiments 1-17, wherein cleaving the first DNA molecule comprises contacting to a transposase. 19. The method of any one of numbered embodiments 1-18, wherein cleaving the first DNA molecule comprises shearing the first molecule. 20. The method of any one of numbered embodiments 1-19, comprising adding a tag to at least one exposed end. 21. The method of any one of numbered embodiments 1-20, wherein the tag comprises a labeled base. 22. The method of any one of numbered embodiments 1-21, wherein the tag comprises a methylated base. 23. The method of any one of numbered embodiments 1-22, wherein the tag comprises a biotinylated base. 24. The method of any one of numbered embodiments 1-23, wherein the tag comprises uridine. 25. The method of any one of numbered embodiments 1-24, wherein the tag comprises a noncanonical base. 26. The method of any one of numbered embodiments 1-25, wherein the tag generates a blunt ended exposed end. 27. The method of any one of numbered embodiments 1-26, comprising adding at least one base to a recessed strand of a first segment sticky end. 28. The method of any one of any one of numbered embodiments 1-27, comprising adding a linker oligo comprising an overhang that anneals to the first segment sticky end. 29. The method of any one of any one of numbered embodiments 1-28, wherein the linker oligo comprises an overhang that anneals to the first segment sticky end and an overhang that anneals to the second segment sticky end. 30. The method of any one of any one of numbered embodiments 1-29, wherein the linker oligo does not comprise two 5' phosphate moieties. 31. The method of any one of numbered embodiments 1-30, wherein attaching comprises ligating. 32. The method of any one of numbered embodiments 1-31, wherein attaching comprises DNA single strand nick repair. 33. The method of any one of numbered embodiments 1-32, wherein the first segment and the second segment are separated by at least 10 kb on the first DNA molecule prior to cleaving the first DNA molecule. 34. The method of any one of numbered embodiments 1-33, wherein the first segment and the second segment are separated by at least 15 kb on the first DNA molecule prior to cleaving the first DNA molecule. 35. The method of any one of numbered embodiments 1-34, wherein the first segment and the second segment are separated by at least 30 kb on the first DNA molecule prior to cleaving the first DNA molecule. 36. The method of any one of numbered embodiments 1-35, wherein the first segment and the second segment are separated by at least 50 kb on the first DNA molecule prior to cleaving the first DNA molecule. 37. The method of any one of numbered embodiments 1-36, wherein the first segment and the second segment are separated by at least 100 kb on the first DNA molecule prior to cleaving the first DNA molecule. 38. The method of any one of numbered embodiments 1-37, wherein the sequencing comprises single molecule long read sequencing. 39. The method of any one of numbered embodiments 1-38, wherein the long read sequencing comprises a read of at least 5 kb. 40. The method of any one of numbered embodiments 1-39, wherein the long read sequencing comprises a read of at least 10 kb. 41. The method of any one of numbered embodiments 140, wherein the first reassembled DNA molecule comprises a hairpin moiety linking a 5' end to a 3' end at one end of the first DNA molecule. 42. The method of any one of numbered embodiments 1-42, comprising sequencing a second reassembled version of the first DNA molecule. 43. The method of any one of numbered embodiments 1-42, wherein the first segment and the second segment are each at least 500 bp. 44. The method of any one of numbered embodiments 1-43, wherein the first segment, the second segment, and the third segment are each at least 500 bp. 45. A method of genome assembly comprising: a) obtaining a first DNA molecule complexed to a structure; b) cleaving the first DNA molecule to form a first exposed end and a second exposed end, wherein the first exposed end and the second exposed end were not adjacent on the molecule prior to said cleaving; c) cleaving the first DNA molecule to form a third exposed end and a fourth exposed end, wherein the third exposed end and the fourth exposed end were not adjacent on the molecule prior to said cleaving; d) attaching said first exposed end and said second exposed end to form a first junction; e) attaching said third exposed end and said fourth exposed end to form a second junction f) sequencing across said first junction and said second junction in a single sequencing read; g) mapping sequence on a first side of said first junction to a first contig of said plurality of contigs; h) mapping sequence on a second side of said first junction to a second contig of said plurality of contigs; i) mapping sequence on a first side of said second junction to a second contig of said plurality of contigs; j) mapping sequence on a second side of said second junction to a third contig of said plurality of contigs and k) assigning said first contig, said second contig, and said third contig to a common phase of a genome assembly. 46. The method of numbered embodiment 45, wherein said plurality of contigs are generated from shotgun sequence data. 47. The method of any one of numbered embodiments 45-46, wherein said plurality of contigs are generated from single molecule long read data. 48. The method of any one of numbered embodiments 45-47, wherein said single molecule long read data comprises said plurality of contigs. 49. The method of any one of numbered embodiments 45-48, wherein said plurality of contigs is concurrently obtained through sequencing across said first junction and said second junction. 50. The method of any one of numbered embodiments 45-49, wherein sequencing across said marker oligo comprises sequencing at least 10 kb. 51. The method of any one of numbered embodiments 45-50, wherein said structure comprises a population of DNA binding moieties bound to the first DNA molecule to form reconstituted chromatin. 52. The method of any one of numbered embodiments 45-51, wherein said reconstituted chromatin is contacted to a cross-linking agent. 53. The method of any one of numbered embodiments 45-52, wherein said crosslinking agent comprises formaldehyde. 54. The method of any one of numbered embodiments 45-53, wherein said population of DNA binding moieties comprises histones. 55. The method of any one of numbered embodiments 45-54, wherein said population of DNA binding moieties comprises nanoparticles. 56. The method of any one of numbered embodiments 45-55, wherein said structure comprises native chromatin. 57. The method of any one of numbered embodiments 45-56, wherein the first exposed end and the second exposed end are separated by at least 10 kb on the first DNA molecule prior to cleaving the first DNA molecule. 58. The method of any one of numbered embodiments 45-57, wherein the first exposed end and the second exposed end are separated by at least 15 kb on the first DNA molecule prior to cleaving the first DNA molecule. 59. The method of any one of numbered embodiments 45-58, wherein the first exposed end and the second exposed end are separated by at least 30 kb on the first DNA molecule prior to cleaving the first DNA molecule. 60. The method of any one of numbered embodiments 45-59, wherein the first exposed end and the second exposed end are separated by at least 50 kb on the first DNA molecule prior to cleaving the first DNA molecule. 61. The method of any one of numbered embodiments 45-60, wherein the first exposed end and the second exposed end are separated by at least 100 kb on the first DNA molecule prior to cleaving the first DNA molecule. 62. The method of any one of numbered embodiments 45-61, comprising sequencing a second copy of the first DNA molecule. 63. A rearranged nucleic acid molecule of at least 5 kb comprising a) a first segment; b) a second segment; and c) a third segment; d) said first segment and said second segment being joined at a first junction; and e) said second segment and said third segment being joined at a second junction; wherein said first segment, said second segment and said third segment exist in phase separated by at least 10 kb in an unrearranged nucleic acid molecule, and wherein at least 70% of said rearranged nucleic acid molecule maps to said common unrearranged nucleic acid molecule. 64. The rearranged nucleic acid of numbered embodiment 63, wherein the first segment, the second segment and the third segment comprise separate genomic nucleic acid sequence from a common nucleic acid molecule of a genome. 65. The rearranged nucleic acid of any one of numbered embodiments 63-64, wherein the first segment, the second segment and the third segment exist in a common molecule in the genome in an order that is rearranged in the rearranged nucleic acid. 66. The rearranged nucleic acid of any one of numbered embodiments 63-65, wherein said nucleic acid molecule is at least 30 kb in length. 67. The rearranged nucleic acid of any one of numbered embodiments 63-66, wherein said nucleic acid comprises a hairpin loop at a double-stranded terminal end, so that the molecule comprises a single strand comprising a 30 kb inverted repeat. 68. The rearranged nucleic acid of any one of numbered embodiments 63-67, wherein said nucleic acid is a double-stranded circular molecule. 69. The rearranged nucleic acid of any one of numbered embodiments 63-68, wherein at least 80% of said rearranged nucleic acid molecule maps to said common unrearranged nucleic acid molecule. 70. The rearranged nucleic acid of any one of numbered embodiments 63-69, wherein at least 85% of said rearranged nucleic acid molecule maps to said common unrearranged nucleic acid molecule. 71. The rearranged nucleic acid of any one of numbered embodiments 63-70, wherein at least 90% of said rearranged nucleic acid molecule maps to said common unrearranged nucleic acid molecule. 72. The rearranged nucleic acid of any one of numbered embodiments 63-71, wherein at least 95% of said rearranged nucleic acid molecule maps to said common unrearranged nucleic acid molecule. 73. The rearranged nucleic acid of any one of numbered embodiments 63-72, wherein at least 99% of said rearranged nucleic acid molecule maps to said common unrearranged nucleic acid molecule. 74. The rearranged nucleic acid of any one of numbered embodiments 63-73, wherein at least 80% of segments of said rearranged nucleic acid molecule maps to said common unrearranged nucleic acid molecule. 75. The rearranged nucleic acid of any one of numbered embodiments 63-74, wherein at least 85% of segments of said rearranged nucleic acid molecule maps to said common unrearranged nucleic acid molecule. 76. The rearranged nucleic acid of any one of numbered embodiments 63-75, wherein at least 90% of segments of said rearranged nucleic acid molecule maps to said common unrearranged nucleic acid molecule. 77. The rearranged nucleic acid of any one of numbered embodiments 63-76, wherein at least 95% of segments of said rearranged nucleic acid molecule maps to said common unrearranged nucleic acid molecule. 78. The rearranged nucleic acid of any one of numbered embodiments 63-77, wherein at least 99% of segments of said rearranged nucleic acid molecule maps to said common unrearranged nucleic acid molecule. 79. The rearranged nucleic acid of any one of numbered embodiments 63-78, wherein the rearranged nucleic acid is generated by steps of the method of any one or more of numbered embodiments 1-62. 80. A method of generating a phased sequence of a sample nucleic acid molecule comprising a) generating a first rearranged nucleic acid molecule of any one of numbered embodiments 63-78 from the sample nucleic acid molecule; b) generating a second rearranged nucleic acid molecule of any one of numbered embodiments 63-78 from the sample nucleic acid molecule; and c) sequencing the first rearranged nucleic acid molecule and the second rearranged nucleic acid molecule; wherein the first rearranged nucleic acid molecule and the second rearranged nucleic acid molecule are independently generated 81. A method of generating a phased sequence of a sample nucleic acid molecule comprising a) sequencing a first rearranged nucleic acid molecule of any one of numbered embodiments 63-78 from the sample nucleic acid molecule; b) sequencing a second rearranged nucleic acid molecule of any one of numbered embodiments 63-78 from the sample nucleic acid molecule; wherein the first rearranged nucleic acid molecule and the second rearranged nucleic acid molecule are independently generated; and c) assembling sequence of the first rearranged nucleic acid molecule of any one of numbered embodiments 63-78 and the second rearranged nucleic acid molecule of any one of numbered embodiments 63-78 such that an assembled sequence is an unrearranged phased sequence of a sample nucleic acid molecule. 82. The method of any one of numbered embodiments 80-81, wherein sequencing a first rearranged nucleic acid molecule comprises generating a sequence read of at least 1 kb. 83. The method of any one of numbered embodiments 80-82, wherein sequencing a first rearranged nucleic acid molecule comprises generating a sequence read of at least 2 kb. 84. The method of any one of numbered embodiments 80-83, wherein sequencing a first rearranged nucleic acid molecule comprises generating a sequence read of at least 5 kb. 85. The method of any one of numbered embodiments 80-84, comprising assigning at least 70% of said first rearranged molecule to a common phase of a single genomic molecule. 86. The method of any one of numbered embodiments 80-85, comprising assigning at least 70% of said second rearranged molecule to a common phase of a single genomic molecule. 87. The method of any one of numbered embodiments 80-86, comprising assigning at least 80% of said first rearranged molecule to a common phase of a single genomic molecule. 88. The method of any one of numbered embodiments 80-87, comprising assigning at least 80% of said second rearranged molecule to a common phase of a single genomic molecule. 89. The method of any one of numbered embodiments 80-88, comprising assigning at least 90% of said first rearranged molecule to a common phase of a single genomic molecule. 90. The method of any one of numbered embodiments 80-89, comprising assigning at least 90% of said second rearranged molecule to a common phase of a single genomic molecule. 91. The method of any one of numbered embodiments 80-90, comprising assigning at least 95% of said first rearranged molecule to a common phase of a single genomic molecule. 92. The method of any one of numbered embodiments 80-91, comprising assigning at least 95% of said second rearranged molecule to a common phase of a single genomic molecule. 93. A method of phasing long-read sequence data comprising a) obtaining sequence data from the nucleic acid sample of any one of numbered embodiments 63-78; b) obtaining long-read sequence data from the rearranged nucleic acid of any one of numbered embodiments 63-78; c) mapping the long-read sequence data from the rearranged nucleic acid of any one of numbered embodiments 63-78 to the sequence data from the nucleic acid sample; and d) assigning to a common phase the sequence data from the nucleic acid sample mapped to by the long-read sequence data from the rearranged nucleic acid of any one of numbered embodiments 63-78. 94. A method of providing phase information to a nucleic acid dataset generated from a nucleic acid sample by a DNA sequencing technology, comprising a) obtaining a nucleic acid of said nucleic acid sample having a first segment and a second segment separated by a distance greater than a read length of the DNA sequencing technology b) shuffling the nucleic acid such that the first segment and the second segment are separated by a distance less than a read length of the DNA sequencing technology; c) sequencing the shuffled nucleic acid using the DNA sequencing technology such that the first segment and the second segment appear in a single read of the DNA sequencing technology; and d) assigning sequence reads of the data set comprising first segment sequence and sequence reads of the data set comprising second segment sequence to a common phase. 95. The method of numbered embodiment 94, wherein the DNA sequencing technology generates reads having a read length of at least 10 kb. 96. The method of any one of numbered embodiments 94-94, wherein shuffling comprises performing steps of any one of any one of numbered embodiments 1-62. 97. The method of any one of numbered embodiments 94-94, wherein the first segment and the second segment are separated by a linker oligo that marks a segment end. 98. A nucleic acid sequence database comprising sequence information obtained from a plurality of molecules of any one of numbered embodiments 63-78, wherein sequence information corresponding to molecules having less than 70% of their segments map to a common scaffold is excluded from at least one analysis. 99. A nucleic acid sequence database comprising sequence information obtained from a plurality of molecules of any one of numbered embodiments 63-78, wherein sequence information corresponding to molecules having less than 70% of their sequence information map to a common scaffold is excluded from at least one analysis. 100. A method of phasing long-read sequence data comprising a) obtaining sequence data from the nucleic acid sample of any one of numbered embodiments 63-78; b) obtaining long-read sequence data from the rearranged nucleic acid of the rearranged nucleic acid of any one of numbered embodiments 63-78; c) mapping the first segment, the second segment and the third segment of the rearranged nucleic acid of any one of numbered embodiments 63-78 to the sequence data from the nucleic acid sample to the nucleic acid sample sequence data; and d) when at least two segments map to a common scaffold, assigning sequence variation of said segments to a common phase. 101. The method of numbered embodiment 100, wherein the first segment comprises a single nucleotide polymorphism relative to the sequence data from the nucleic acid sample. 102. The method of any one of numbered embodiments 100-101, wherein the first segment comprises an insertion relative to the sequence data from the nucleic acid sample. 103. The method of any one of numbered embodiments 100-102, wherein the first segment comprises a deletion relative to the sequence data from the nucleic acid sample. 104. The method of any one of numbered embodiments 100-103, comprising assigning a first set of segments mapping to a first common scaffold to a common phase of the first common scaffold, and assigning a second set of segments mapping to a second common scaffold to a common phase of the second common scaffold. 105. A nucleic acid sequence library of a nucleic acid sample, said nucleic acid sequence library comprising a population of nucleic acid sequence reads having an average read length, at least one of said reads comprising at least 500 bases of a first nucleic acid segment and at least 500 bases of a second nucleic acid segment, wherein said first nucleic acid segment and said second nucleic acid segment are found in phase separated by a distance greater than said average read length on a common molecule of said nucleic acid sample. 106. The nucleic acid sequence library of numbered embodiment 105, wherein said first nucleic acid segment and said second nucleic acid segment are found in phase separated by a distance greater than 10 kb. 107. The nucleic acid sequence library of any one of numbered embodiments 105-106, wherein said first nucleic acid segment and said second nucleic acid segment are found in phase separated by a distance greater than 20 kb. 108. The nucleic acid sequence library of any one of numbered embodiments 105-107, wherein said first nucleic acid segment and said second nucleic acid segment are found in phase separated by a distance greater than 50 kb. 109. The nucleic acid sequence library of any one of numbered embodiments 105-108, wherein said first nucleic acid segment and said second nucleic acid segment are found in phase separated by a distance greater than 100 kb. 110. The nucleic acid sequence library of any one of numbered embodiments 105-109, wherein at least one of said reads comprises at least 1 kb of a first nucleic acid segment. 111. The nucleic acid sequence library of any one of numbered embodiments 105-110, wherein at least one of said reads comprises at least 5 kb of a first nucleic acid segment. 112. The nucleic acid sequence library of any one of numbered embodiments 105-111, wherein at least one of said reads comprises at least 10 kb of a first nucleic acid segment. 113. The nucleic acid sequence library of any one of numbered embodiments 105-112, wherein at least one of said reads comprises at least 20 kb of a first nucleic acid segment. 114. The nucleic acid sequence library of any one of numbered embodiments 105-113, wherein at least one of said reads comprises at least 50 kb of a first nucleic acid segment. 115. The nucleic acid sequence library of any one of numbered embodiments 105-114, wherein nucleic acid sequence library comprises at least 80% of said nucleic acid sample. 116. The nucleic acid sequence library of any one of numbered embodiments 105-115, wherein nucleic acid sequence library comprises at least 85% of said nucleic acid sample. 117. The nucleic acid sequence library of any one of numbered embodiments 105-116, wherein nucleic acid sequence library comprises at least 90% of said nucleic acid sample. 118. The nucleic acid sequence library of any one of numbered embodiments 105-117, wherein nucleic acid sequence library comprises at least 95% of said nucleic acid sample. 119. The nucleic acid sequence library of any one of numbered embodiments 105-118, wherein nucleic acid sequence library comprises at least 99% of said nucleic acid sample. 120. The nucleic acid sequence library of any one of numbered embodiments 105-119, wherein nucleic acid sequence library comprises at least 99.9% of said nucleic acid sample. 121. A nucleic acid sequence library of a nucleic acid sample, said nucleic acid sequence library comprising a population of nucleic acid sequence reads having a mean length of at least 1 kb, said reads independently comprising at least 300 bases of sequence from two separate in phase regions of the nucleic acid sample, said two separate in phase regions separated by a distance greater than 10 kb in the nucleic acid sample. 122. The nucleic acid sequence library of numbered embodiment 121, wherein said reads independently comprise at least 500 bases of sequence from two separate in phase regions of the nucleic acid sample. 123. The nucleic acid sequence library of any one of numbered embodiments 121-122, wherein said reads independently comprise at least 1 kb of sequence from two separate in phase regions of the nucleic acid sample. 124. The nucleic acid sequence library of any one of numbered embodiments 121-123, wherein said reads independently comprise at least 2 kb of sequence from two separate in phase regions of the nucleic acid sample. 125. The nucleic acid sequence library of any one of numbered embodiments 121-124, wherein said reads independently comprise at least 5 kb of sequence from two separate in phase regions of the nucleic acid sample. 126. The nucleic acid sequence library of any one of numbered embodiments 121-125, wherein said reads independently comprise at least 10 kb of sequence from two separate in phase regions of the nucleic acid sample. 127. The nucleic acid sequence library of any one of numbered embodiments 121-126, wherein said two separate in phase regions are separated by a distance greater than 20 kb in the nucleic acid sample. 128. The nucleic acid sequence library of any one of numbered embodiments 121-127, wherein said two separate in phase regions are separated by a distance greater than 30 kb in the nucleic acid sample. 129. The nucleic acid sequence library of any one of numbered embodiments 121-128, wherein said two separate in phase regions are separated by a distance greater than 50 kb in the nucleic acid sample in at least 1% of the reads. 130. The nucleic acid sequence library of any one of numbered embodiments 121-129, wherein said two separate in phase regions are separated by a distance greater than 100 kb in the nucleic acid sample in at least 1% of the reads. 131. The nucleic acid sequence library of any one of numbered embodiments 121-130, wherein nucleic acid sequence library comprises at least 80% of said nucleic acid sample. 132. The nucleic acid sequence library of any one of numbered embodiments 121-131, wherein nucleic acid sequence library comprises at least 85% of said nucleic acid sample. 133. The nucleic acid sequence library of any one of numbered embodiments 121-132, wherein nucleic acid sequence library comprises at least 90% of said nucleic acid sample. 134. The nucleic acid sequence library of any one of numbered embodiments 121-133, wherein nucleic acid sequence library comprises at least 95% of said nucleic acid sample. 135. The nucleic acid sequence library of any one of numbered embodiments 121-134, wherein nucleic acid sequence library comprises at least 99% of said nucleic acid sample. 136. The nucleic acid sequence library of any one of numbered embodiments 121-135, wherein nucleic acid sequence library comprises at least 99.9% of said nucleic acid sample. 137. A nucleic acid library generated from a nucleic acid sample, wherein at least 80% of nucleic acid sequence of the nucleic acid sample is represented in the nucleic acid library; and in phase sequence segments of the nucleic acid sample are rearranged such that at least one distantly positioned pair of in phase segments of the nucleic acid sample is read in a single sequence read; such that sequencing said library concurrently generates contig information spanning at least 80% of the nucleic acid sample, and phase information sufficient to order and orient said contig information to generate a phased sequence of said nucleic acid sample. 138. The nucleic acid library of numbered embodiment 137, wherein at least 90% of nucleic acid sequence of the nucleic acid sample is represented in the nucleic acid library. 139. The nucleic acid library of any one of numbered embodiments 137-138, wherein at least 95% of nucleic acid sequence of the nucleic acid sample is represented in the nucleic acid library. 140. The nucleic acid library of any one of numbered embodiments 137-139, wherein at least 99% of nucleic acid sequence of the nucleic acid sample is represented in the nucleic acid library. 141. The nucleic acid library of any one of numbered embodiments 137-140, wherein said 80% of nucleic acid sequence of the nucleic acid sample is obtained from no more than 100,000 library constituents. 142. The nucleic acid library of any one of numbered embodiments 137-141, wherein said 80% of nucleic acid sequence of the nucleic acid sample is obtained from no more than 10,000 library constituents. 143. The nucleic acid library of any one of numbered embodiments 137-142, wherein said 80% of nucleic acid sequence of the nucleic acid sample is obtained from no more than 1,000 library constituents. 144. The nucleic acid library of any one of numbered embodiments 137-143, wherein said 80% of nucleic acid sequence of the nucleic acid sample is obtained from no more than 500 library constituents. 145. The nucleic acid library of any one of any one of numbered embodiments 137-144, wherein the sample is a genomic sample. 146. The nucleic acid library of any one of any one of numbered embodiments 137-145, wherein the sample is a eukaryotic genomic sample. 147. The nucleic acid library of any one of any one of numbered embodiments 137-146, wherein the sample is a plant genomic sample. 148. The nucleic acid library of any one of any one of numbered embodiments 137-147, wherein the sample is an animal genomic sample. 149. The nucleic acid library of any one of any one of numbered embodiments 137-148, wherein the sample is a mammalian genomic sample. 150. The nucleic acid library of any one of any one of numbered embodiments 137-149, wherein the sample is a unicellular eukaryotic genomic sample. 151. The nucleic acid library of any one of any one of numbered embodiments 137-150, wherein the sample is a human genomic sample. 152. The nucleic acid library of any one of numbered embodiments 137-151, wherein the nucleic acid library is not barcoded to preserve phase information. 153. The nucleic acid library of any one of numbered embodiments 137-152, wherein a read of said library comprises at least 1 kb of sequence from a first region and at least 100 bases of sequence from a second region in phase the first region and separated by greater than 50 kb from the first region in the sample. 154. A method of configuring a nucleic acid molecule for sequencing on a sequencing device, wherein the nucleic acid molecule comprises at least 100 kb of sequence, and wherein said at least 100 kb of sequence comprises a first segment and a second segment separated by a length greater than a read length of the sequencing device, comprising changing a relative position of the first segment relative to the second segment of the nucleic acid molecule, such that the first segment and the segment are separated by less than the read length of the sequencing device; wherein phase information for the first segment and the second segment is maintained; and wherein no more than 10% of the nucleic acid molecule is deleted. 155. The method of numbered embodiment 154, comprising generating a read spanning at least part of the first segment and the second segment. 156. The method of any one of numbered embodiments 154-155, comprising assigning the first segment and the second segment to a common phase of a sequence of the nucleic acid molecule. 157. The method of any one of numbered embodiments 154-156, wherein no more than 5% of the nucleic acid molecule is deleted. 158. The method of any one of numbered embodiments 154-157, wherein no more than 1% of the nucleic acid molecule is deleted. 159. The method of any one of numbered embodiments 154-158, wherein the first segment and the second segment are separated by at least 10 kb in the nucleic acid molecule prior to configuring. 160. The method of any one of numbered embodiments 154-159, wherein the first segment and the second segment are separated by at least 50 kb in the nucleic acid molecule prior to configuring. 161. The method of any one of numbered embodiments 154-160, wherein the first segment and the second segment are separated by a junction marker following said configuring. 162. The method of any one of numbered embodiments 154-161, comprising attaching a stem loop at an end of the nucleic acid, thereby converting the molecule to a single strand. 163. The method of any one of numbered embodiments 154-162, comprising circularizing the nucleic acid molecule. 164. The method of any one of numbered embodiments 154-163, comprising attaching the nucleic acid molecule to a DNA polymerase. 165. The method of any one of numbered embodiments 154-164, comprising binding the nucleic acid molecule such that the first segment and the second segment are held together independent of a phosphodiester backbone; cleaving a phosphodiester backbone between the first segment and the second segment at at least two positions; and reattaching the first segment to the second segment, such that the first segment and the second segment are separated by less than a read length of the sequencing device. 166. The method of any one of numbered embodiments 154-165, wherein said cleaving and said reattaching does not result in loss of sequence information form said nucleic acid molecule. 167. A method of generating long-distance phase information from a first nucleic acid molecule, comprising: a) providing a sample comprising a first nucleic acid molecule having a first segment, a second segment, and a third segment, wherein none of the first segment, the second segment, and the third segment are adjacent on the first nucleic acid molecule, wherein the first nucleic acid molecule is contacted to a framework such that the first segment, the second segment, and the third segment are bound to the framework independent of a common phosphodiester backbone of the first nucleic acid molecule; b) cleaving the first nucleic acid molecule such that the first segment, the second segment, and the third segment are not joined by a common phosphodiester backbone; c) connecting the first segment to the second segment and connecting the second segment to the third segment; and d) sequencing a first portion of the first nucleic acid molecule comprising the first segment, the second segment, and the third segment, thereby generating first segment sequence information, second segment sequence information, and third segment sequence information, wherein the first segment sequence information, the second segment sequence information, and the third segment sequence information provide long-distance phase information about the first nucleic acid molecule. 168. The method of numbered embodiment 167, wherein the framework comprises reconstituted chromatin. 169. The method of any one of numbered embodiments 167-168, wherein the framework comprises native chromatin. 170. The method of any one of numbered embodiments 167-169, wherein the cleaving is conducted with a restriction enzyme. 171. The method of any one of numbered embodiments 167-170, wherein the cleaving is conducted with fragmentase. 172. The method of any one of numbered embodiments 167-171, further comprising, prior to the sequencing, removing from the sample a second portion of the first nucleic acid molecule comprising at most two segments. 173. The method of any one of numbered embodiments 167-172, further comprising assembling a sequence of the first nucleic acid molecule using the first segment sequence information, the second segment sequence information, and the third segment sequence information. 174. A method of sequencing a nucleic acid molecule, comprising: obtaining a first nucleic acid molecule comprising a first segment, a second segment and a third segment sharing a common phosphodiester backbone, wherein none of said first segment, second segment and third segment are adjacent on said first nucleic acid molecule; partitioning said nucleic acid molecule such that said first segment, second segment and third segment are associated independent of their common phosphodiester backbone; cleaving said nucleic acid molecule to generate fragments such that there is no continuous phosphodiester backbone linking the first segment, second segment and third segment; ligating said fragments such that said first segment, second segment and third segment are consecutive on a rearranged nucleic acid molecule sharing a common phosphodiester backbone; and sequencing at least a portion of said rearranged nucleic acid molecule such that at least 5,000 bases of said rearranged nucleic acid molecule are sequenced in a single read. 175. The method of numbered embodiment 174, wherein partitioning comprises contacting said nucleic acid molecule to a binding moiety such that said first segment, second segment and third segment are bound in a common complex independent of their common phosphodiester backbone. 176. The method of any one of numbered embodiments 174-175, wherein contacting the nucleic acid molecule to a plurality of DNA-binding molecules comprises contacting to a population of DNA-binding proteins. 177. The method of any one of numbered embodiments 174-176, wherein the population of DNA-binding proteins comprises nuclear proteins. 178. The method of any one of numbered embodiments 174-177, wherein the population of DNA-binding proteins comprises nucleosomes. 179. The method of any one of numbered embodiments 174-178, wherein the population of DNA-binding proteins comprises histones. 180. The method of any one of numbered embodiments 174-179, wherein contacting the nucleic acid molecule to a plurality of DNA-binding moieties comprises contacting to a population of DNA-binding nanoparticles. 181. The method of any one of numbered embodiments 174-180, wherein cleaving the nucleic acid molecule comprises contacting to a restriction endonuclease. 182. The method of any one of numbered embodiments 174-181, wherein cleaving the nucleic acid molecule comprises contacting to a nonspecific endonuclease. 183. The method of any one of numbered embodiments 174-182, wherein cleaving the nucleic acid molecule comprises contacting to a tagmentation enzyme. 184. The method of any one of numbered embodiments 174-183, wherein cleaving the nucleic acid molecule comprises contacting to a transposase. 185. The method of any one of numbered embodiments 174-184, wherein cleaving the nucleic acid molecule comprises shearing the first molecule. 186. The method of any one of numbered embodiments 174-185, wherein partitioning comprises separating said nucleic acid molecule from other nucleic acid molecules of a sample. 187. The method of any one of numbered embodiments 174-186, wherein partitioning comprises diluting said nucleic acid sample. 188. The method of any one of numbered embodiments 174-187, wherein partitioning comprises distributing said nucleic acid molecule into a microdroplet of an emulsion. 189. A nucleic acid molecule representative of genomic phase information of an organisms's genome, said nucleic acid molecule comprising at least 20 kb of nucleic acid sequence information that maps to a single genomic molecule, wherein said sequence information comprises segments rearranged relative to their position in the genomic molecule, and wherein at least 70% of sequence information that uniquely maps to said organism's genome maps to a single genomic molecule. 190. The nucleic acid molecule of numbered embodiment 189, wherein the nucleic acid molecule comprises at least 20 segments. 191. The nucleic acid molecule of any one of numbered embodiments 189-190, wherein said segments are not adjacent in said organism's genome. 192. A nucleic acid library comprising at least 100 nucleic acid molecule constituents of at least 20 kb, wherein constituents comprise rearranged segments of an organism's genome; wherein at least 70% of uniquely mapping segments from a library constituent map to a common genomic molecule; and wherein constituents are not bound to nucleic acid binding moieties. 193. A nucleic acid dataset comprising sequences corresponding to at least 100 nucleic acid molecule constituents of at least 20 kb, wherein constituents comprise at least 5 rearranged segments of an organism's genome, and wherein constituents for which less than 70% of said rearranged segments map to a common scaffold are excluded from a downstream analysis. 194. A nucleic acid dataset comprising sequences corresponding to at least 100 nucleic acid molecule constituents of at least 20 kb, wherein constituents comprise at least 5 rearranged segments of an organism's genome, and wherein constituents for which less than 70% of said sequence uniquely maps to a common scaffold are excluded from a downstream analysis.

Referring to the Figures, one sees illustration of certain embodiments discussed herein. At FIG. 1, one sees an intermediate in the process of constructing a punctuated, rearranged phase-preserving nucleic acid molecule. A single nucleic acid molecule has been bound to a nucleic acid binding moiety, such as a reconstituted chromatin complex, and contacted to formaldehyde to crosslink the complex. The complex involves a single nucleic acid starting molecule, which forms a cluster with the nucleic acid-binding components, collectively referred to as reconstituted chromatin, such that only internal loops of the nucleic acid molecule protrude from the cluster. The protruding loops are cleaved using the restriction endonuclease MboI to generate sticky ends, as depicted in FIG. 1.

In alternate embodiments, the nucleic acid molecule is bound to a bead or surface, such as a SPRI coated or other nucleic acid-binding agent coated bead. The nucleic acid sample is bound under conditions such that only one nucleic acid molecule is bound per bead, or such that bound nucleic acids are unlikely to cross-ligate after cleavage. Also, cleavage is alternately accomplished using another restriction endonuclease, a transposase, a tagmentation enzyme, a non-specific endonuclease, a topoisomerase or other agent having endonuclease activity.

At FIG. 2, one sees that the cleaved nucleic acid complex of FIG. 1 is treated using a nucleic acid polymerase and a single population of dGTP so as to fill in a single position of the overhang. The fill-in step prevents sticky ends of the complex from cross-annealing and ligating in a later step. In some cases, the step is excluded, and complexes are allowed to cross-ligate without punctuation oligos. Alternately, blunt ends are generated, or tagmentation adapters are added though the action of a transposase rather than a restriction endonuclease.

FIG. 3 shows the complex of FIG. 1 and FIG. 2 following annealing and ligation of punctuation oligos to the exposed ends of the complex. Punctuation oligos are depicted as thin solid lines rather than as nucleic acid base sequence. Punctuation oligos are optionally modified so as to preclude concatemerization, for example by removal of 5' phosphate groups. Punctuation oligos are optionally designed to be compatible with the free sticky ends as modified in FIG. 2. In other embodiments, cleaved nucleic acid ends can be ligated to each other directly, without intervening punctuation oligos.

Figure 4:
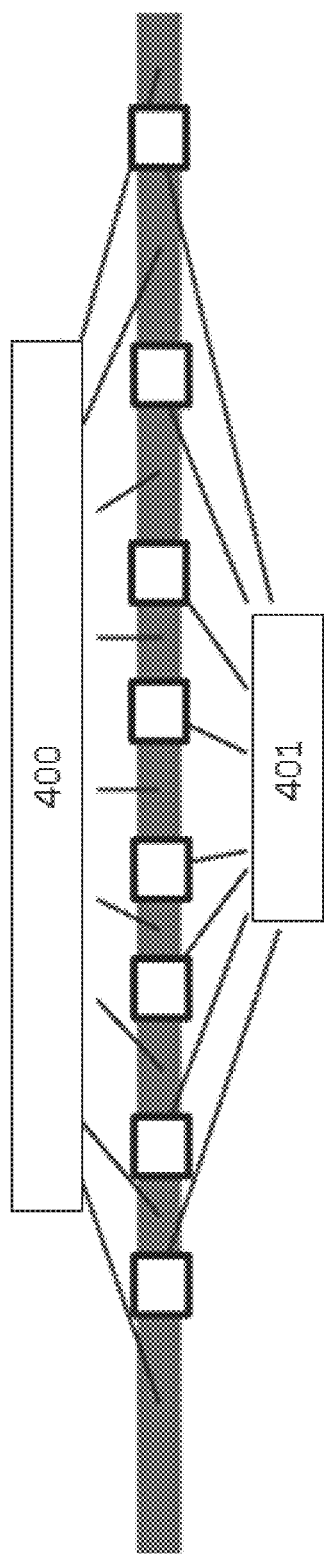
FIG. 4 depicts a punctuated DNA molecule resulting from the ligation product of FIG. 3 followed by release from the DNA-binding proteins. Each genomic segment is delineated by the punctuation oligonucleotide which is identifiable by its known sequence. The genomic segments all represent some region of the input molecule in that starting reconstituted chromatin aggregate. Thus, the reads in this set are haplotype phased and can be used for assembly or haplotype phase reconstruction.

FIG. 4 depicts the released punctuated nucleic acid molecule following reversal of crosslinking and liberation from the reconstituted chromatin through treatment using proteinase K. The end-product punctuated nucleic acid comprises segments 400 separated by punctuation oligos 401. The segments preserve the phase information of the original nucleic acid molecule but are randomly ordered and oriented relative to the beginning molecule. Substantially all of the sequence of the original nucleic acid molecule is present in the punctuated molecule, such that sequencing the punctuated molecule generates sequence information sufficient to generate de novo contigs.

Upon sequencing the punctuated nucleic acid using a long-read sequencing device, one observes stretches of sequence that correspond to uncleaved segments, for which local order and orientation, as well as phase information is derived. One also observes regions of long sequence reads that span punctuation oligo sequence. These sequence segments on either side of a punctuation oligo are known to be in phase with one another (and in phase with other segments on the punctuated molecule), but are unlikely to be in the correct order and orientation. A benefit of the rearrangement process is that segments far apart from one another on the sample molecule are brought into proximity such that they are spanned in a single read. Another benefit is that the sequence information of the original sample molecule is largely preserved, such that de novo contig information is concurrently generated.

Figure 5:
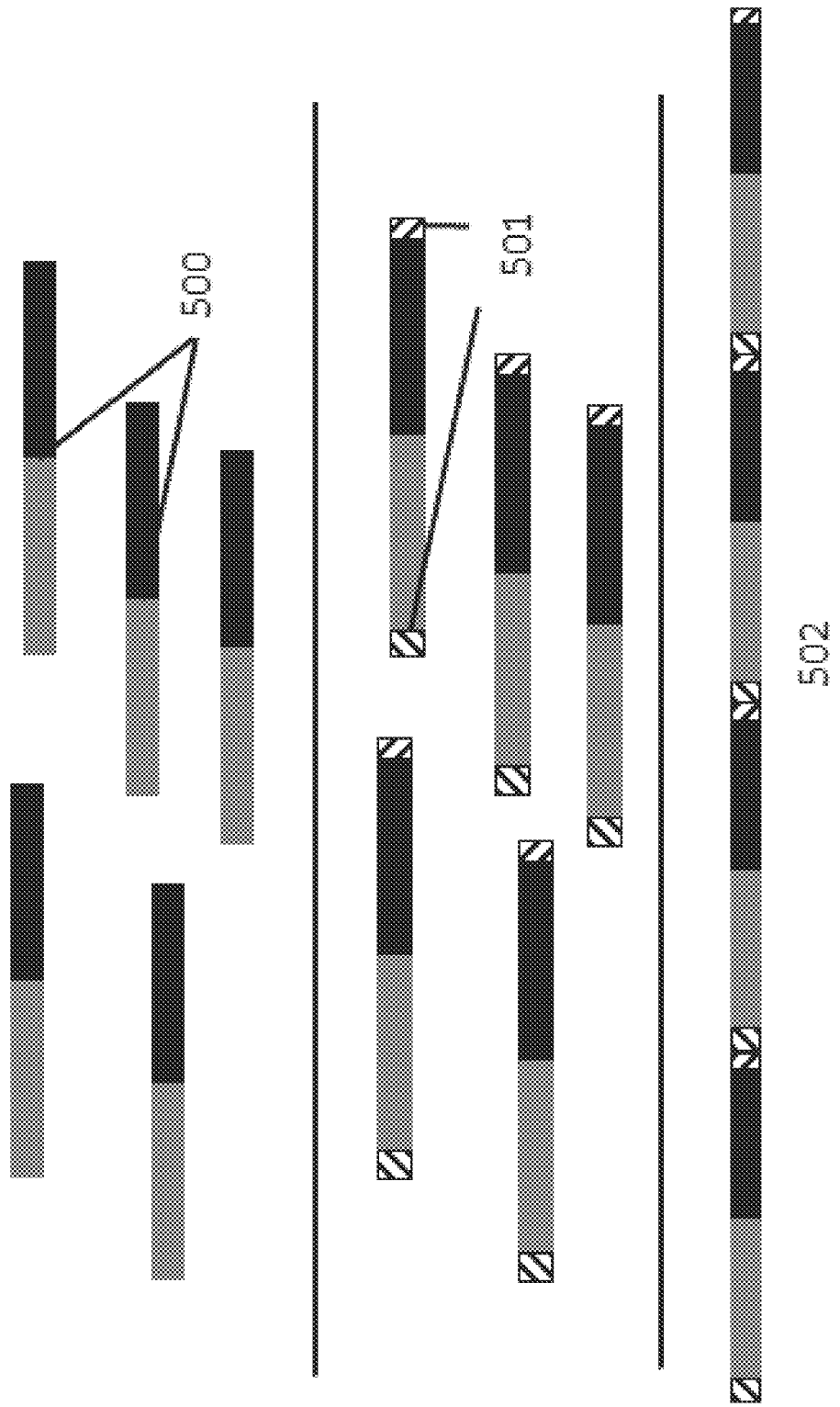
FIG. 5 depicts concatemer generation of Chicago pairs. In the top panel, Chicago read pairs are generated by ligating biotinylated ends of digested reconstituted chromatin aggregates together (such as the ends in FIG. 1 if they were biotinylated and cleaved following ligation). These molecules are captured on streptavidin-coated beads. Then, amplification adapters are added. All molecules are bulk amplified and collected from the streptavidin-bead supernatant. Finally, these molecules are bulk ligated together to generate long molecules which can be read using a long-read sequencing technology. The embedded read pairs are identifiable via the amplification adapters.

FIG. 5 shows an alternative embodiment of the present disclosure. A series of short paired ends 500, each indicative that the sequences joined in the pair are in phase, are adapter tagged (e.g., with amplification adapters) 501 and ligated to form a concatenated paired end multimer 502. Individual pairs, or contigs to which they uniquely map, are confidently assigned to a common phase. Read pair units on either side of amplification adapters are not inferred to have an order, orientation, or phase relationship with one another unless additional measures are taken in concatemer assembly.

A benefit of the concatenated molecule of FIG. 5 is that multiple paired end reads are assembled into a single molecule that is sequenced in a single or a smaller number of long read reactions, rather than in a much greater number of short-run reads. However, because the segment length of individual paired ends is shorter, the overall sequence of the staring sample is unlikely to be preserved in the concatenated molecule, complicating de novo sequencing.

Figure 6:
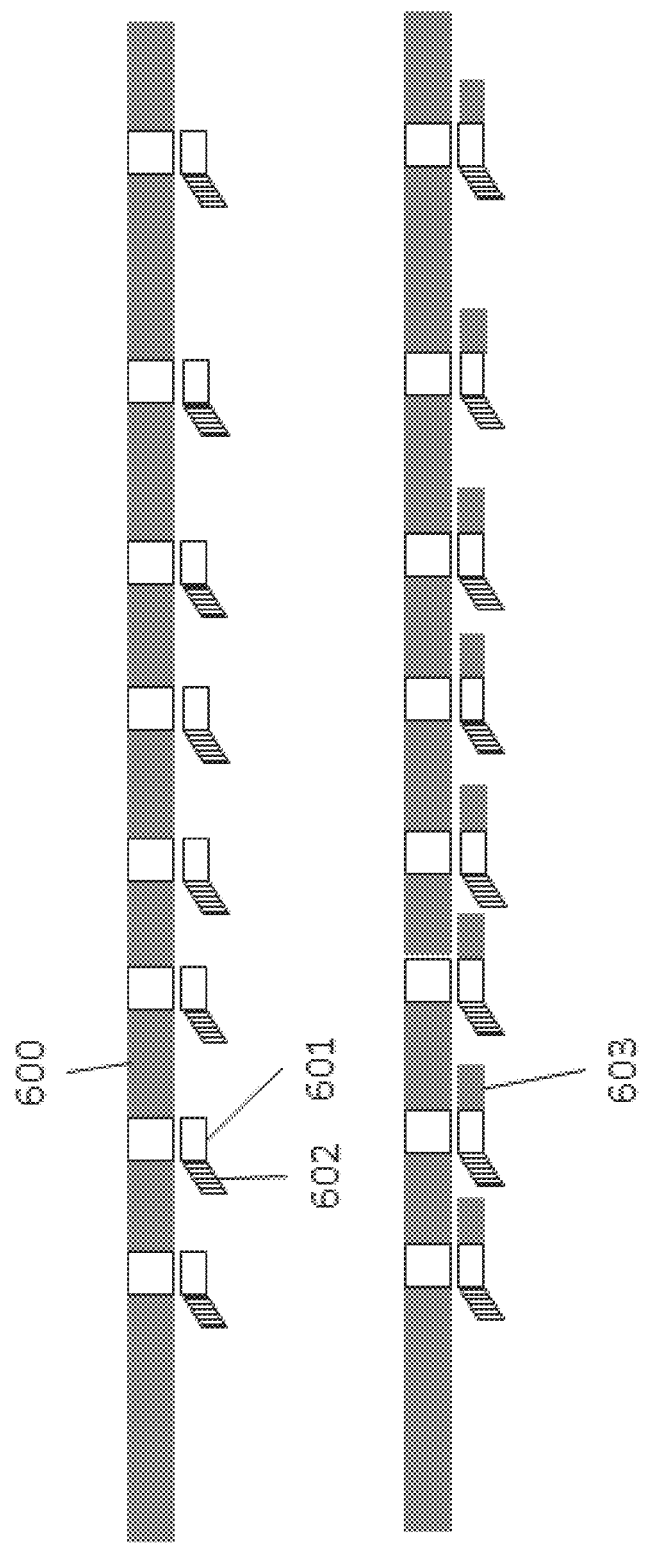
FIG. 6 depicts barcoding a punctuated molecule, such as the molecule depicted in FIG. 4 or the long molecule generated in FIG. 5. First, delivery of barcoded oligonucleotides that are composed of a barcode and a reverse complement to the punctuation oligonucleotide is done. Then, these barcoded oligonucleotides are extended such that the product contains the barcode, the punctuation sequence and some genomic sequence.

FIG. 6 shows an alternative scenario, whereby a punctuated nucleic acid molecule 600 is used to generate templates for short-read sequencing. Punctuated nucleic acid molecules are contacted to a population of primers 601 that anneal to the punctuation sequence and that comprise bin-specific oligonucleotide barcodes 602. The primers can then be extended, for example, to incorporate sequence 603 complementary to the punctuated nucleic acid molecule. Through this approach, phase information is derived from the barcode information. A benefit is that short-read sequencing is facilitated.

Figure 7:
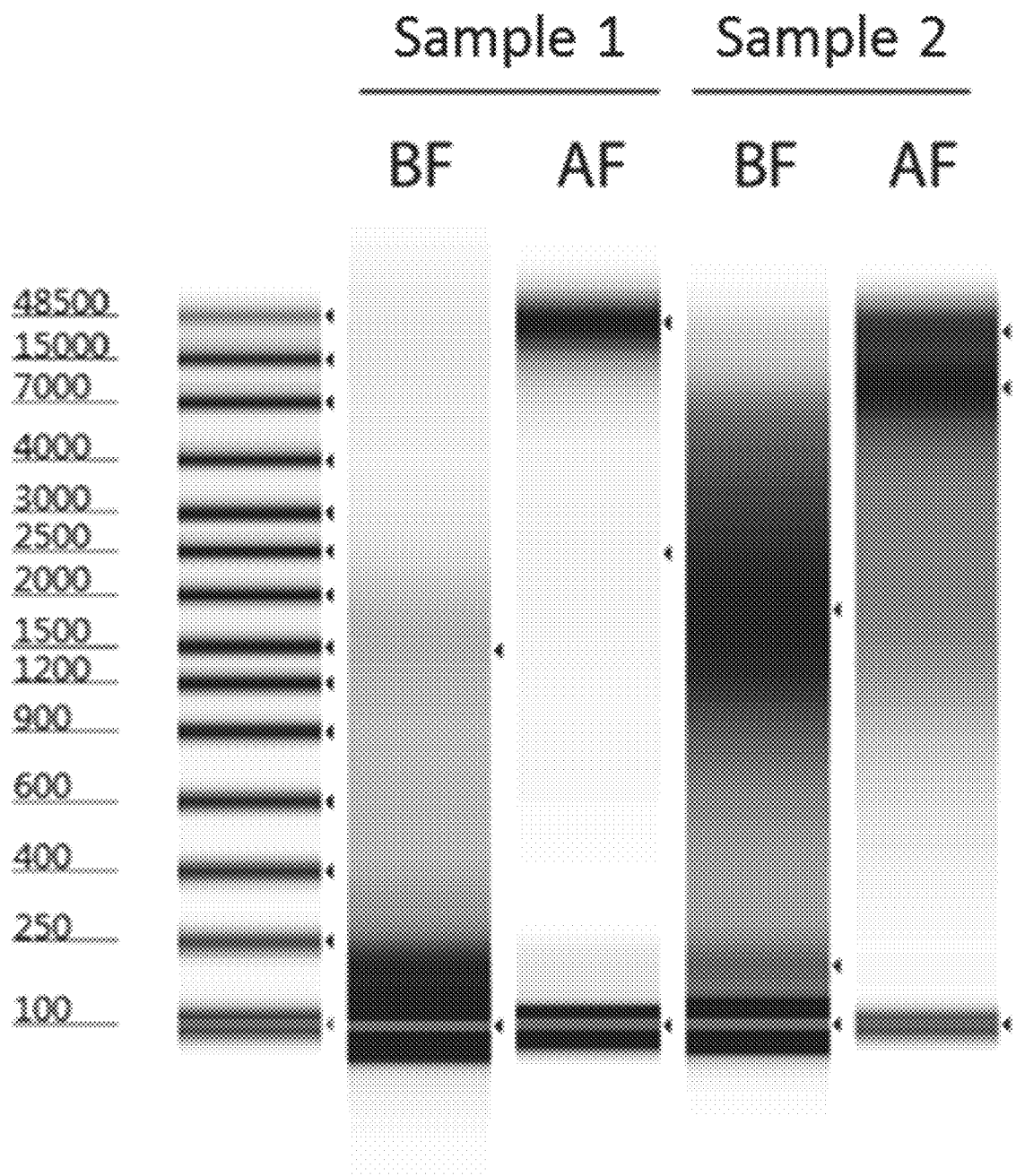
FIG. 7 depicts a gel electrophoresis analysis of two samples, before the ligation step ('BF') and after the ligation step ('AF'), demonstrating successful ligation to form long rearranged molecules.

FIG. 7 shows a gel electrophoresis analysis of two samples, before a ligation step ('BF') and after a ligation step ('AF'). The left-most lane contains a DNA ladder, with sizes from top to bottom of 48500, 15000, 7000, 4000, 3000, 2500, 2000, 1500, 1200, 900, 600, 400, 250, and 100 bp. The second and third lanes from the left contain sample 1 before and after ligation, respectively. The fourth and fifth lanes from the left contain sample 2 before and after ligation, respectively. Both the sample 1 and sample 2 ligated lanes show dark bands of DNA in the 7000-48500 bp range, much larger than the bands in either of the pre-ligation lanes. Sample 1 comprises about 7 nanograms DNA per microliter (ng/µL) with a total of about 200 ng DNA, and sample 2 comprises about 115 µg/µL of DNA, with a total of about 3.4 g DNA.

Figure 8:
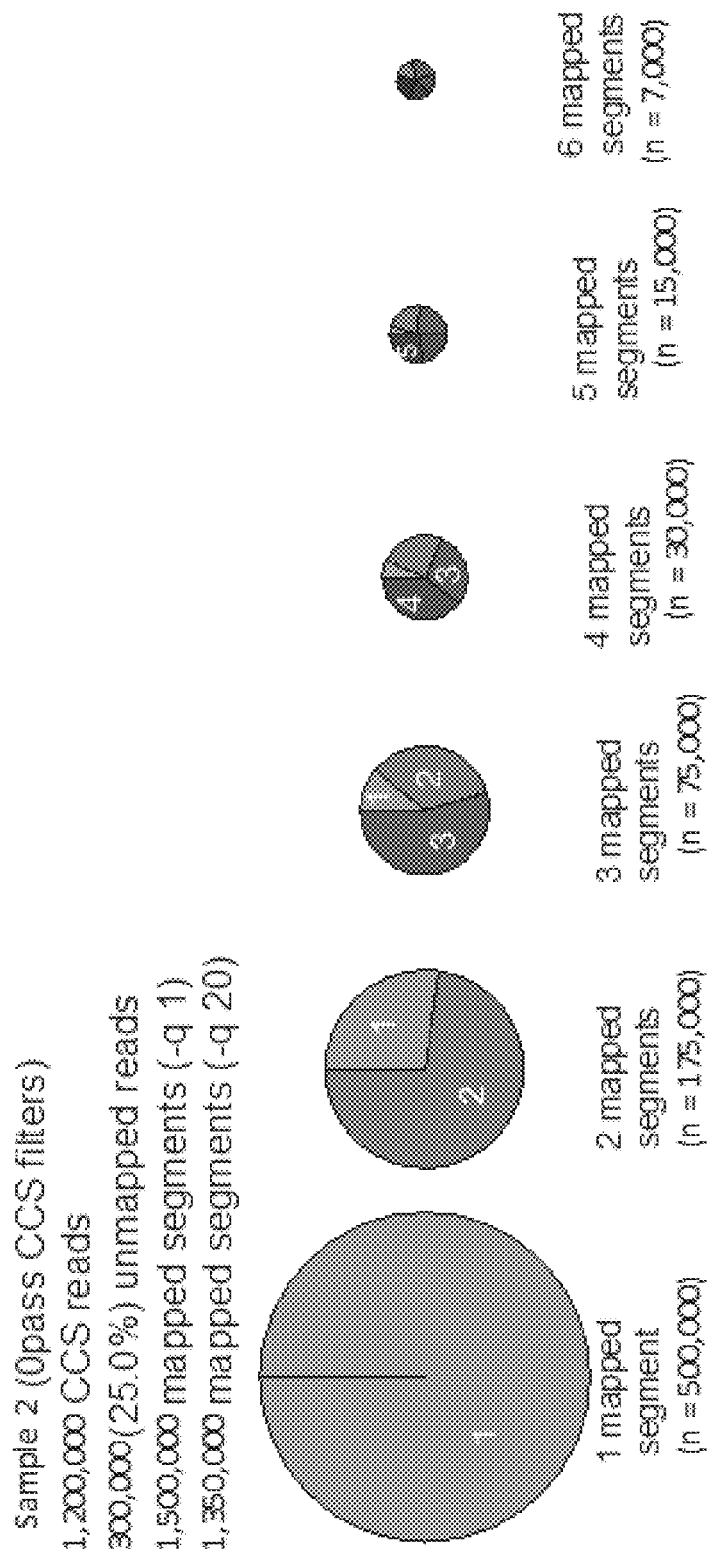
FIG. 8 presents data obtained from a rearranged genomic library.

FIG. 8 presents representative information about the sequencing information for a sample. Over 1,000,000 circular consensus sequence (CSS) reads are generated, with 300,000 unmapped reads (25%). There are 1,500,000 mapped segments (-q 1) and 1,350,000 mapped segments (-q 20). For reads with 1 mapped segment, n=500,000; for reads with 2 mapped segments, n=175,000; for reads with 3 mapped segments, n=75,000; for reads with 4 mapped segments, n=30,000; for reads for 5 mapped segments, n=15,000; for reads with 6 mapped segments, n=7,000. Table 1 shows clone coverage from reads with X maximum number of mapping segments.

Figure 9:
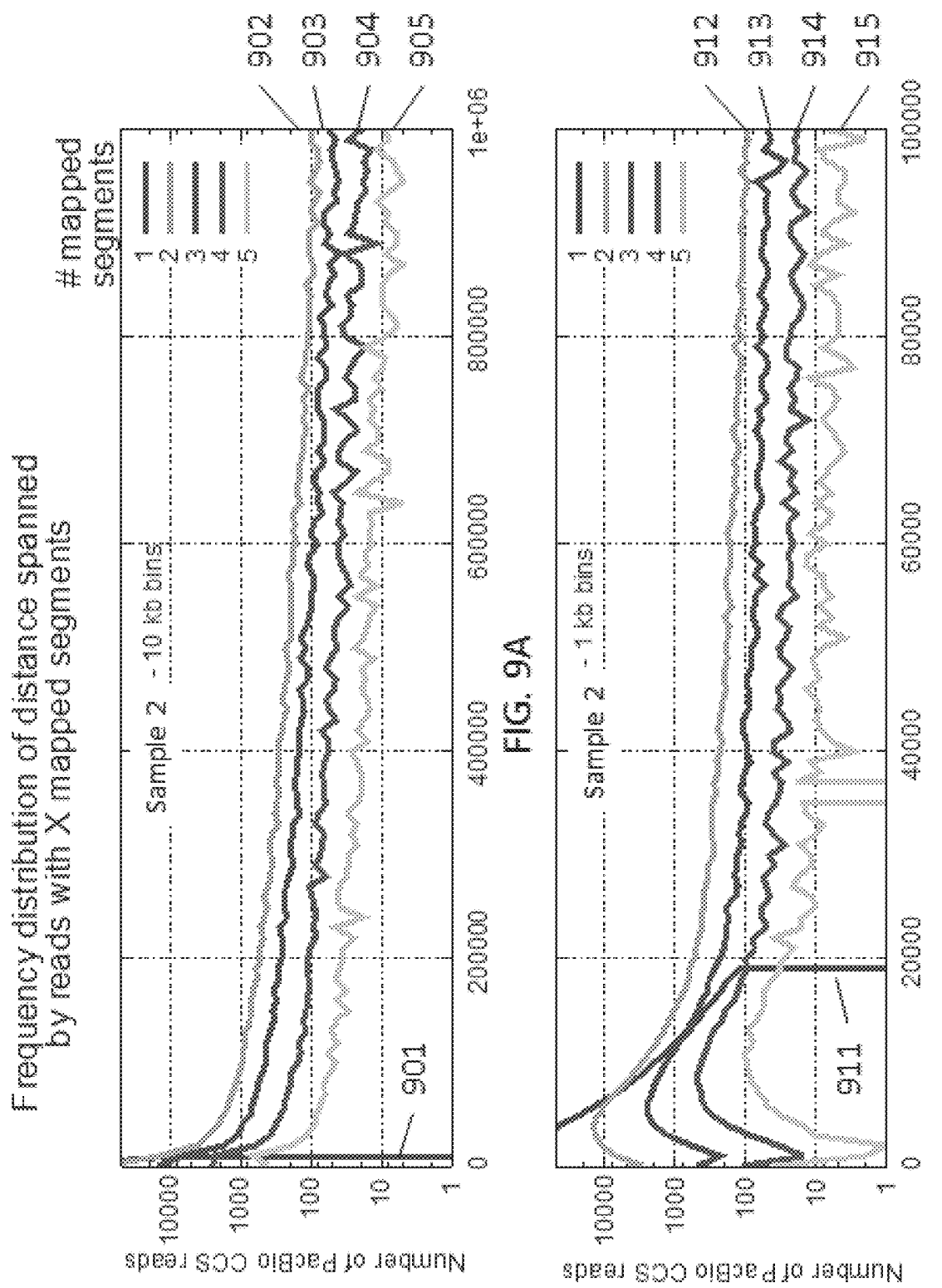
FIG. 9A depicts frequency distributions of distance spanned by reads segregated into 10 kb bins.
FIG. 9B depicts frequency distributions of distance spanned by reads segregated into 1 kb bins.

FIG. 9A and FIG. 9B show frequency distributions of distance spanned by reads with X mapped segments for a sample, with 10 kb bins (FIG. 9A) and 1 kb bins (FIG. 9B). The y axis shows the number of PacBio CCS reads (axis lines from bottom to top: 1, 10, 100, 1000, 10000). The x axis shows the distance spanned by the reads (axis lines from left to right: FIG. 9A: 0, 200000, 400000, 600000, 800000, 1000000; FIG. 9B: 0, 20000, 40000, 60000, 80000, 100000). Frequency distributions are shown for reads with 1 mapped segment (901, 911), 2 mapped segments (902, 912), 3 mapped segments (903, 913), 4 mapped segments (904, 914), and 5 mapped segments (905, 915).

Figure 10:
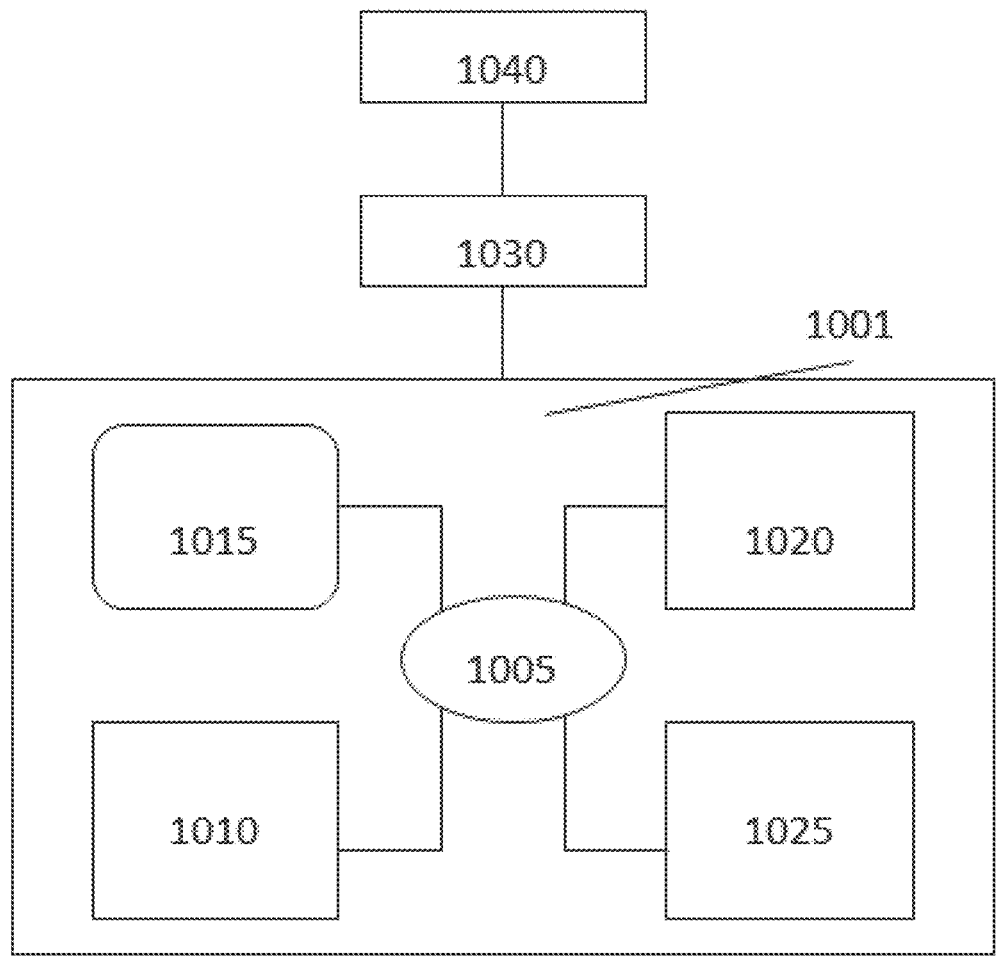
FIG. 10 depicts a computer system for implementation of the disclosure.

FIG. 10 depicts an exemplary computer system 1000 adapted to implement a method described herein. The system 1000 includes a central computer server 1001 that is programmed to implement exemplary methods described herein. The server 1001 includes a central processing unit (CPU, also "processor") 1005 which can be a single core processor, a multi core processor, or plurality of processors for parallel processing. The server 1001 also includes memory 1010 (for example random access memory, read-only memory, flash memory); electronic storage unit 1015 (for example hard disk); communications interface 1020 (for example network adaptor) for communicating with one or more other systems; and peripheral devices 1025 which may include cache, other memory, data storage, and/or electronic display adaptors. The memory 1010, storage unit 1015, interface 1020, and peripheral devices 1025 are in communication with the processor 1005 through a communications bus (solid lines), such as a motherboard. The storage unit 1015 can be a data storage unit for storing data. The server 1001 is operatively coupled to a computer network ("network") 1030 with the aid of the communications interface 1020. The network 1030 can be the Internet, an intranet and/or an extranet, an intranet and/or extranet that is in communication with the Internet, a telecommunication or data network. The network 1030 in some cases, with the aid of the server 1001, can implement a peer-to-peer network, which may enable devices coupled to the server 1001 to behave as a client or a server.

The storage unit 1015 can store files, such as subject reports, and/or communications with the caregiver, sequencing data, data about individuals, or any aspect of data associated with the invention.

The server can communicate with one or more remote computer systems through the network 1030. The one or more remote computer systems may be, for example, personal computers, laptops, tablets, telephones, Smart phones, or personal digital assistants.

In some situations, the system 1000 includes a single server 1001. In other situations, the system includes multiple servers in communication with one another through an intranet, extranet and/or the Internet.

The server 1001 can be adapted to store measurement data, patient information from the subject, such as, for example, polymorphisms, mutations, medical history, family history, demographic data and/or other information of potential relevance. Such information can be stored on the storage unit 1015 or the server 1001 and such data can be transmitted through a network.

As used herein, nucleic acid segments are 'in proximity' when they are in phase and can be included, at least in part, in a single read.

EXAMPLES

Example 1. Some Long-Read Sequencing Approaches are Unable to Phase Some Mutations in a Diploid DNA Sample Treatment of a particular human disease depends on the presence of a functional gene product. In the presence of this gene product, a therapeutic molecule is metabolized to yield an effective metabolite. In the absence of the gene product, the therapeutic molecule accumulates and is harmful to the patient.

A patient genome is shotgun sequenced, and it is determined that two point mutations map to the locus encoding the gene product necessary for treatment efficacy. The two point mutations are separated by 30 kb in the assembled shotgun scaffold. Phase information for the two point mutations is unavailable, so practitioners are unable to determine whether the patient harbors a wild-type allele and a double-mutant allele, or in the alternative whether the patient independently harbors two single-mutant null alleles, one at the 5' end of the locus and a second at the 3' end of the locus.

DNA is extracted from a patient and the sample is sequenced on a long-read sequencing machine. The limit of a single long read on average is 10-15 kb. The reads confirm that the patient is heterozygous for both the first and the second mutation. However, given that the mutations in the patient's genome are separated by 30 kb, phase information cannot be acquired using the generated sequence information. As a consequence, practitioners are unable to determine whether the patient harbors a wild-type allele and a doubly-mutant null allele, and is therefore eligible for treatment using the therapeutic molecule, or whether the patient harbors two single mutant null alleles and is therefore unable to metabolize the therapeutic molecule. The patient is denied the treatment and continues to suffer from the condition.

This example demonstrates that long range sequencing approaches used in combination with shotgun reads do not accurately phase mutations, particularly when the mutations are separated by long stretches of homozygous DNA. Furthermore, this example illustrates that failure to accurately assign phase information to genomic sequence has consequences for patient health.

Example 2. Successful Phasing of Mutations in Diploid DNA Sample

DNA from the patient of Example 1 is subjected to phase-analysis using the approaches disclosed herein.

DNA is extracted from the patient described in Example 1. A library of punctuated, insertion shuffled molecules is generated such that phase information is preserved while the relative positions of sequence segments are rearranged.

The extracted DNA is assembled in vitro into reconstituted chromatin. The reconstituted chromatin is cleaved with the restriction enzyme MboI. The resulting sticky ends are partially filled in with a single base in order to prevent re-ligation of the restriction enzyme-generated overhangs. Punctuation oligonucleotides, which have 5' and 3' ends compatible with the partially filled in overhangs of the digested DNA sample, are added to the DNA sample along with a DNA ligase. The punctuation oligonucleotides lack 5' phosphate groups to avoid concatemerization of the oligonucleotides. This ligation step results in the reorganization of DNA segments as ends originally not adjacent to one another are adjacent to each other following ligation. Phase information is maintained since the DNA molecule is bound to crosslinked reconstituted chromatin scaffolds during this process.

Sufficient sequence information is determined such that complete genome information is obtained without the use of a shotgun sequence step independent of phase determination. It is determined that the patient is heterozygous for a first and a second null mutation in the gene of interest.

Furthermore, library molecules are observed wherein the first and second DNA segments containing the two mutations are rearranged without loss of phase information, such that less than 15 kb of sequence separates them. A read spanning the rearranged region is generated, and is found to comprise a first and a second null mutation. Since the first and second DNA segments in the rearranged DNA sample are less than 15 kb apart, the two mutations are able to be both be detected in a single sequencing read, leading to phasing information. This phasing information is used to determine that the patient harbors a double mutant allele. A second read is observed, having a different junction point, but also having a first and a second segment spanning the first and the second heterozygous regions of the locus. It is observed that the first region and the second region in the rearranged molecule both encode wild-type sequence.

Additional molecules comprising phase-preserving rearrangements are sequenced. The additional molecules are found to have punctuation inserts at different positions relative to one another. None of the rearranged molecules harbor a single null mutation and a single wild-type allele. Instead, all of the sequence reads that span both heterozygous regions comprise either wild type alleles at both loci, or null mutations at both loci.

It is determined that the patient genome comprises a double-mutant null allele and a wild-type allele. It is concluded that the treatment is likely to be effective. The patient is administered the therapeutic molecule, and the patient's condition is alleviated through the beneficial activity of the therapeutic molecule.

This example illustrates that the methods and compositions disclosed herein allow concurrent de novo sequence generation and phasing from a single template library. Separate shotgun sequencing libraries and phase-determination libraries are not required, thus substantially reducing cost of the sequencing determination.

This example also illustrates that the methods and compositions disclosed herein allow one to accurately, redundantly phase molecules even though the molecules are largely identical, and the heterozygous positions are separated by regions of identity that are greater than twice the length of the reads in the sequencing technology used.

Example 3. Some Long-Read Sequencing Approaches are Unsuccessful in Phasing of Transposon-Rich Crop DNA Sample It is estimated that approximately 90% of the corn genome is transposable elements, such as transposons. Because of the repetitive nature of some transposons, phasing alleles is difficult. In order to produce a corn strain having improved yield and improved nutritional content, a corn double-mutant line is desired. Both mutations are dominant and are found on opposite ends of a chromosome. A high yield corn strain is crossed to a high carotenoid level corn strain to produce heterozygous lines, which are then self-crossed to generate segregating progeny.

Some of the progeny are observed to demonstrate improved yield and increased nutritional content. The next step in the project is to cross one of the high yield and high nutritional content strains with a strain demonstrating blight resistance. It is known that the blight resistance mutation loses efficacy if it is contained on the same DNA molecule as either the high yield mutation or the improved nutritional content mutation. To minimize timely and costly downstream sequencing and phenotyping experiments, it is desired to perform the blight resistant strain cross with a parental strain that contains the high yield and high nutritional content mutations on the same DNA molecule.

The two parent lines from the initial cross are near-isogenic lines, bred so that variation in their genomes is minimized. As a result, very few markers are found available to facilitate phase determination. DNA is extracted from the thousands of resulting seedlings for sequencing to determine which contain the yield and nutrition mutations in phase on the same DNA molecule. Because the yield gene and carotenoid gene are separated by repetitive, highly conserved transposable elements, and because there is very little variation between the lines aside from these mutations, short read sequencing machines cannot provide phasing information. Because the yield gene mutation and the carotenoid gene mutation are found at opposite ends of a chromosome, both mutations are not able to be detected on a single long read by long-read sequencing technology. As a result, it is not known whether any of the thousands of seedlings possess the desired combination of the high yield mutation and the high nutrition mutation in phase on a single chromosome. It is determined the project cannot remain within budget and therefore the project is cancelled.

Example 4. Successful Phasing of Transposon-Rich Crop DNA Sample

DNA samples from the corn seedlings of Example 3 are extracted and modified to generate segment-shuffled phase preserved sequencing libraries. The resulting rearranged DNA molecules are sequenced on a long-read sequencing machine. Single sequence reads are obtained spanning the yield mutation locus and the nutrition mutation locus, separated by one or more punctuation oligonucleotides. Reads indicating that the two beneficial mutations are in phase on a single molecule are observed for some of the seedling samples. One of the confirmed in-phase high yield and improved nutritional content strains is selected and crossed with the blight resistant strain in order to produce a robust corn strain that will yield much needed increased nutrition in developing countries.

This example demonstrates how the methods and compositions disclosed herein are used to determine phase information for complex genomes having multiple repetitive elements. This technology allows accurate, rapid phase determination even in complex genomes such as those of relevant crop species.

Example 5. Mutation-Baring Nucleic Acid with Indistinguishable Phase

A diploid organism contains two copies of each chromosome of genetic material. Two mutations separated by at least 30 kb of identical sequence are present on a single chromosome of the diploid genome. The DNA sample is sequenced on a long-read sequencing machine having an average read length of 15 kb. It is impossible to determine if the two mutations are contained on the same or different nucleic acid molecules.

Example 6. Determining Phase Information of a Nucleic Acid Sample

DNA is extracted from the organism of Example 5. DNA is assembled in vitro with DNA-binding proteins to generate reconstituted chromatin. The reconstituted chromatin is cleaved to produce sticky ends, which are partially filled in to prevent re-ligation. Punctuation oligonucleotides with ends compatible with the partially filled in sticky ends are added to the chromatin sample along with a DNA ligase. In some instances, the punctuation oligonucleotides are dephosphorylated in order to avoid concatemerization of the oligonucleotides. The DNA segments of the re-ligated chromatin sample are rearranged compared to the starting DNA sample, though phase information is maintained since the molecule is bound to chromatin proteins through the punctuation process. In some instances, the two mutations within the genome are rearranged such that they are less than 15 kb apart. In this case, the separation distance is less than that of the average read length of a long-read sequencing machine. When the rearranged DNA sample is released from the chromatin proteins and sequenced, phase information is determined and sequence information is generated sufficient to generate a de novo sequence scaffold.

Example 7. Determining Phase Information of a Nucleic Acid Sample-Blunt Ligation DNA is extracted from the organism of Example 5 and reassembled with DNA-binding proteins in vitro to generate reconstituted chromatin. DNA is cleaved to produce blunt ends. Punctuation oligonucleotides having blunt ends are ligated to the blunt ends of the cleaved DNA sample. The punctuation oligonucleotides are dephosphorylated in order to avoid concatemerization of the oligonucleotides. The rearranged DNA sample is released from the chromatin proteins and sequenced as in Example 6. When the rearranged DNA sample is released from the chromatin proteins and sequenced, phase information is determined and sequence information is generated sufficient to generate a de novo sequence scaffold.

Example 8. Barcoding a Punctuation Molecule-Short Read

A DNA sample comprising punctuation oligonucleotides is generated as described in any of Examples 6-7. Following release from DNA-binding proteins, the free DNA sample, referred to as a punctuated DNA molecule, is contacted to oligonucleotides comprising at least two segments. One segment contains a barcode and a second segment contains a sequence complementary to the punctuation sequence. After annealing to the punctuation sequences, the barcoded oligonucleotides are extended with polymerase to yield barcoded molecules from the same DNA molecule. These barcoded molecules comprise a barcode sequence, the punctuation complementary sequence, and genomic sequence. Extension products are sequenced on a short-read sequencing machine and phase information is determined by grouping sequence reads having the same barcode into a common phase.

Example 9. Barcoding a Punctuation Molecule-Long Read

A DNA sample is extracted, punctuated, and barcoded as in Example 8. Following extension, barcoded products are bulk ligated together to generate long molecules which are read using long-read sequencing technology. The embedded read pairs are identifiable via the amplification adapters and punctuation sequences. Further phase information is obtained from the barcode sequence of the read pair.

Example 10. Determining Phase Information with Transposon Punctuations

The DNA sample of Example 5 is extracted and reassembled with DNA-binding proteins in vitro to generate reconstituted chromatin. Transposase bound to two unlinked punctuation oligonucleotides is added to the DNA sample. The transposase cleaves exposed DNA segments and inserts the two punctuation oligonucleotides into the DNA. Because the punctuation oligonucleotides in a given transposase are unlinked, the insertion results in two free DNA ends, each terminated by one of the two punctuation oligonucleotides and each tethered to the reconstituted chromatin to preserve phase information. DNA ligase is added to the sample to ligate blunt DNA ends together, resulting in a rearrangement of DNA segments, though phase information is maintained since the DNA molecule is bound to the chromatin proteins throughout this process. The rearranged DNA sample is released from the chromatin proteins and sequenced as in Example 6 to determine phase information.

Example 11. Determining Phase Information with Transposon Punctuations-Short Reads A DNA sample is extracted, reassembled in vitro into reconstituted chromatin, and punctuated with transposases as described in Example 10. Following re-ligation of blunt ends, re-ligated DNA segments are released from protein-DNA complex by restriction digestion, resulting in a plurality of paired ends, which are subsequently ligated to amplification adapters. Following amplification, paired ends are sequenced with short reach technology. It is confidently concluded that for either side of a punctuated junction, the punctuation-adjacent sequence is derived from a common phase of a common molecule.

Example 12. Determining Phase Information with Transposon Punctuations-Long Reads A DNA sample is extracted, reassembled in vitro into reconstituted chromatin, and punctuated with transposases as described in Example 10. Following re-ligation of blunt ends, re-ligated DNA segments are released from protein-DNA complex by restriction digestion, resulting in a plurality of paired ends, which are subsequently ligated to amplification adapters. Following amplification, the plurality of paired ends is bulk ligated together to generate long molecules which are read using long-read sequencing technology. The embedded read pairs are identifiable via the native DNA sequence adjacent to the transposase punctuation sequences. The concatenated punctuated junctions are read on a long-sequence device, and sequence information for multiple junctions is obtained. Junctions are found to map to multiple different chromosomes. However, it is confidently concluded that for either side of a punctuated junction, the punctuation-adjacent sequence is derived from a common phase of a common molecule.

Example 13. Concatemer Generation of Chicago Pairs

A DNA sample is extracted, and assembled with DNA-binding proteins in vitro to generate reconstituted chromatin. DNA is cleaved to produce sticky ends. The sticky ends are filled in with biotinylated nucleotides followed by blunt ligation of the filled-in ends to generate DNA segment pairs, referred to as Chicago pairs. These reshuffled nucleic acids are released from the chromatin proteins, cleaved and streptavidin-binding ligation junctions are isolated. Amplification adapters are added to the free ends of the Chicago pairs. Following amplification, Chicago pairs are bulk ligated together to generate long molecules which are read using a long-read sequencing technology. The embedded read pairs are identifiable via the amplification adapters. Sequence repeats generated in the 'fill-in process' used to introduce the biotinylated bases are also used to identify junctions connecting in phase sequence.

The ligated concatemers are sequenced in a single read of a long-read sequencing device. Because the individual junctions are concatenated, one is able to sequence multiple junctions in a single read.

Example 14. Phasing Hairpin DNA Molecule

A long, punctuated DNA molecule, as generated in any of Examples 6, 7, 9, 10, or 12, is ligated on one end to a hairpin adapter, resulting in a self-annealing single-stranded molecule harboring an inverted repeat. The molecule is fed through a sequencing enzyme and full length sequence of each side of the inverted repeat is obtained. The resulting sequence read corresponds to 2× coverage of a punctuated DNA molecule harboring multiple rearranged segments, each conveying phase information. Sufficient sequence is generated to independently generate a de novo scaffold of the nucleic acid sample.

Example 15. Phasing a Circularized DNA Molecule

A long, punctuated DNA molecule, as generated in any of Examples 6, 7, 9, 10, or 12, is cleaved to form a population of double stranded molecules of a desired length. These molecules are ligated on each end to single stranded adapters. The result is a double stranded DNA template capped by hairpin loops at both ends. The circular molecules are sequenced by continuous sequencing technology. Continuous long read sequencing of molecules containing a long double stranded segment results in a single contiguous read of each molecule. Continuous sequencing of molecules containing a short double stranded segment results in multiple reads of the molecule, which are used either alone or along with continuous long read sequence information to confirm a consensus sequence of the molecule. Genomic segment borders marked by punctuation oligos are identified, and it is concluded that sequence adjacent to a punctuation border is in phase. Sufficient sequence is generated to independently generate a de novo scaffold of the nucleic acid sample.

Example 16. Phased Sequence Assembly Using Multiple Punctuated DNA Molecules A plurality of punctuated DNA molecules is generated as described in any of Examples 6, 7, 9, 10, or 12, and subsequently sequenced using long-read sequencing technology. Sequences from the plurality of punctuated DNA molecules are compared. It is observed that two molecules of the plurality share sequence in common, but have been independently derived and have different punctuation oligos. For a given punctuation oligo on the first molecule, sequence is determined on either side of each of the punctuation oligos, and it is concluded that the sequence segments on either side of the punctuation oligos are in phase on a common molecule. However, the relative positions of the in-phase segments are not clear.

One segment of the first punctuated DNS molecule is compared to the sequence of the second punctuated DNA molecule. It is found that a segment end near a punctuation oligo of the first molecule maps to the interior of a segment of the second punctuated DNA molecule. Sequence of the segment of the second punctuated oligo that aligns beyond the punctuation oligo of the first punctuated DNA molecule is mapped to the first punctuation DNA molecule and a distal segment is identified. Using the second DNA molecule segment as a guide, it is determined that two segments of the first punctuated DNA molecule were positioned adjacent to one another in the original nucleic acid sample.

That is, the first punctuated molecule is used to determine phase information for its constituent segments, while comparison to unpunctuated regions of the second (and additional) punctuated DNA molecules is used to order the segments of the first punctuated molecule. Repeating this process reciprocally, phase and order information is determined for the majority of the segments in each of the plurality of punctuation oligos.

The resulting assembled sequence is a phased sequence of the input DNA molecule prior to rearrangement occurring, and represents a de novo, phased assembly of the nucleic acid sample.

Example 17. Phasing Short-Read Sequencing Data with Long-Read Sequence Data

A punctuated DNA molecule is generated as described in any of Examples 6, 7, 9, 10, or 12 and subsequently sequenced using long-read sequencing technology. In parallel, the input DNA is sequenced using standard short-read shotgun sequencing technology. The shotgun sequence from the sample is mapped to the long-read data generated from the rearranged DNA molecule. The phased genomic sequence reads from the punctuated molecule are mapped to sequencing data obtained from the concurrently generated short-read sequencing. Some of the short-reads map to the long-read generated sequence. This overlap allows short sequence reads to be assigned to the same phase as the genomic sequence generated from the punctuated DNA molecule long sequence read.

Example 18. Nucleic Acid Sequence Library-Long Reads

A plurality of punctuated DNA molecules is generated as described in any of Examples 6, 7, 9, 10, or 12, and subsequently sequenced using long-read sequencing technology. Each punctuated molecule is sequenced, and the sequence reads are analyzed. Sequence reads average 10 kb for the sequence reaction. Sequence reads are identified that comprise at least 500 bases of a first segment and 500 bases of a second segment, joined by a punctuation oligo sequence. The first and second segment sequences are mapped to a scaffold genome and are found to map to contigs that are separated by at least 100 kb.

The first contig and the second contig each comprise a single heterozygous position, the phase of which is not determined in the scaffold. The heterozygous position of the first contig is spanned by the first segment of the long read, and the heterozygous position of the second contig is spanned by the 500 bases of the second segment of the long read.

The reads each span their contigs' respective heterozygous regions. Sequence of the read segments indicates that a first allele of the first contig and a first allele of the second contig are in phase. Since sequences from the first and second nucleic acid segments are detected in a single long sequence read, it is determined that the first and second nucleic acid segments are comprised on the same DNA molecule in the input DNA sample.

This example demonstrates that long reads from punctuation molecules provide phase information for contigs that are positioned far apart from one another on a genome scaffold. The example also demonstrates that the mapping is done with a high degree of confidence because the size of each segment adjacent to the punctuation oligo is great enough to facilitate accurate mapping, and increases the likelihood that a heterozygous position is spanned.

Example 19. Nucleic Acid Sequence Library-Short Reads

A plurality of paired end molecules is generated as described in either Example 8 or 11, and subsequently sequenced using long read sequencing technology. The average read length for the library is determined to be 1 kb. Paired end molecules comprise a first DNA segment and a second DNA segment that, within the input DNA sample, are in phase and separated by a distance greater than 10 kb. Sequence reads are generated from paired end molecules, some of which comprise at least 300 bases of sequence from a first nucleic acid segment and at least 300 bases of sequence from a second nucleic acid segment. Since sequences from the first and second nucleic acid segments are detected in a single sequence read, it is determined that the first and second nucleic acid segments are in phase on the same DNA molecule in the input DNA sample.

This example illustrates that using the rearranged punctuated molecules as taught herein, one generates sequence libraries that yield phase information for DNA segments that are separated in the nucleic acid sample by greater than the read length of the sequencing technology used to sequence them.

Example 20. Nucleic Acid Sequence Library-Concurrent Phased DNA Assembly

A plurality of sequence reads is generated from a punctuated DNA library. The library conveys phase information as described in either Example 18 or 19, such that segments on either side of a punctuation event are determined to be in phase on a single molecule. In addition, the generated sequence reads represents at least 80% of the nucleic acid sequence of the input DNA sample. The sequence reads are used to generate de novo contig information that spans at least 80% of the input DNA sample. Additionally, the sequence reads are used to determine phase information, which is subsequently used to order and orient the contigs relative to each other in order to generate a phased sequence assembly of the input DNA sample.

This example illustrates that punctuated DNA molecules convey phase information and also in some cases encompass sequence information comprising a substantial portion of the total nucleic acid sequence, such that a de novo sequence assembly is concurrently generated.

Example 21. DNA Molecule Phasing

A high molecular weight (HMW) DNA sample is extracted which comprises at least some DNA molecules of at least 100 kb in length. One of the 100 kb DNA molecules comprises a first DNA segment and a second DNA segment that are separated by distance that is greater than the average read length of standard sequencing technologies. The nucleic acid sample is diploid but comprises large regions of sequence identity, complicating phase determination.

For confident phase determination, the first and second DNA segments need to be detected within a single sequencing read. Therefore, the relative position of the first and second DNA segments must be changed such that the first and second DNA segments are separated by a distance that is less than the average read length of standard sequencing technologies. This rearrangement must not result in loss of phase information. This rearrangement is achieved by the methods disclosed herein and as described within any of Examples 6, 7, or 10. During phase-maintaining rearrangement, no more than 10% of the starting HMW DNA molecule is deleted.

That is, the first segment and the second segment are not brought into proximity simply by deleting the intervening sequence. Rather, the segments are rearranged relative to one another without deletion of the majority of the intervening sequence. Since nearly the entire input DNA molecule is preserved, following sequencing, the generated sequence reads are used to assemble, order, and orient de novo generated contigs such that nearly the entire input DNA molecule is sequenced, assembled, and phased.

Example 22. Analysis of Mammalian Cell Culture

A sample of mammalian cell culture is analyzed using the techniques described herein. Briefly, a cell culture of mammalian cells is grown. The cells are cross-linked, cross-linking is quenched, and the cell pellet is stored at −20° C. Cells are homogenized and nuclei are recovered in lysis buffer. Nuclei in the homogenate are bound to SPRI beads and digested using DpnII restriction enzyme. Ends are filled in with no biotin-11-dCTP and blunt ends are ligated. Cross-linking is reversed, DNA is recovered and cleaned up and prepared for sequencing. Sequencing is conducted with Pacific Biosciences SMRT long-read sequencing. In some cases, the DNA can be size selected for molecules at least about 6 kb in length prior to sequencing.

Two samples are tested to ensure ligation occurred properly. FIG. 7 is representative of results indicative of a successful ligation in separate samples. One sees for each sample that ligation has led to a shift toward substantially higher molecular weight nucleic acids.

At FIG. 8, one sees an outcome of such a library generation process. Of over 1,000,000 circular consensus sequence (CSS) reads, only 300,000 are unmapped. There are 1,500,000 mapped segments (-q 1) and 1,350,000 mapped segments (-q 20). For reads with 1 mapped segment, n=500,000; for reads with 2 mapped segments, n=175,000; for reads with 3 mapped segments, n=75,000; for reads with 4 mapped segments, n=30,000; for reads for 5 mapped segments, n=15,000; for reads with 6 mapped segments, n=7,000. This demonstrates that segments are readily identified, and that sequencing the library generation protocol generates reads spanning multiple rearranged segments Table 1 shows clone coverage from reads having the indicated number of mapping segments. As indicated therein, the library generation protocol yields substantial whole genome coverage in total segment sequence, while yielding valuable phasing information as indicated by the number of clones having two or more mapping segments. As many genomes have repetitive sequence, the number of uniquely mapped segments is an underestimate of the total number of segments in a rearranged library constituent molecule.

TABLE 1

Approximate clone coverage from reads with X maximum number of mapping segments.

| | # mapped segments | | | | | |
|---|---|---|---|---|---|---|
| | 1 | 2 | 3 | 4 | 5 | 6 |
| base pairs | 1,3000,000,000 | 18,000,000,000 | 9,000,000,000 | 4,000,000,000 | 1,500,000,000 | 500,000,000 |
| Fold genome (3. Gb) | 0.4 X | 6 X | 3 X | 1.2 X | 0.5 X | 0.5 X |

At FIGS. 9A-9B one sees frequency distributions of distance spanned by reads with X mapped segments for a sample, sorted into 10 kb bins (FIG. 9A) and 1 kb bins (FIG. 9B). Data in this figure reaffirms the conclusion that library generation protocols as disclosed herein yield reads having multiple uniquely mapping segments ligated at recognizable junctions, so as to provide both genome sequence information (often comprising polymorphisms) and phase information, so that these polymorphisms can be phased relative to one another even if they occur in a sample genome at distances greater than the length of a sequence read and are separated by sequence that does not have markers of heterozygosity.

The invention claimed is:

1. A method of sequencing a DNA molecule, comprising:
   (a) providing a first DNA molecule having a first segment, a second segment, and a third segment, wherein the first segment and the second segment are not adjacent on the first DNA molecule, and wherein the third segment is not adjacent to the first segment or the second segment on the first DNA molecule;
   (b) contacting the first DNA molecule to a DNA binding moiety such that the first segment, the second segment, and the third segment are held together independent of a common phosphodiester backbone of the first DNA molecule;
   (c) cleaving the first DNA molecule such that the first segment, the second segment, and the third segment are not joined by a common phosphodiester backbone and comprise at least one exposed end;
   (d) attaching the first segment to the second segment via a phosphodiester bond and attaching the third segment to the second segment via a phosphodiester bond to form a reassembled first DNA molecule; and
   (e) sequencing at least a portion of the reassembled first DNA molecule comprising a junction between the first segment and the second segment and a junction between the second segment and the third segment in a single sequencing read.

2. The method of claim 1, wherein the DNA binding moiety comprises a DNA-binding molecule.

3. The method of claim 2, wherein the DNA-binding molecule comprises a DNA-binding protein.

4. The method of claim 2, wherein the DNA-binding molecule comprises a DNA-binding nanoparticle.

5. The method of claim 2, wherein (b) further comprises contacting the first DNA molecule with a cross-linking agent.

6. The method of claim 1, wherein (c) comprises contacting the first DNA molecule with a restriction endonuclease.

7. The method of claim 1, wherein (c) comprises contacting the first DNA molecule with a nonspecific endonuclease.

8. The method of claim 1, wherein (c) comprises contacting the first DNA molecule with a tagmentation enzyme.

9. The method of claim 1, wherein (c) comprises contacting the first DNA molecule with a transposase.

10. The method of claim 1, wherein (c) comprises shearing the first DNA molecule.

11. The method of claim 1, comprising adding a tag to at least one exposed end of the first segment, the second segment, or the third segment.

12. The method of claim 1, wherein the tag comprises at least one tag selected from the list consisting of a labeled base, a methylated base, a biotinylated base, uridine, and a noncanonical base.

13. The method of claim 1, wherein the first segment comprises a first segment sticky end, and the method further comprises adding a linker oligo comprising an overhang that anneals to the first segment sticky end.

14. The method of claim 1, wherein (d) comprises ligating the first segment to the second segment and ligating the third segment to the second segment.

15. The method of claim 1, wherein the first segment and the second segment are separated by at least 10 kilobases (kb) on the first DNA molecule prior to (c).

16. The method of claim 1, wherein (e) comprises single molecule long-read sequencing.

17. The method of claim 16, wherein the single molecule long-read sequencing comprises generating a read of at least 5 kb.

18. The method of claim 1, wherein the reassembled first DNA molecule comprises a hairpin moiety.

19. The method of claim 1, further comprising determining long-distance phase information from (e).

* * * * *